(12) United States Patent
Slimak

(10) Patent No.: US 7,854,948 B2
(45) Date of Patent: *Dec. 21, 2010

(54) USE OF TROPICAL ROOT CROPS IN DIETARY INTERVENTION STRATEGIES

(76) Inventor: K. M. Slimak, P.O. Box 2444, Springfield, VA (US) 22152

( * ) Notice: Subject to any disclaimer, the term of this patent is extended or adjusted under 35 U.S.C. 154(b) by 770 days.

This patent is subject to a terminal disclaimer.

(21) Appl. No.: 10/682,546

(22) Filed: Oct. 10, 2003

(65) Prior Publication Data

US 2004/0213864 A1   Oct. 28, 2004

Related U.S. Application Data

(62) Division of application No. 09/889,133, filed as application No. PCT/US00/31066 on Nov. 13, 2000, now Pat. No. 6,632,461.

(60) Provisional application No. 60/164,857, filed on Nov. 12, 1999.

(51) Int. Cl.
*A61K 36/00* (2006.01)
*A61K 9/00* (2006.01)
*A61K 47/00* (2006.01)

(52) U.S. Cl. .................. 424/773; 424/725; 424/400; 424/439

(58) Field of Classification Search .............. 424/773, 424/435, 442, 725
See application file for complete search history.

(56) References Cited

U.S. PATENT DOCUMENTS

| | | | |
|---|---|---|---|
| 4,337 A | 12/1845 | Edwards |
| 34,389 A | 2/1862 | Andres et al. |
| 38,039 A | 3/1863 | Frost |
| 77,995 A | 5/1868 | Marshall |
| 91,554 A | 6/1869 | Marshall |
| 100,587 A | 3/1870 | Baylor |
| 125,247 A | 4/1872 | Adamson et al. |
| 310,927 A | 1/1885 | Whitcomb |
| 592,906 A | 11/1897 | Gere |
| 1,211,984 A | 12/1914 | Malcolm |
| 1,151,805 A | 9/1915 | Ray |
| 1,154,805 A | 9/1915 | Ray |
| 1,193,828 A | 8/1916 | Sattler |
| 1,194,455 A | 8/1916 | Williams |
| 1,238,371 A | 8/1917 | Williams |
| 1,470,929 A | 10/1923 | Li |
| 1,571,945 A | 3/1926 | Heimerdigner |
| 1,676,160 A | 7/1928 | Ruffner |
| 2,168,246 A | 8/1939 | Shepherd |
| 2,352,670 A | 7/1944 | Volpertas |
| 2,469,995 A | 12/1949 | Schaul |
| 2,490,431 A | 12/1949 | Green et al. |
| 2,687,960 A | 8/1954 | Sharp |
| 3,162,536 A | 12/1964 | Kaufmann |
| 3,208,855 A | 9/1965 | Enoch et al. |
| 3,346,390 A | 10/1967 | Pichel et al. |
| 3,394,012 A | 7/1968 | Kolton et al. |
| 3,493,390 A | 2/1970 | Succo |
| 3,497,360 A | 2/1970 | Schaefer et al. |
| 3,615,658 A | 10/1971 | Glabe |
| 3,762,423 A | 10/1973 | Simpson et al. |
| 3,767,423 A | 10/1973 | Tsantir |
| 3,767,424 A | 10/1973 | Shimizu et al. |
| 3,881,028 A | 4/1975 | Caposella, Jr. |
| 4,028,469 A | 6/1977 | Kritchevskt et al. |
| 4,109,018 A | 8/1978 | Thompson |
| RE29,773 E | 9/1978 | Wisdom et al. |
| 4,277,510 A | 7/1981 | Wicklund et al. |
| 4,283,425 A | 8/1981 | Yuan et al. |
| 4,520,034 A | 5/1985 | Ishii et al. |
| 4,565,705 A | 1/1986 | Snider |
| 4,749,579 A | 6/1988 | Haydock et al. |
| 4,756,916 A | 7/1988 | Dreher et al. |
| 4,795,653 A | 1/1989 | Bommarito |
| 4,853,236 A | 8/1989 | Langler |
| 4,865,863 A | 9/1989 | Prosese |
| 4,906,483 A | 3/1990 | Kloos |

(Continued)

FOREIGN PATENT DOCUMENTS

| | | |
|---|---|---|
| CA | 1313602 | 2/1993 |
| DE | 1517050 | 8/1974 |
| DE | 2950315 | 6/1981 |
| DE | 3141174 | 4/1983 |
| FR | 1395654 | 2/1965 |
| FR | 2574633 | 6/1986 |
| JP | 104850 | 8/1980 |
| WO | 8704599 | 8/1987 |

*Primary Examiner*—Christophe R Tate
*Assistant Examiner*—Randall Winston
(74) *Attorney, Agent, or Firm*—Novak Druce & Quigg LLP

(57) ABSTRACT

This invention relates to an effective dietary intervention plan. In one aspect all food is withheld for a period of at least 5 days, except for tropical root crops. In another aspect the invention relates to the treatment of various symptoms, conditions or diseases such as Diarrhea, constipation, congestion, eczema, asthma, fatigue, muscle weakness, tension, and spasms, irritable bowel syndrome, swelling, anxiety, multiple chemical sensitivities, moderate to extensive and moderate to severe symptoms due to food allergies, sensitivities, and intolerances, bloating, pain, headaches, leaky gut, hyperactivity, sleeping difficulties, severe underweight, eating disorders, obsessive, compulsive disorders, panic attacks, sensory sensitivities, Alzheimer's disease, acid reflux, irritability, delayed motor skills, delayed social skills, autism, PDD, infantile spasms, seizures by withholding from the patient for a period of at least 5 days all food except for concentrated forms of concentrated tropical root crops. Preferably the patient is also removed from external environmental sources of allergens. After the initial withholding period new foods may be introduced according to a particular selection and schedule.

18 Claims, 4 Drawing Sheets

U.S. PATENT DOCUMENTS

| | | |
|---|---|---|
| 4,911,943 A | 3/1990 | Slimak |
| 4,917,908 A | 4/1990 | Prosise |
| 4,917,909 A | 4/1990 | Prosise |
| 4,919,965 A | 4/1990 | Childers, Jr. |
| 4,923,709 A | 5/1990 | Slimak |
| 4,925,696 A | 5/1990 | Slimak |
| 4,925,697 A | 5/1990 | Slimak |
| 4,929,467 A | 5/1990 | Slimak |
| 4,933,199 A | 6/1990 | Neel et al. |
| 4,946,703 A | 8/1990 | Slimak |
| 5,204,137 A | 4/1993 | Slimak |
| 5,234,706 A | 8/1993 | Slimak |
| 5,244,689 A | 9/1993 | Slimak |
| 5,789,012 A * | 8/1998 | Slimak ................ 426/629 |

\* cited by examiner

Drawings:

Recovery Patterns in Autistic Individuals

USE OF TROPICAL ROOT CROPS IN DIETARY INTERVENTION STRATEGIES

CROSS-REFERENCE TO RELATED APPLICATIONS

This application is a divisional application of U.S. Ser. No. 09/889,133, filed Jul. 12, 2001 now U.S. Pat. No. 6,632,246, which, in turn, is a §371 national phase application of International Application PCT/US00/31066, filed Nov. 13, 2000, claiming benefit of U.S. Provisional Application 60/164,857, filed Nov. 12, 1999, the entire disclosures of which is herein incorporated by reference.

The following related patents are hereby incorporated by reference in their entirety:

U.S. Pat. No. 5,789,012, issued Aug. 4, 1998, titled "Products From Sweet Potatoes, Cassava, Edible Aroids, Amaranth, Yams, Lotus, Potatoes, And Other Roots, Seeds And Fruit", U.S. Pat. No. 5,234,706, issued Aug. 10, 1993, titled "Processes For Products From Potatoes, And Other Roots, Seeds And Fruit", U.S. Pat. No. 5,244,689, issued Sep. 14, 1993, titled "Flour, Bread, Milk, And Other Products From White Sweet Potatoes, Cassava, Edible Aroids, Amaranth, Yams, And Lotus", U.S. Pat. No. 5,204,137, issued Apr. 20, 1993, titled "Processes For Products From Sweet Potato", U.S. Pat. No. 4,911,943, issued Mar. 27, 1990, titled "Processes For Products From Amaranth", U.S. Pat. No. 4,946,703, issued Aug. 7, 1990, titled "Processes For Products From True Yams", U.S. Pat. No. 4,925,696, issued May 15, 1990, titled "Processes For Products From Malanga", U.S. Pat. No. 4,925,697, issued May 15, 1990, titled "Process For Products From Sweet Potato", U.S. Pat. No. 4,923,709, issued May 8, 1990, titled "Processes For Products From Cassava", U.S. Pat. No. 4,929,467, issued May 29, 1990, titled "Processes For Products From Lotus", PCT Patent WO87/04599, filed Feb. 2, 1987, issued Aug. 1, 1988, titled "Flour, Bread, Milk, And Other Products From White Sweet Potatoes, Cassava, Edible Aroids, Amaranth, Yams, And Lotus", and Canadian Patent No. 1,313,602, filed on Feb. 2, 1987, issued Feb. 16, 1993, titled "Flour, Bread, Milk, And Other Products From White Sweet Potatoes, Cassava, Edible Aroids, Amaranth, Yams, And Lotus".

Also incorporated in their entirety by reference are the references cited in U.S. Pat. No. 5,789,012, including the listed US patent documents, the listed foreign documents, and the other publications listed.

BACKGROUND OF THE INVENTION (1) Field of Invention

This invention relates to an effective dietary intervention plan. In one aspect all food is withheld for a period of at least 5 days, except for tropical root crops. In another aspect the invention relates to the treatment of various symptoms, conditions or diseases such as diarrhea, constipation, congestion, eczema, asthma, fatigue, muscle weakness, tension, and spasms, irritable bowel syndrome, swelling, anxiety, multiple chemical sensitivities, moderate to extensive and moderate to severe symptoms due to food allergies, sensitivities, and intolerances, bloating, pain, headaches, leaky gut, hyperactivity, sleeping difficulties, severe underweight, eating disorders, obsessive, compulsive disorders, panic attacks, sensory sensitivities, Alzheimer's disease, acid reflux, irritability, delayed motor skills, delayed social skills, autism, PDD, infantile spasms, seizures by withholding from the patient for a period of at least 5 days all food except for concentrated forms of concentrated tropical root crops. Preferably the patient is also removed from external environmental sources of allergens. After the initial withholding period new foods may be introduced according to a particular selection and schedule.

In another aspect of the invention the subject undergoes an effective dietary intervention plan in which at least five (5) tropical root crops are selected, each eaten on a successive day, along with selected other meat, vegetables, and oils that the subject has never eaten before, eating a different selection of meat, vegetables, and oils each from different food families each day, with no food or food family being repeated for at least 5 days. In another aspect the invention relates to the treatment of various symptoms, conditions or diseases such as Diarrhea, constipation, congestion, eczema, asthma, fatigue, muscle weakness, tension, and spasms, irritable bowel syndrome, swelling, anxiety, multiple chemical sensitivities, moderate to extensive and moderate to severe symptoms due to food allergies, sensitivities, and intolerances, bloating, pain, headaches, leaky gut, hyperactivity, sleeping difficulties, severe underweight, eating disorders, obsessive, compulsive disorders, panic attacks, sensory sensitivities, Alzheimer's disease, acid reflux, irritability, delayed motor skills, delayed social skills, autism, PDD, infantile spasms, seizures by withholding from the patient for a period of at least 5 days all food except for concentrated forms of concentrated tropical root crops. Preferably the patient is also removed from external environmental sources of allergens. After the initial withholding period new foods may be introduced according to a particular selection and schedule.

In another aspect of the invention the subject undergoes an effective dietary intervention plan in which at least seven (7) tropical root crops are selected, each eaten on a successive day, along with selected other meat, vegetables, and oils that the subject has never eaten before, eating a different selection of meat, vegetables, and oils each from different food families each day, with no food or food family being repeated for at least 7 days. In another aspect the invention relates to the treatment of various symptoms, conditions or diseases such as Diarrhea, constipation, congestion, eczema, asthma, fatigue, muscle weakness, tension, and spasms, irritable bowel syndrome, swelling, anxiety, multiple chemical sensitivities, moderate to extensive and moderate to severe symptoms due to food allergies, sensitivities, and intolerances, bloating, pain, headaches, leaky gut, hyperactivity, sleeping difficulties, severe underweight, eating disorders, obsessive, compulsive disorders, panic attacks, sensory sensitivities, Alzheimer's disease, acid reflux, irritability, delayed motor skills, delayed social skills, autism, PDD, infantile spasms, seizures by withholding from the patient for a period of at least 5 days all food except for concentrated forms of concentrated tropical root crops. Preferably the patient is also removed from external environmental sources of allergens. After the initial withholding period new foods may be introduced according to a particular selection and schedule.

(2) Description of the Background

The emphasis of the above referenced patents was to provide as many new food choices for food allergic and food sensitive persons as possible, so they could at least find something to eat, could eat the foods they needed in concentrated form so that they would be able to eat enough calories, and would have sufficient variety to fit into their cultural preferences, and finally sufficient variety not to be boring. Although this was an appropriate goal, it was found that simply providing a selection of new foods to choose from was not the highly effective solution hoped for. For the food allergic/sensitive individual several very important problems emerged:

1) Identification of problem foods. Although the presence of food reactions, a family history of food allergies; and the presence of chronic, persistent symptoms are characteristic of an individual who is likely to have food sensitivities, problems still exist limiting our success in identifying the specific allergens responsible (Williams, 2000).

One of the reasons that problem foods are difficult to identify is due to the fact that not all of the biochemical mechanisms are well understood and identified. Although about 30% of the population of countries around the world report food allergy problems (Matthews et al, 1998), only 1-2% of the complaints are identified as due a true food allergy, an abnormal or exaggerated immune-system response to specific proteins found in foods. The remainder are generally characterized as sensitivities, which are caused by other immune system mechanisms that are not well understood, intolerances, which are attributed to the lack of an appropriate enzyme, anxiety related to fear of past reactions that were not accurately characterized, and by somatic reactions triggered by past abusive situations. The ability to accurately apportion an individual's food reactions among the latter four, and further to correctly associate a specific food with it's fully characterized reaction pattern has until now essentially not been possible.

Although there are numerous tests available, including but not limited to, IgG specific RAST (radioallergosorbent test), IgG4 Specific RAST, IgE specific RAST, skin tests (scratch test or prick test), ELISA/EIA (Enzyme Immunoassays) panels to test for the presence of IgG and sometimes IgE antibodies, Scratch test, EPT (End-point-Titration), Cytotoxic Test, and ALCAT, no test is able to accurately and completely identify the foods that are the problem, even for those tests whose scope is narrow, e.g., RAST.

This investigator maintains that identification of problem foods is far more complex than anticipated by other investigators. All of the above tests focus on only one component of foods, namely the protein fraction. As should be readily available to any who care to think more broadly, there are far more substances than protein in food. In any given cell there are literally hundreds of thousands of substances present. They range from small simple molecules to complex, convoluted structural chemicals. The cells being the chemical soup that they are, literally any one or any combination of these substances could cause adverse physical symptoms in any given individual. Even in the conventional protein model, it is well known that the active regions of a protein are limited to a relatively few sites on that protein that have specific stereochemical configurations that accept and react with appropriately configured portions of other proteins or any number of smaller substances that match the stereochemical requirements.

In light of this, this investigator fails to understand why the study of the allergenic substances and the immune system of humans is limited to only proteins. There are myriad numbers of non-protein chemicals in an organism that an individual may react to, and reaction patterns to these substances have yet to be investigated, this investigator maintains that there is a large part of the immune system or some other parallel system that has yet to be identified, studied and characterized fully.

So—in addition to the fact that even the protein allergies are not well identified, and there are sensitivities, intolerances, anxiety and somatic responses to myriad numbers of non-proteinaceous substances, now consider the changing characteristics of food. This complex milieu of hundreds of thousands of substances changes in composition depending upon numbers of factors: ripening, harvesting, drying, during processing, during post harvest storage, before and after peeling, before and after cooking, during chewing, during digestion, during absorption, during metabolism, and during assimilation.

Reactions commonly involve one or more but not all systems of the body. Thus a food may show no reaction in a skin test but cause a severe reaction in the digestive tract. A reaction may depend on the amount of food consumed, the presence of other foods that can slow digestion, and medications such as antihistamines that may hide reactions. A reaction apparently due to a food or food additive may in reality be due to another food that was accidentally added to the mixture during preparation. Toxins and food poisoning can cause symptoms that can be confused with food allergy. Some medical conditions such as hiatal hernia, ulcers and diverticulosis are associated with acute symptoms after eating.

Because of these daunting complexities, not only is no existing test adequate for the accurate identification of food allergies and sensitivities and intolerances, this investigator does not expect there to be derived a blood, in vitro, or in vivo test that would accurately identify all problem foods and apply accurately to all of the above situations.

At best, lab tests accurately identify the allergy-defined reactions that are the most obvious and serious. More subtle reactions are rarely accurately identified by these tests. Patient history is then relied upon, but unfortunately the patient is also able to tell only the most obvious reactions. The remainder tends to be confusing to both the patient and practitioner.

Although having a selection of new, unfamiliar foods to try is helpful, the lack of reliable information on foods to avoid tended to make a mockery of attempts at dietary intervention. Including new foods in a diet that also contains problem foods cannot provide the symptom relief desired by the food-allergic or food sensitive individual, and the result tended to be frustrating and not achieve the desired relief from symptoms.

The consensus in the medical community regarding testing for foods is generally that although not completely accurate, the tests at least give some indication of what some problem foods are, and they are better than nothing. From the viewpoint of a person suffering from food-related symptoms, this is an unsatisfying and unacceptable approach.

2) Distinguishing between symptoms associated with foods and those associated with other sources such as pollen, mold, pets, chemical sensitivities: Symptoms caused by foods can also be caused by other environmental factors such as pollen, mold, pets, and chemical sensitivities. Even if a diet were to be completely correct, and eliminate all food-related problems, a food sensitive individual might not even be able to tell much, since a food sensitive individual frequently also experiences similar symptoms caused by environmental exposures such as to pollen, mold, pets, and chemical exposures.

3) Persons following dietary advice tended to develop new food-related problems: A person with food allergies, sensitivities or intolerances who tries to develop a diet, is generally only able to correctly eliminate a few of the strongest food sensitivities. Because when one eliminates a food, it has to be substituted with something else, the food allergic person generally increases consumption of the most similar food available and this food is the very food that the individual is next most likely to become sensitive to. For example a person who is very sensitive to wheat is very likely to adjust the diet and eat large amounts of rye or oats, which are quite closely related to wheat.

At the same time, the person tends to inadvertently eat fewer calories. There are fewer uses for the substituted foods, and the number of ways the alternative foods are eaten is fewer. The allergic person generally fails to adjust by eating larger portions of the remaining complex carbohydrates.

Developing new food sensitivities and experiencing increasingly severe symptoms to other foods is a very common problem. When many problem foods remain undetected, and foods closely related to foods already eliminated are eaten more frequently, and overall level of nourishment falls, the effect can only be an eventual decline in general health and development of new food sensitivities and an increase in severity of symptoms.

In addition, because many individuals with food sensitivities also experienced symptoms from non-food items to which they might be continually exposed, such as molds or a recurring chemical exposure, the relief provided by elimination of some of the foods was insufficient, in terms of the overall level of exposures, to prevent the continuing long term deterioration in overall health that many individuals experience.

4) Use of supplements: Often individuals are advised to eliminate some foods from their diets, based on the results of the above inadequate tests, and then to take a number of dietary supplements to counteract the remaining symptoms the person is experiencing. Although some persons have improved using this strategy, complete relief from symptoms is very rare. Usually individuals remain at about the same symptom level as without treatment, or are slightly improved. The reason for this is that not all problem foods are removed form the diet, and the supplements provided generally are derived from some of the problem foods. This is particularly easy to occur since all of the sensitivities are unknown to begin with, so the provider is unable to specify the ingredients the individual would need to avoid.

5) One method, accepted throughout the medical and scientific community as an accurate way to know what foods are well tolerated, is elimination and challenge (AAFA 2000). Except in instances in which the symptoms are very severe this method can be very confusing and inaccurate. For example, an individual with multiple food allergies, for instance 20 moderate to mild reactions, who is advised to eliminate one of the foods on a trial basis, is still consuming the remaining 19 in the diet. Since not all foods are eaten on the same day, and a food reaction may be immediate or delayed, and may last four days or longer before tapering off resulting in a continual fluctuation in symptoms, how is one to accurately determine whether an improvement occurred at all, that the improvement observed, if any, was actually due to the removal of the one food. Often the individual involved has a difficult time deciding if there was actually a change or not.

Because of the inherent variability that occurs using this method, it can take 3 or more years for an individual with multiple food sensitivities to identify many of the problem foods. This is a very discouraging prospect, because in the process they have often managed to become allergic or sensitive to a whole set of new foods. The result is a virtually non-ending set of experimentation that never fully provides the set of information needed by the individual.

6) Rotary diversified diet and other approaches have also not proven to fully solve food related problems. For the reasons provided above, the majority of individuals following such approaches rotate every 2-4 days foods still causing them problems that were unidentified by inaccurate testing methods and foods that are the most likely to cause them problems next. Further, these diets are different enough that the former eating patterns are inappropriate and the individual inadvertently seriously under eats, generally eating only about 20-25% of the daily calories needed. Since it generally takes about 4 days for a food to be eliminated from the body and all absorbed and extracted components sufficiently metabolized and assimilated to the point that they are no longer recognized by the body, a 2-4 day rotation diet is essentially no rotation diet at all. A person on a 2-4 day rotation diet has essentially all of the food residues in his body all of the time. In addition to the effects of the dietary supplements mentioned earlier, the result is generally very frustrating to the individual, who generally feels some small amount of temporary improvement followed by a return of the previous symptoms at the previous level of greater in intensity. The individual then generally follows a frustrating, frightening series of cycles of diet modification followed by temporary improvement and subsequent development of new allergies and sensitivities.

The result is that in spite of the availability of new food choices, virtually every person suffering from mild to moderately severe food allergies, sensitivities and intolerances remains with the problem foods unidentified, continues to regularly consume foods that bother them, and suffer the adverse effects on health that come with continual, long-term adverse effects of chronic reactions, chronic irritation and tissue injury, and chronic inflammation.

It is widely reported that in the last few decades the reports of food allergies, sensitivities and intolerances have doubled, from 15 to 30%. This investigator notes that there has been a similar and simultaneous increase in the incidence and occurrence of a wide variety of chronic diseases and chronic health complaints. These begin in infancy with increases in the occurrence of colic, digestive upsets, congestion, eczema, various rashes, and asthma, and continue to autism, migraine headaches, fatigue, irritable bowel syndrome, and other digestive conditions, anxiety, Alzheimer's disease, diabetes, arthritis, multiple sclerosis, seizures, and so forth.

The work of this investigator suggests that the increases in the occurrence of chronic disease are not merely coincidental, but are closely related. This investigator has discovered that many individual suffering for longer periods of time with altered body function caused by chronic untreated food allergies, sensitivities and intolerances, often develop serious chronic diseases that otherwise could be avoided. Further, if the damage caused by the disease is not yet permanent, this investigator has found that these chronic diseases can be fully reversed when food and other factors are completely eliminated, and exposure no longer occurs.

Still further consider the problems faced by individuals suffering from multiple chemical sensitivities. The ability to accurately diagnose the problem and accurately identify the substances the individual is sensitive to is poor, even worse than that for foods. Physicians and other health professionals tend to rely strongly on the patient's descriptions of symptoms, circumstances and complaints, in making cause and effect assessments. This approach works well in only those rare instances in which an individual experiences no other allergies and sensitivities and so forth.

Generally a person experiencing multiple food sensitivities also experiences multiple chemical sensitivities, and also some anxiety, incorrect beliefs, and occasionally some symptoms associated with somatic disorders. These symptoms merge and blend to form an undulating pattern of symptoms and as a result the patient experiences some better days or parts of days and some worse days or parts of days. Even when accurately described by an extraordinarily observant individual, the symptoms experienced are so complicated that accurate cause and effect associations are virtually impossible.

Health professionals tend to contain the entire symptom picture within their discipline, meaning that at best only a small part of the total problem is addressed. Thus a person experiencing the above array of problems, if treated by an environmental physician, will generally find that professional attributing most of the problems to multiple chemical sensitivities. A wide variety of often very restrictive and expensive changes in home, lifestyle, and sometimes occupation are made, without the benefit of accurate identification of the substances actually causing the problems, but recommendations appropriate for an individual with sensitivities to almost everything as if all of the symptoms are being caused by multiple chemical sensitivities. The patient following these guidelines, even whole heartedly and diligently, generally finds after spending many thousands of dollars, that they are some better but overall have not improved all that much.

If this same person were to have been treated by a person specializing in food allergies, there would be few if any foods identified. The patient eliminating the foods that are identified generally feels that they are some better but overall have not improved all that much. If tests show no food allergies following within the standard true allergy definition, then no useful guidance is provided.

If this same person were to have been treated by a person specializing more broadly in food allergies and sensitivities, they the person would be tested by a variety of food tests, all of which have dubious results, and would at best be given a four day rotation diet that avoids the foods identified by the tests and substituting closely related foods to those omitted, and prescribed large numbers of supplements and digestive enzymes derived from foods they should be avoiding. The patient following this approach carefully and completely, generally feels that they are some better but overall have not improved all that much. Unfortunately these individuals often lose massive amounts of weight and in a few months become sensitive to more foods and experience more severe symptoms.

If this same person were to have been treated by a person specializing in anxiety disorders, the patient will generally find that professional attributing most of the array of symptoms to an anxiety disorder, and will be treated with counseling and appropriate pharmaceuticals for this problem. The patient generally reports that they are some better but overall have not improved all that much.

If this same person were diagnosed as suffering from a somatic disorder, the patient frequently becomes hostile and indignant, feeling that the complaints and very real symptoms are being ignored and undervalued by the practitioner. These individuals leave feeling undermined, misunderstood and insulted. The rare few who accept the diagnosis and enter treatment, find that they are some better but overall have not improved all that much.

The individual then desperately often turns to a variety of alternative therapies; in each instance the professional again assures the individual that all of the symptoms being experienced are likely to be eliminated by his method. People undergo weeks of sauna treatment, have their mercury amalgam fillings removed, undergo colonics and other cleansing therapies, undergo all sorts of acupuncture, biofeedback, and the like, and so forth, and overall find that they are some better but overall have not improved all that much.

Moderately severe to mild or subtle food allergies, sensitivities and intolerances can no longer be ignored or grudgingly tolerated by the medical community as uninteresting and unimportant. The answer to their commonly asked question: Where is the universal effect? As this investigator will show, it is right under their nose, presenting as a major causal factor in many chronic and debilitating diseases.

For the food sensitive individual, this means that mild or moderate allergies, sensitivities and intolerances are no longer something to 'put up with' and partially ameliorated with medications to alleviate some of the symptoms, food-related problems are significant and if unrecognized and not avoided, can cause serious chronic and debilitating diseases.

To sum, this investigator finds this field is—A MESS. Until now there has been no effective strategy available to either the conventional medical community or to the alternative medical community for accurately separating out the various causes and accurately identifying the specific agents or substances responsible for causing symptoms in each area. The incredible complexity coupled with inappropriate belief strategies and paradigms in both the conventional medical community and the alternative medical community have prevented the development of effective strategies.

It became very clear to this investigator that the complexities associated with food allergies and sensitivities, intolerances, and food associated anxieties and somatic disorders were not going to lead to effective strategies for treatment for a very long time, if ever, should the current directions and research emphasis continue. This investigator abandoned a search for a better in vitro or in vivo testing method, realizing that the huge number of substances and the many changes that occur to these substances over time, presented an asymptotically difficult challenge, and indicated that a completely different approach would be needed to effectively address the above described problems. And so, began to develop a completely new approach.

SUMMARY OF THE INVENTION

Detailed Descriptions of the Invention

THE INSTANT METHOD FOR FOODS: stop searching for tests that identify problem foods, and look for universally well tolerated foods.

It is generally known that if a person does not eat a food that he is allergic or sensitive to or that bothers in any way, he cannot experience symptoms from that food. In other words there is a common sense saying, so obvious that it is almost a joke that applies, 'If you don't eat it, it can't bother you'. In essence, almost all of the above describe problems and ineffective strategies and testing methods for foods seek to achieve this goal. However, rather that searching for the problem foods to avoid as is the aim of the prior art, this investigator sought to search for the set of foods most likely to be tolerated by any individual, even the most food sensitive individual.

This investigator began to conduct research with these highly sensitive individuals with severe and complex food sensitivities and the above described other problems, seeking an effective, easily implemented dietary intervention strategy.

This investigator also began to make many different unusual foods available to individuals suffering from food allergies, sensitivities, intolerances, anxieties and somatic disorders, i.e., food-related problems; these foods are described in the above referenced patent applications. This investigator offered these foods to the most sensitive, severely affected individuals in the US, particularly individuals with complicated cases involving subtle or moderately severe symptoms from large numbers of foods and many other factors as well.

Many foods were made available to customers without guidance of any kind; a large number of products for each of the following—white sweet potato, malanga, cassava, amaranth, quinoa, buckwheat, lotus, true yam, arrowroot, and many others. The foods in many forms were provided to persons with particularly complex, debilitating, life altering symptoms and conditions, and the patterns of food selections were studied. It quickly became possible to interpret the food selections of these individuals. Individuals who didn't know what they could tolerate would order small quantities of large numbers of foods, presumably to test by direct challenge. As they worked out their diets, they would eliminate some foods and add others, still selecting relatively small quantities of a large variety of foods. When they finally settled on the foods that worked best for them, the pattern changed dramatically. The number of foods selected became relatively few, generally 4 or 5, and they were ordered in large quantities, and the same foods were ordered over and over for a long period of time, often years.

This investigator began to notice a surprising, unexpected pattern in the foods selected by these seriously ill individuals with complex, life altering problems. The individuals were self-selecting the same foods. This investigator then searched over an eight-year period, the archived food selections of individuals whose had been able to identify the set of foods that worked for them. To my surprise, the foods were the same! The foods were white sweet potato, malanga, cassava, true yam, water chestnut, arrowroot, and lotus. This investigator noticed that these carbohydrates were all tropical root crops. Although a variety of other unusual foods were offered, such as buckwheat, amaranth, quinoa, and milo, and these were half the price or less, none of these foods were included in the final, long-term selections.

This discovery was surprising and unanticipated the art teaches strongly away. The consensus, strongly held, is that anyone may be sensitive to any food; one man's meat is another man's poison. For this reason, there has never been a search for a set of generally well-tolerated food. This investigator's study of the food choices of over one thousand of the most severely sensitive persons in the country suggested strongly otherwise. Separated by years, by thousands of miles, and without discussion or guidance, these individuals, when they finally figured out the foods that worked the best for them, were selecting the same foods. Most of these persons were apparently on four day rotation diets because the repeated orders generally were for four foods. The specific four foods selected varied from person to person, but they were always selected from the tropical root crops offered: white sweet potato, cassava, malanga, true yam, lotus, water chestnut, and arrowroot.

This investigator noted with surprise and interest that no seed was selected, and no root from northern climates or higher elevations, eg potatoes and artichokes was selected. This investigator reasons in hindsight that tropical root crops were selected for the following reasons: 1) seeds tend to be more moldy than the instant products of the above referenced patents. During the ripening process, the high moisture slowly transitioning to lower moisture, the tight seed coat which maintains a quiet, dark environment, and the warmth of the sun are ideal for mold formation. Although the patented products derived from tropical root crops of applicant are grown in the soil, the extreme freshness of the roots when processed and the processing steps that prevent contact of dirt and mold with the freshly peeled flesh make the products of the above inventions far less moldy than products that are seed based. This is very important since most individuals suffering from complex allergies, sensitivities and intolerances to foods, chemicals and other environmental factors are also sensitive to molds. The patented products of the above referenced patents of Applicant are also far less moldy than the seed-based products. 2) tropical root crops may be seen by the immune system as 'less foreign'. The tropical root crops listed above grow naturally in the regions of the world from which the human race emerged. This would explain the reason that only the tropical root crops were selected; they may simply be the primary carbohydrates of the human race as man emerged as man, which would be the carbohydrates that man's immune system was designed to recognize as not foreign. It would stand to reason that these foods are the least likely, and may by among the last for a sensitive individual to react to. In addition, persons with immature immune systems would be more likely to tolerate these foods than other foods that were added to the human diet only a few hundred or thousand years ago.

The historical advantage of many of the newer foods, especially grains, is that their more concentrated forms of calories made it possible for people to be better nourished, healthier, live longer, and could support a larger population. The introduction of grains, which represent concentrated forms of calories, in many ways made the emergence of civilization possible. Even if 'foreign' in comparison to the better tolerated roots, grains and seeds offered more total calories, which were essential.

Although the fresh root form of tropical root crops may be the most well tolerated of all carbohydrates, they still present the primary, fundamental disadvantage that they always have, namely not concentrated enough to easily maintain adequate nourishment. Children 7-10 years in age, for example, require 330 grams of carbohydrates per day for adequate nourishment according to the Recommended dietary Allowances of the National Research Council (National Academy of Sciences, 1980, *Recommended Dietary Allowances*, $9^{th}$ edition). The average root contains about 90 grams per pound. To meet the carbohydrate requirement for resting and light activity, the average 7 year old child must eat almost 4 pounds per day, and a moderately active, 180 pound teenage boy must eat a minimum of 7.25 pounds of tropical roots per day to meet his recommended dietary allowance for carbohydrates.

The need for concentrated carbohydrates was the primary reason that this investigator initially developed the food alternatives described in the above referenced patents of Applicant. The personal experience of this investigator with fresh roots, provides an example of the difficulties encountered when concentrated forms of root crops are not available.

When this investigator's children were small, they were placed on a diet in which sweet potatoes were the primary carbohydrate source. The diet consisted of sweet potatoes, venison, guava and sunflower oil. The children were initially allowed to eat as much as they wanted, stop when full, and so forth. One month later, at a regular check-up the pediatrician expressed concern. Although the children were free of their many previous symptoms associated with extensive, severe food allergies, they had lost about 25% of total body weight, and had not shown an increase in height at all. The doctor recognized that the health of the children was in jeopardy since under nourishment could easily lead to a proliferation of new food sensitivities including the few foods the children were eating.

This investigator then carefully calculated the quantities each child needed to eat each day, according to the RDA's provided by the National Research Council. After adjusting to the shock of how high the numbers were, and rechecking the figures several times, this investigator divided the food into three meals, plus snacks, and tried to feed it to the children. The quantities were daunting, and as soon as the children had eaten until they were no longer hungry, they were satisfied and uninterested in eating more.

It became an unhappy battle at mealtimes to try to get the children to eat the impossibly large quantities they really needed. The children quickly tired of eating only boiled, fried, or baked roots, and were simply unable to consume the quantities they needed to maintain their weight and height.

The children also were not accustomed to eating only variations of fresh roots. They were used to breads, cereals, milk, pancakes, muffins, sandwiches, desserts, pastas and so forth that they were used to and saw their friends eating. The point is that in addition to concentrated forms of the foods, there needed to be available foods that fit into the cultural context familiar to the individual. Foods are eaten in a social context that is also important to the acceptance of the foods and the personal feelings of the individual eating them.

This investigator has observed personally in her own family, and professionally in working with many others, that providing the new well-tolerated foods in familiar shapes, textures and forms is essential to getting the food sensitive individual to accept them, and to feel comfortable emotionally about eating them. The variety of food products described in the above referenced patents is essential to the successful acceptance of the new foods by the food sensitive individual who must make major changes in diet, and sufficient variety is provided for a person from any cultural context or preference to find foods they are comfortable with and find acceptable.

The above referenced patents are the result of the desperate search to find concentrated forms of the foods in enough variety to feed the children the quantities of carbohydrates they needed before their overall health declined further and they developed sensitivities to the few foods they could eat.

Since these limited numbers of carbohydrates are the sole carbohydrate sources in a diet of only the most well-tolerated foods, providing them as complete nutritionally as possible is essential. Again this is accomplished only by the foods of the above referenced patents. The inclusion of all of the 'non-farinaceous substance' ensures that all of the soluble substances and nutrients contained therein are included in each product. Starch only products lack the nutritional components essential for diets that rely on roots only.

This investigator has discovered then, that just as there are a set of foods that are the most poorly tolerated, and a food allergic or food sensitive person is most likely to react to, namely,—wheat, corn, soy, milk, eggs, and peanuts, there is a set of the most well tolerated foods. These most well tolerated carbohydrates are: tropical root crops including white sweet potato, cassava, malanga, Dioscorea yam, lotus, water chestnut, and arrowroot, other edible roots within the same taxonomic families, and other tropical roots listed in the embodiments below.

This investigator then began to use these foods in research on dietary intervention with very challenging cases, person suffering from a large number of food allergies, sensitivities and intolerances, who experience symptoms ranging from moderately severe to slight and subtle and difficult to recognize, depending on the food, and who also experience a wide range of symptoms from multiple chemical sensitivities, pollens, molds, and anxiety.

The tropical roots as products providing concentrated calories, variety to suit any preference, and providing the full nutritional value of the roots, formed the main stay of the diet.

The tropical roots were the core component of the diet because the RDA's recommend large quantities of carbohydrates, and small quantities of protein (generally 60 or fewer grams) or fats (generally 90 or fewer grams).

This investigator then devised a dietary intervention strategy based on the following principles:

1) well-tolerated carbohydrates only in the diet, thus tropical root crops in the concentrated, complete forms described in the above referenced patents and in a second embodiment additional tropical root crops in concentrated forms described herein.
2) seven day rotation diet
    a) seven days selected because most foods require 4 days for elimination, thus a 3 day period in which the food is not present in the body
    b) seven days is easier to establish a routine because it matches the days of the week
    c) foods on each day stay within the same food families, i.e., any foods taxonomically from the same food family are eaten on one day only and not repeated for one week. This ensures that taxonomically similar foods will be eaten only once per week. This investigator has found that this helps prevent new sensitivities from developing.
3) unusual everything else, all other foods. No other foods included in the diet that the person has eaten more than once or twice a year, and no food included even if rarely eaten that an individual has experienced a reaction from. Although these foods may not be as universally well-tolerated as the carbohydrates, they are foods that the immune system has not been exposed to before, and hence are far less likely to experience reactions to many of the foods.
4) Very few foods included in the diet. Each day only one tropical root based carbohydrate, one unusual meat, one unusual oil or other fat source, and 1-3 unusual vegetables. This relatively few foods per day in which the large majority are essentially universally well tolerated, presents a diet in which if any, will include a very few problem foods. This makes accurate assessment and evaluation of a subjects responses and daily changes possible, because the reactions to foods are now few.
5) Following the Recommended Daily Allowances (RDA)'s for carbohydrates, fats and proteins to ensure that optimal nourishment is achieved. Optimal caloric intake helps greatly avoid the problems of developing sensitivities to new foods and experiencing escalations in severity of symptoms. The balance of carbohydrate, fats, and proteins is optimal when the Recommended Daily Allowances (RDA)'s are followed for carbohydrates, fat, and proteins. On this diet the individual experiences the optimal balance of these food categories, and this optimal balance, generally achieved for the first time in the individual's life, also promotes healing of injured tissues and improvement of health in general.
6) In addition, specify the following for foods:
    a) Uniodized sea salt to avoid corn or starch additives
    b) Distilled water, and broths of foods of the diet only
    c) No dried products such as dried herbs, teas and the like
    d) No canned products
    e) Other than the carbohydrates described above, all vegetables provided fresh and all meats provided fresh or frozen.
7) Complete elimination of all supplements including enzymes, except mineral calcium. This is necessary because the supplements, digestive aids, and so forth contain, are derived from, or are grown in cultures containing the foods intentionally omitted from this diet. The presence of these items would make accurate assessment virtually impossible.

8) No smoking, drinking, recreational drugs, permitted. These substances can cause strong reactions in sensitive individuals, and can cause such a high level of symptoms that the fluctuations in patterns due to other factors are insignificant in comparison are thus not distinguished well enough to discern.

9) In addition specify the following for pharmaceuticals:
   a) Avoid non-essential pharmaceuticals
   b) Any pharmaceutical products retained as essential are provided as active ingredient only from a compounding pharmacy, and provided as pure powder, diluted in distilled water, or diluted in the carbohydrate flour of the day
   c) The active ingredient pharmaceuticals are then included on a daily basis to provide a non-fluctuating pattern of any symptoms they may cause.

10) Without much discussion, so as to avoid inserting a bias as much as possible, reduce chemical exposures as follows:
    a) Drink and cook with distilled water only.
    b) Remove all scented products.
    c) Use only unscented personal care products such as shampoos and deodorants.
    d) Eliminate all non-essential products.
    e) Use only non-colored, non-scented soaps, detergents and cleaning products
    f) Spend as much time in the fresh air as possible; essentially spending waking hours outside.

Figure 1:
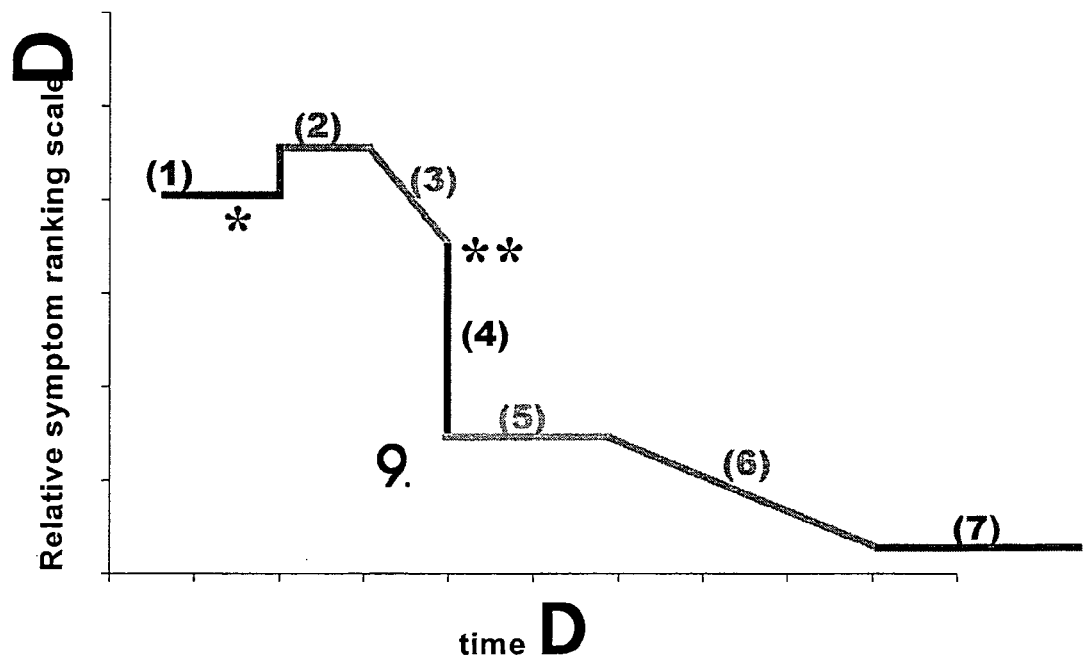
FIG. 1 is a graph showing recovery patterns in autistic individuals.

This investigator has found that the diet was highly effective for foods. The relatively few foods included on the diet, the fact that virtually all of the foods on the diet are well tolerated, and the reductions in other possible exposures, simplify the symptom array, even in the most complex cases until now it is possible to correctly evaluate any symptom fluctuations an individual may report and make accurate cause and effect assessments.

Because a food is only eaten once each week, it generally takes 5-10 weeks for the food assessment to be completed and adjustments to the diet complete that eliminate any and all problem foods.

At this point the person is entirely symptom-free of all food-related problems and unless there are other factors present is ready for diet expansion.

This investigator has confirmed the accuracy of the direct challenge method of food testing when used in conjunction with the above dietary intervention approach. In prior instances, in which the complexity of attempting to test in a context of many food reactions occurring at various levels simultaneously, it was not possible to accurately interpret observed symptoms. In the instant invention, for an individual with only food sensitivities and allergies, who now has no reactions, it is possible to identify and characterize even the most subtle reactions, since the individual now is symptom-free, i.e., has a zero-symptom baseline. Dietary intervention can proceed at the discretion of the health practitioner, who can test a variety of foods, beginning with those believed to be most likely to also be well-tolerated. There is no need to try the food separately since the other foods cause no symptoms. The subject simply eats a large portion of the test food along with other foods at a mealtime.

All food challenges that show no symptoms after about 4 days can be immediately added to the diet, on a day that is taxonomically appropriate. In other words, any food to be added must be added to the day that other foods in the same food family are found. For example if pears are found to cause no symptoms, then pears would be included on the same day as rose hips since they are both taxonomically located in family Rosaceae. The foods may be added to the diet, as would probably be the case for the fruit above, or may be substituted for a food, as for example, should potatoes also cause no symptoms, replacing one of the original tropical root carbohydrates with potatoes. Such a substitution must be done keeping the carbohydrate quantities in mind, since the large quantities of potatoes would be the same as that required for any of the tropical roots.

The foods are tested at the rate of 1 food every four days. Should a reaction occur, that food is eliminated from further consideration, and the individual waits until all symptoms completely subside plus one day, before trying another food.

If the subject has already experienced symptoms associated with some foods prior to beginning the diet, all such foods should be excluded from the testing schedule. The purpose of the careful testing is to identify other foods in addition to the original foods on the diet that an individual can tolerate, and include these well-tolerated foods in the final expanded, symptom-free diet. Finding the set of foods that an individual can eat freely, without symptoms achieves amazing improvements in health for a person, but this achievement alone does not mean that the individual has recovered from his food allergies, sensitivities and intolerances, and is cured. The individual is merely symptom-free because the person is able to completely avoid the foods that make the person ill.

Should the subject return to the old eating patterns, the old symptoms and associated chronic illnesses will also return.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described. This testing setting achieves 100% accuracy in results.

DELAYED SYMPTOMS: For individuals who are experiencing symptoms from other factors as well as foods, the preferred approach is to delay testing until the other factors are identified and eliminated. Because only then is the symptom-free baseline achieved.

THE INSTANT METHOD FOR MULTIPLE CHEMICAL SENSITIVITIES: stop searching for tests that identify problem chemicals, and rely on the simplified symptom patterns achieved as a result of the above dietary intervention strategy, to conduct accurate assessments of patient reported symptoms and circumstances.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described, and then becomes 3) a setting in which simplified symptoms and knowledge that food as a factor is completely eliminated, makes it possible to accurately conduct cause and effect associations for chemical exposure as they are related by the subject.

The above described procedure for conducting dietary intervention is so accurate, rapid and complete, that it is useful as a methodology and a tool for further diagnosing and identifying other problems. One of these is multiple chemical sensitivities. When present, and this investigator has found that these sensitivities are frequently present in individuals experiencing food sensitivities, the subject begins to report symptoms and circumstances attributable to chemical sensitivities as soon as the diet is clear of problem foods and occasionally before the diet assessment is complete.

As described above, as the diet begins the subject is asked to remove all scented products from the home and to substitute unscented products, to drink distilled water only, to spend as many hours outdoors as possible and to quit smoking, drinking alcoholic beverages and the like. The purpose for this is two-fold. First it simplifies the symptom patterns and makes it easier for the subject to accurately describe what is being experienced, and makes it possible for accurate cause and effect assessments to be made regarding foods even if the subject also experiences many chemical sensitivities. Second, after the food assessment is complete and no further food-related symptoms are occurring; the simple changes are a vital part of accurate assessments of multiple chemical sensitivities.

The focus of the program is initially foods, and the subject is never advised when the focus shifts to chemical sensitivities. This is done to avoid introducing a bias into the process.

Because the individual is spending time outside, is not around scented products and cigarette smoke much of the time, there are created blocks of time in which the exposure patterns are greatly altered. No longer is there the constant, unchanging exposures that contribute to a relatively static set of symptoms. Instead, at the time that all food-related symptoms and the previously present relatively static set of symptoms are eliminated, the exposures to other substances are dramatically altered and greatly reduced. It really is like cutting down most of the forest, so one can see the rest of the trees clearly.

The subject is asked to describe what they are experiencing and the symptoms are rated as always. But now, the subject reports, 'The baby was fine until the polyester fleece of her coat touched her face and the back of her neck. Then the skin in only these areas became angry red and erupted into hives.' It is now possible to talk about the composition of the fleece, the age of the coat, any finishing chemicals that may have been used on the fabric, and the child's response to other polyester fabrics. Accurate assessment of the problem, identifying the solution and accurate extrapolation to other circumstances is now possible. The earlier reports of the subject, 'The baby has eczema all over, all of the time, screams all the time, and never sleeps unless I hold her.' Are accurate but not clear enough to allow correct associations and effective problem solving to take place. This is due to the fact that the baby is experiencing reactions to so many things that it was impossible to identify anything accurately.

Once foods are completely eliminated as a factor, the symptom patterns are sufficiently reduced to enable accurate assessments, and the program becomes a powerful tool for assessing problems in other areas. This is essentially a subject-directed process.

In other words, instead of a professional saying 'I think you have _____', and making blanket recommendations that will help if the professional has guessed right. The professional is able to listen to the descriptions of the subject, and easily make accurate cause and effect associations.

If chemical sensitivities are present, they will become obvious as the subject reports how symptoms have changed over time. Now in the absence of all food-related symptoms, food will not be considered, and the choices are among chemical sensitivities, pollens, and mold. This alone is a great aid in assessment.

The subject in subsequent appointment is asked simply to describe his or her day. The subject will recall the things he or she found were more notable each day or during the last week or two. In the description, the subject will tend to emphasize the circumstances that were the most difficult, troublesome or serious. Thus by simply asking opened question, and going over symptoms, the symptoms and associated sensitivities that are the most serious and also most easily identified will be described by the subject.

In other words, after foods, the emphasis is placed on what is next most bothersome. At this time the subject invariably reports symptoms associated with multiple chemical sensitivities as the next most bothersome problem, whether aware of this prior to starting the diet or not. In other words, because the patient merely reports what they have experienced, prior knowledge is unimportant. Some persons are surprised to realize that they are experiencing symptoms associated with chemical sensitivities, and some are dismayed. One mother replied, 'I decided my child will not have chemical sensitivities' to which the reply was, 'This is not about what you, your child, or I want; it is about accurately identifying what your child is experiencing symptoms from. If your child experiences symptoms associated with chemical exposures, she experiences symptoms associated with chemical exposures. All that one can do is make accurate cause and effect associations. You reported that your child was symptom-free until you took her to a building stocked with paints, solvents and pesticides, and within one minute she was glassy-eyed, mute, and unable to comprehend anything said to her. You further reported that this lasted for 8 hours after leaving the building, after which time she returned to completely normal. And finally that this happened in the same pattern twice. This is clearly strong evidence that something in the building caused your daughter to experience the reported effect, which to your knowledge occurred no other time. This is strong cause and effect information. Ignoring the likely association will not alter what your daughter actually experiences.'

It was not difficult to correctly interpret the change in the child described above; however, in the beginning of the program, the child was essentially as described all of the time (glassy-eyed, mute, and unable to comprehend anything said to her) and it was completely impossible to notice any difference in the child whether in the above described building or not.

As the subject describes the symptoms, changes and events that have occurred, it will not initially be possible to accurately identify all of the exposures and their associated symptoms. However, it is possible to correctly interpret the most obvious; the one generally causing the strongest response.

The practitioner identifies what is possible to associate, and recommends avoidance strategies for one or two of these obvious ones. If the cause and effect assessment is correct, the associated symptoms should be correspondingly reduced. If this proves to be the case, then that is taken as evidence that the assessment was correct.

The practitioner then applies the avoidance strategy broadly to all other circumstances in which the subject would be exposed to that substance or to similar substances. Total avoidance of that level of exposure, completely eliminates the immediate exposure that the subject reported and also eliminates symptoms that would be associated with all other similar exposures but which happen to be less easy to discern. By broadly applying the causes and effect associate it is possible to correctly interpret, the practitioner is able to make recommendations that greatly reduce the level of symptoms and make accurate reporting, identification and assessment of the remaining sensitivities simpler and easier.

In the case of one child, for example, the child was found to be sensitive to plastic materials. Once this was clearly established by removing one plastic item that he carried with him always, then all plastic materials were removed from the home, and the child experienced dramatic improvements.

The subject remains in his/her home environment throughout the program, and changes are made as they become apparent to all. Since this occurs directly associate with what the patient is reporting, no unnecessary changes are made and no unnecessary expense is incurred. In general, if a change is necessary, the efficacy of the change is tested before the money is spent.

This process is repeated over and over, until no further reactions are being reported; and only those changes that are necessary are made. For example no avoidance to plastic materials is recommended unless the patterns associated with the reports of the subject clearly indicate that plastic sensitivities is an important concern. Therefore some individuals are directed to install chlorine filters on their showers and others are not.

The point is that once food is eliminated as a factor, multiple chemical sensitivities, which are highly individualized problems, can be easily, and accurately assessed and identified and effective solutions can be offered that are tailored to the individual. The approach of applying blanket recommendations to everyone in the hope that some part will help is no longer needed. Persons who experience symptoms associated with chemical sensitivities will be easily identified and this who do not experience symptoms associated with chemical sensitivities will also be easily identified.

Using this method, the health practitioner with appropriate training in environmental chemistry will be able to provide assessments easily, effectively and accurately. This has heretofore not been possible to achieve.

This approach is particularly important and valuable in identifying severe sensitivities that underlie some of the most debilitating chronic disorders. Autistic children frequently suffer from both food allergies and multiple chemical sensitivities, as well as sensitivities to other agents such as mold, pollens and the like. An autistic child suffering from multiple chemical sensitivities typically adjusts and adapts his/her behavior patterns and self stimulating behaviors according the exposures he/she is experiencing. These merge so completely into the fabric of life and daily activities and emerge so gradually that it is impossible to distinguish habit, general or personal preference, autistic behaviors, effects of chemical exposures, and effects of food allergies and sensitivities and effects of other environmental exposures.

Autistic children who suffer from underlying food allergies and sensitivities generally experience intense and abrupt shifts in their symptoms including dramatic drops in pain, sudden and abrupt drop in distress caused by hypersensitivity to sensory stimuli such as noise, motion, light, touch, smell, commotion, and the like, a dramatic drop in emotional outbursts resulting in violent behaviors, screaming fits, tantrums and the like, and the patterns of occurrence of symptoms also change abruptly. As a result their adaptive behaviors also change.

Because the dietary intervention approach described above is highly effective and very rapid, the changes in symptom levels is abrupt and rapid. The swiftness of the changes in symptom levels does not give time for the child to adapt and change the exposure patterns and adapt new ones. The highly sensitive child is essentially without the frameworks and behavioral adaptations that the child has used to adapt to and protect from these problems and at the same time maintain the level of exposure.

Without workable frameworks and behavioral adaptations, it is much easier for the health professional to perform accurate cause and effect associations. Once the initial dietary intervention strategies are complete and the abrupt, dramatic drop in symptom levels occurs, autistic children often begin a series of 'seeking behaviors'. These are intentional efforts on the part of the child to increase the child's levels of exposures and return them back to the previously high levels. This is much like a drug addict's desperate search for drugs as the effects begin to wear off. Seeking behaviors can include:

1) smelling other persons foods, thus re-exposing himself to foods without eating them
2) stealing foods and eating off diet foods
3) licking chairs, counter tops, table tops and floors for small amounts of food residues,
4) abruptly spending large amounts of time in a new activity, that was previously less important, such as spending hours holding glossy books up to his/her face and rubbing the pages against his skin and inhaling deeply, spending large amounts of time playing in the bathtub and drinking the water, becoming intensely interested in mom and dad's socks—feeling them, rubbing them, holding them up to the face for long periods of time, spending large amounts of time playing with, rubbing and smelling plastic toys.

Because the seeking behaviors happen rapidly, abruptly, and intensely in desperate response to the dramatic changes caused by the instant highly effective dietary intervention program described earlier, it is possible to correctly see these changes for what they really are—attempts to increase exposures and re-expose to drastically reduce substances. This is only possible as a result of the rapid and complete elimination of the food-related symptoms in conjunction with the simple chemical reductions described above. When changes are made gradually, the child accommodates with new exposures and altered behavior patterns in such a gradual way that accurate assessments of cause and effect are impossible.

The instant dietary intervention program is thus used as a highly effective diagnostic tool for simplifying and identifying complicated intertwining of symptoms, behaviors and exposures that absent the instant invention of applicant are impossible to accurately unravel.

Once the correct cause and effect association is made, determining the appropriate recommendations and avoidance strategies is relatively straightforward and simple. The first step is confirmation of a particular exposure. For example in the case of the child and the books, the parent is directed to take a book apart and encase each page in a flat cellophane bag, seal the spine with foil, so that no contact with print related fumes or printing ink is possible. The book is then returned to the child to do with, as he likes. If the child plays with and handles the book as before, then exposure to print and fumes was not the issue; however this investigator has never once found this to occur. The child generally picks up the book to play with as normal, not noticing the changes to the book. The child opens the book, places it against his/her face, inhales deeply and starts to flutter his fingers and roll back his eyes. Then suddenly, with a startled look, the child looks at the book in surprise, brings it back to his face to sniff deeply again, and when nothing happens again, discards the book in disgust. This is the confirmation that the time spend lovingly caressing books for hours was not a simple autistic action, but an intentional activity on the part of the subject to increase exposure to a substance and incur the associated symptoms and behaviors.

The second step, which follows confirmation, is to immediately stop the exposure. In the present example, this would involve either removal of the books and directing the child to other activities not causing exposure, such writing stories with a pencil or telling stories, or encasing all books the child has access to in cellophane.

The third step involves broadly applying the observed exposure. All of the circumstances in which the child would be encounter the same or chemically similar substances would be identified and the health professional would work with the parents to develop effective avoidance strategies for the child. Thus from one specific instance, accurately interpreted and confirmed, it is possible to identify a much large number of circumstances in which similar exposures would occur, and also take steps to avoid these exposures.

In so doing a large array of exposures and more subtle symptoms, individually not possible to identify, can be eliminated. The result is a further dramatic reduction in the overall level of symptoms.

This also has the effect of simplifying the remaining patterns of chemical sensitivities as yet unidentified. Therefore as each cause and effect association is made, confirmed, and broadly applied, it becomes increasingly easier to identify any remaining sensitivities. The subject simply proceeds through his or her daily activities minus the exposures that have already been identified and describes what he experiences to the health professional. With each successive identification and elimination cycle, the overall symptom baseline drops and it becomes possible to discern increasingly more subtle effects.

Although less important in that they are not life threatening, subtle effects are sometimes the only readily identifiable symptom that is a part of a broader symptom pattern. For example chronic disorders such as arthritis often do not follow rapid, dramatic fluctuations in symptom levels because the pain and inflammation occur in tissue that is more slowly affected by substances circulating in the blood. The symptoms associated with arthritis may be slow to increase and slow to decrease, with lag times and delays that may involve days or weeks. Specific, accurate identification of causative agents may unclear. Fortunately, however, exposure to foods and chemicals almost always causes an array of responses that form a fingerprint like pattern of symptoms that is unique to each substance. Included in virtually every array are subtle effects, some of which may even seem silly that the subject could easily live comfortably with. By developing exposure strategies that eliminate exposures to subtle or inconsequential symptoms that can definitely be correlated with a certain food or exposure, it is possible to eliminate symptoms associated with a chronic, serious disorder. Since the underlying problem was never the focus, the longer term, more difficult cause and effect associations may never be known. By emphasizing instead on the subtle effects that can be discerned, the overall disorder to which they are linked is eliminated.

For example, a woman suffering from arthritis underwent the above described dietary intervention program. In addition to arthritis she suffered from muscle spasms and outbursts of uncontrolled bawling. In the consultations with the subject over a period of several months, the symptoms that could be more easily observed were noted, such as muscle spasms and outbursts of bawling. It was found that the subject was sensitive to gas heat, and chlorine and other compounds found in drinking water and particularly released during showers. The subject switched to electric heat, installed a water filter for the chlorine and halogenated organic compounds, and slept next to a window open a few inches. As a result of these changes the woman no longer suffered from the muscle spasms and the outbursts of bawling. At this time it was realized that the arthritis-related symptoms were also gone, but no specific substances had been identified that were specifically and directly associated with this persons arthritis.

In another example, a man suffering from Alzheimer's disease underwent the above described dietary intervention program. After the initial emphasis on diet, when the diet consisted only of well-tolerated foods, chemical sensitivities became apparent. Only because food-related symptoms were completely eliminated through the instant method of Applicant was it possible to accurately identify and develop avoidance strategies for multiple chemical sensitivities.

The subject was mute, did not recognize or respond to others and did not indicate an awareness of where he was. The methodology as was described above for the subject with arthritis. The focus was not on the Alzheimer's disease at all, but on the identification of and cause and effect associations with the fluctuating symptoms for which correct cause and effect associations could be made. The subject had a large purple area on the back of one hand, the subject's wife noted this area was sometimes larger and sometimes smaller, sometimes darker in color and sometimes lighter. The purple area on the subject's hand was one of the fluctuating symptoms that this investigator was able to associate with chemical sensitivities. Other aspects that were found to be useful included noting the exposures associated with activities that the subject was spending a great deal of time with, such as many hours watering plants and gardens and running his hands through water (chlorinated water), many hours spent looking at glossy magazines (printing inks, printing solvents, and treated paper), noting his preferences for certain synthetic objects, many hours holding a ball. By careful assessment of observations reported by the wife, these sensitivities and sensitivities to volatile organics were found to be a problem, and appropriate guidance was given.

As the exposures were eliminated to substances that could be clearly identified as causing the subject to experience symptoms, even if those symptoms were in themselves insignificant, it was possible to provide the expected relief from the symptoms that could be directly associated. In addition, there was a significant, impressive improvement in the symptoms of Alzheimer's disease in this subject, even though the disease itself was not the direct focus. After only three months, the subject knew where he was, recognized his wife, his son, relatives he had not seen in over a year, and even his Alzheimer's physician, who nearly fell over. The subject saw the physician across the room, pointed him out to his wife, and said, 'There he is!' smiled and waved.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described, and then becomes 3) a setting in which simplified symptoms and knowledge that food as a factor is completely eliminated, makes it possible to accurately conduct cause and effect associations for chemical exposures as they are related by the subject, and then causes 4) such a dramatic, abrupt reduction in symptoms that an individuals' attempts to compensate for the abrupt drop in these exposures can be accurately observed and interpreted making it possible to rapidly and accurately identify additional allergies, sensitivities and intolerances that otherwise would be unable to discern, and in addition provide 5) .a setting in which overall symptom picture is clear enough and simple enough that accurate cause and effect associations can be made for subtle symptoms and effects that would otherwise be completely unrecognizable, and that are 6) often associated with very important major chronic diseases, these diseases themselves being not possible often to otherwise associate with their underlying causes.

THE INSTANT METHOD FOR ALLERGIES AND SENSITIVITIES TO POLLENS, MOLDS: in addition to tests that identify allergies to pollens and molds, rely on the simplified symptom patterns achieved as a result of the above dietary intervention strategy, to conduct accurate assessments of a previously unrecognized wide array of symptoms associated with sensitivities to pollens and molds.

The above described procedure for conducting dietary intervention is so accurate, rapid and complete, that it is useful as a methodology and a tool for further diagnosing and identifying other problems. One of these is sensitivity to pollens and molds. This investigator has found that through the use of the above described method, symptoms not previously associated with exposure to mold and pollen can be accurately identified and associated with exposure. When present, the subject begins to report symptoms and circumstances attributable to molds and pollens as soon as the diet is clear of problem foods and occasionally before the diet assessment is complete.

Once foods are completely eliminated as a factor, the program becomes a powerful tool for assessing problems in other areas such as pollens and molds as essentially a subject-directed process.

If mold sensitivities are present, the associated symptoms will become obvious as the subject reports how symptoms have changed over time. Now in the absence of all food-related symptoms, food will not be considered, and the choices are among chemical sensitivities, pollens, and mold. This alone is a great aid in assessment.

The subject in subsequent appointment is asked simply to describe his or her day. The subject will recall the things he or she found were more notable each day or during the last week or two. In the description, the subject will tend to emphasize the circumstances that were the most difficult, troublesome or serious. Thus by simply asking opened question, and going over symptoms, the symptoms and associated sensitivities that are the most serious and also most easily identified will be described by the subject.

In other words, after foods, the emphasis is placed on what is next most bothersome. At this time the subject may report symptoms associated with pollen and mold sensitivities simultaneously with multiple chemical sensitivities, or if more severe, the symptoms to mold and pollens will be reported first. The patient is generally unaware that symptoms other than those conventionally associated with pollens and molds may occur.

For example, a subject suffering from multiple sclerosis underwent the above described dietary intervention program, her symptoms related to multiple sclerosis disappeared and she went into remission. A few months later, she reported sharp pains in the eyes and further reported that she had lost her sight each spring for the past five years. This investigator was able to associate the blindness with exposure to springtime tree pollen. The subject was provided with techniques to eliminate exposure to pollens to implement immediately. As soon as the subject implemented the recommendations, the pain went away and for the first spring in 5 years the subject's eyesight remained unaffected during the spring, and each subsequent spring. In this subject exposure to springtime pollens was causing her temporary blindness; it was impossible to accurately conduct accurate cause and effect assessments until the subject underwent the above described dietary intervention program and her other multiple sclerosis symptoms were eliminated. In the absence of other symptoms, the continuing of the springtime pattern became easily identified and eliminated.

In another example a 40 year old woman suffering from severe diarrhea, fatigue, and shortness of breath underwent the above described dietary intervention program of applicant. Within about 8 weeks all of the subject's symptoms had been relieved. Several months later, starting in mid-August, the symptoms of severe diarrhea, fatigue, and shortness of breath began to reappear, becoming very intense during the first two weeks in September in spite of the fact that the diet was unchanged in anyway. Knowing that food was not a factor, this investigator noted the pattern paralleled precisely the ragweed pollen season in the subject's area, and recommended procedures for completely avoiding exposure to pollens. The subject, within a few days of implementing these recommendations, became symptom-free again. The instant dietary intervention approach of applicant makes it possible to clearly associate symptoms associated with pollen exposure that are previously unknown and unrecognized in the Art. This is due to the fact that these pollen-related effects can now be clearly seen in the absence of symptoms from other factors such as foods and multiple chemical sensitivities.

In an example of the effectiveness of the instant invention in diagnosing unusual and unexpected symptoms associated with exposure to pollens, an 8 year old child suffering from PDD and autism was spending great amounts of her day jumping, hand flapping and spinning endlessly in circles. These behaviors were eliminated when the child underwent the above described instant dietary intervention program of Applicant. The child was calm and serene, and proceeded normally through her days after the last problem food was removed form the diet. This continued for approximately one week. On the seventh day, the child went outside to play on a playground and immediately returned to her hand flapping, jumping and spinning behaviors. This investigator noted that there had been an abrupt rise in springtime pollens and recommended highly effective pollen avoidance procedures, which the parents implemented immediately. Within a few days, the child's behavior returned to normal and remained normal, until the child began active, intentional mold-seeking activities described below.

In an example of the effectiveness of the instant invention in diagnosing unusual and unexpected symptoms associated with exposure to mold, the above 8 year old child suffering from PDD and autism who was initially spending great amounts of her day jumping, hand flapping and spinning endlessly in circles, experienced the elimination of these behaviors when the child underwent the above described instant dietary intervention program of Applicant. The child was calm and serene, and proceeded normally through her days after the last problem food was removed form the diet. Following the reemergence of jumping, hand flapping and spinning behaviors, treatment for pollen sensitivities, implementation of effective avoidance strategies, and re-elimination of jumping, hand flapping and spinning behaviors described above, a new problem was observed.

Approximately one week after the implementation of pollen protection procedures, the child began displaying the spinning behaviors again. This time the behaviors occurred only in one part of an upstairs hallway in the home. The child had suddenly started spending many hours in this one location and was spinning there for hours at a time. The family accepted this as part of her normal autistic behaviors and thought it was simply normal for her.

When discussed with the Applicant, it was readily apparent that this was a new 'seeking' behavior. The parents were sent to examine the area closely and reported that the child was sitting on and spinning on a large, damp water spot area of the hallway, that lay immediately beneath a water damage area from a leak in the roof of the home. This investigator provided the parents with specific instructions for correcting the leak without introducing new problems, such as new chemical exposures, for the child, and until the repairs were made, the child was removed from the vicinity. Once repairs were completed, the child was allowed to return to the area and the home without restriction or limitation.

After an initial return to the area, the child made a spin or two on the location of the old spot, looked a little stunned and disappointed, and then looked a little confused as if she was wondering why she was trying to spin around in the hallway, got up and went to play in other places. The jumping, hand flapping and spinning behaviors were now completely eliminated and did not return. The final direction to the family, then, was direction to similarly identify and remove any other moldy areas of the home, and to prevent her from spending time in moldy areas such as barns, dark, dank, heavily shaded areas, mulch, basements and the like.

The accurate identification and association of self stimulating behaviors with exposure to moldy areas was a critical component of achieving a full and complete recovery from autism for this child. This assessment would not have been possible absent the instant approach of applicant.

This investigator has found very little difference in many cases between symptoms associated with foods, symptoms associated with multiple chemical sensitivities, symptoms associated with pollens, and symptoms associated with molds. This investigator using the instant invention has been able to accurately associate symptoms including but not limited to the following accurately with exposure to chemicals, pollens and/or molds in various individuals including but not limited to: diarrhea, constipation, nausea, headaches, seizures, trance-like, dazed state, violence, aggression, lethargy, a wide variety of emotions, eczema, rashes, bloating, cramps, muscle spasms, vomiting, swelling, itching, flushed face, paleness, fatigue. For this reason, absent the instant invention of applicant, it is virtually impossible to accurately attribute the causes and effects for each individual.

The picture is further complicated by the fact that each individual responds to particular exposures in unique, individual ways. For this reason, the instant method, of applicant is absolutely essential to identify the unique responses of a subject. Only then can effective avoidance strategies be prepared. When each person and circumstance is different, when each individual's response is different, then a highly logical methodology, a procedure, which makes possible accurate identification of each individual's responses to various exposures becomes the only way that can provide effective assistance to the individual and lead to relief from symptoms. Attempts by other investigators led to inaccurate assessments and ineffective recommendations, because they lacked the thorough method of applicant.

The abrupt changes in symptoms patterns associated with complete elimination of all problem foods and the above describe partial elimination of chemical exposures, simplifies the total symptom picture sufficiently to make it possible to accurately distinguish among chemicals, pollens and molds, correctly associate the correct exposure with the appropriate symptoms, and only then can one describe the appropriate avoidance strategies.

The previous, ineffective approach of the Art, which involves applying blanket recommendations to everyone in the hope that some part will help, is no longer needed. Persons who experience symptoms associated with pollens and molds will be easily identified and those who do not experience symptoms associated with pollens and molds will also be easily identified. Prior to the instant invention of applicant, the above-described symptoms were not associated with exposures to pollens and molds. This has heretofore not been possible to achieve.

This approach is particularly important and valuable in identifying severe sensitivities that underlie some of the most debilitating chronic disorders. Autistic children frequently suffer from both food allergies, multiple chemical sensitivities, and sensitivities to mold, pollens and the like. An autistic child typically adjusts and adapts his/her behavior patterns and self stimulating behaviors according the exposures he/she is experiencing. These merge so completely into the fabric of life and daily activities and emerge so gradually that it is impossible to distinguish habit, general or personal preference, autistic behaviors, effects of chemical exposures, and effects of food allergies and sensitivities and effects of other environmental exposures.

Autistic children who suffer from underlying food allergies and sensitivities generally experience intense and abrupt shifts in their symptoms including dramatic drops in pain, sudden and abrupt drop in distress caused by hypersensitivity to sensory stimuli such as noise, motion, light, touch, smell, commotion, and the like, a dramatic drop in emotional outbursts such as violent behaviors, screaming fits, tantrums and the like, and the patterns of occurrence of symptoms also change abruptly. As a result their adaptive behaviors also change.

Because the instant dietary intervention approach described above is highly effective and very rapid, the changes in symptom levels are abrupt and rapid. The swiftness of the changes in symptom levels does not give time for the child to adapt and change the exposure patterns and adapt new ones. The highly sensitive child is essentially without the frameworks and behavioral adaptations that the child has used to adapt to and protect from these problems and at the same time maintain the level of exposure.

Without workable frameworks and behavioral adaptations, it is much easier for the health professional to perform accurate cause and effect associations. Once the initial dietary intervention strategies are complete and the abrupt, dramatic drop in symptom levels occurs, autistic children often begin a series of 'seeking behaviors'. These are intentional efforts on the part of the child to increase the child's levels of exposures and return them back to the previously high levels. This is much like a drug addict's desperate search for drugs as the effects begin to wear off. Seeking behaviors can include:

1) Licking moldy areas of window panes and licking mold from doorjamb,
2) Climbing behind major appliances to lick, eat or handle the moldy components,
3) Abruptly spending large amounts of time in a new location, such as spending hours in a moldy area of a hallway in preference to all non-moldy areas.

Because the seeking behaviors happen rapidly, abruptly, and intensely in desperate response to the dramatic changes caused by the instant highly effective dietary intervention program described earlier, it is possible to correctly see these changes for what they really are—attempts to increase exposures and re-expose to drastically reduced substances. This is only possible as a result of the rapid and complete elimination of the food-related symptoms in conjunction with the simple chemical reductions described above. When changes are made gradually or only a few changes are made, as occurs absent the teachings of Applicant, the subject accommodates with new exposures and altered behavior patterns in such a gradual way that accurate assessments of cause and effect are impossible.

These seeking behaviors dramatically indicate sensitivities of the subject that otherwise are expressed in such subtle patterns and arrays that cause and effect associations are not possible to make. Only in the instant invention of applicant do the abrupt behavioral changes occur. Thus only in the instant invention of applicant is it possible to make these vital cause and effect associations.

In the above instances and in all similar cases, the health professional is then able to recommend avoidance strategies for the entire category of exposure represented by the behavior. The results in another drop in the overall symptom patterns of the individual.

Each of the behaviors listed above is the behavior of a different subject. Each of these behaviors were very mild and sporadic or did not occur at all prior to beginning the instant program of applicant. Similarly, it was initially impossible to tell from the complex array of symptoms that sensitivities to pollens and molds contributed in any way to the problems of these autistic children. These and similar patterns are most clearly seen in individuals experiencing severe neurological effects and disorders, such as autism, PDD, Aspergers syndrome, hyperactivity, Alzheimer's disease, seizure disorders, and the like.

The instant dietary intervention program is thus used as a highly effective diagnostic tool for simplifying and identifying complicated intertwinings of symptoms, behaviors and exposures that absent the instant invention of applicant are impossible to accurately unravel.

Once the correct cause and effect association is made, determining the appropriate recommendations and avoidance strategies is relatively straightforward and simple. The first step is confirmation of a particular exposure. For example in the case of the child licking the moldy windows, the parent is directed to thoroughly clean and dry the window with peroxide, thorough water rinses (chosen to avoid introducing organic chemicals). The child is then allowed to play anywhere and anyway without direction or intervention, and the child is observed. If the child licks, interacts with and plays with the window as before, then exposure to mold was not the issue; however this investigator has never once found this to occur. The child returns to the window as normal, not noticing the absence of dirt and mold. The child licks the window, places his/her face against the window, inhales deeply and starts to engage in his/her self stimulating behaviors. Then suddenly, with a startled look, the child looks at the window in surprise, gets back up close to lick, rub and sniff deeply again, and when nothing happens again, leaves the window in disgust. This is the confirmation that the time spent licking windows for hours was not a simple autistic action, but an intentional activity on the part of the subject to increase exposure to a substance and incur the associated symptoms and behaviors.

The second step, which follows confirmation, is to immediately stop the exposure. In the present example, this would involve thorough cleaning of all windows and other areas the child has been licking.

The third step involves broadly applying the observed exposure. All of the circumstances in which the child would be encounter levels of mold above ambient concentrations would be identified and the health professional would work with the parents to develop effective avoidance strategies for the child. Thus from one specific instance, accurately interpreted and confirmed, it is possible to identify a much large number of circumstances in which similar exposures would occur, and also take steps to avoid these exposures.

In so doing a large array of exposures and more subtle symptoms, individually not possible to identify, can be eliminated. The result is a further dramatic reduction in the overall level of symptoms.

This also has the effect of simplifying the remaining patterns of sensitivities as yet unidentified. Therefore as each cause and effect association is made, confirmed, and broadly applied, it becomes increasingly easier to identify any remaining sensitivities. The subject simply proceeds through his or her daily activities minus the exposures that have already been identified and describes what he experiences to the health professional. With each successive identification and elimination cycle, the overall symptom baseline drops and it becomes possible to discern increasingly more subtle effects.

An example of this seeking behavior is provided in the case of a 3 year old autistic child. In this case the seeking behavior was cleverly disguised as a preference, and is a good example of a seeking behavior that is both abrupt and obvious and also subtle and easily missed. Before beginning the approach of the instant invention, the subject suffered from eczema, hyperactivity, violence and bizarre behaviors such as sucking on carpet, tracing hard lines of objects, poking objects down his throat, and he was socially unresponsive. After the implementation of the instant dietary intervention program these severe symptoms were eliminated and his behavior and symptoms became normal.

Within a week, however, one of the behaviors began to return and there were subtle indications that the child was not doing quite as well. The child began to be very interested in 'lines'. He spent many hours 'lining'. The 'lining' behavior involved walking to an object with an edge and bending down so that he could look along the length of the line, and then the child proceeded to walk along the entire length of the line.

The parents described this behavior as just a very minor manifestation of his autism. This investigator began to question closely. 'Did the child walk along the length of every line? If not, then which ones? Dry steps in bright sunlight? Steps in dank, overcast areas? Lines etched into a sunlit plaza? Along fences? Along hedges? The parents realized that he did not 'line' indiscriminately, but was selecting only damp, dank lines and bushes and shaded wooden fences. Parents were advised to keep the child away from moldy areas, and the behavior disappeared immediately as well as the other subtle regressions.

In this child's case, he was strongly seeking new exposures to compensate for the old exposures; however, the behaviors were minor in comparison to the prior problems and the child was able to disguise the behavior in such a way that the parents were unable to recognize it for what it was. This behavior white sweet potato shreds the first indication of the existence of a severe mold problem for this child that was a major cause of his autistic behaviors. Absent the instant invention of applicant, this problem and the associated behaviors would have been impossible to discern.

Although less important in that they are not life threatening, subtle effects are sometimes the only readily identifiable symptom that is a part of a broader symptom pattern. For example chronic disorders such as arthritis often do not follow rapid, dramatic fluctuations in symptom levels because the pain and inflammation occur in tissue that is more slowly affected by substances circulating in the blood. The symptoms associated with arthritis may be slow to increase and slow to decrease, with lag times and delays that may involve days or weeks. Specific, accurate identification of causative agents may unclear. Fortunately, however, exposure to molds almost always causes an array of responses that form a fingerprint like pattern of symptoms that is unique to each substance. Included in virtually every array are subtle effects, some of which may even seem silly that the subject could easily live comfortably with. By developing exposure strategies that eliminate exposures to subtle or inconsequential symptoms that can definitely be correlated with a certain food or exposure, it is possible to eliminate symptoms associated with a chronic, serious disorder. Since the underlying problem was never the focus, the longer term, more difficult cause and effect associations may never be known. By emphasizing instead on the subtle effects that can be discerned, the overall disorder to which they are linked is eliminated.

In another example, a man suffering from Alzheimer's disease underwent the above described dietary intervention program. After the initial emphasis on diet, when the diet consisted only of well-tolerated foods, chemical sensitivities became apparent. Only because food-related symptoms were completely eliminated through the instant method of Applicant was it possible to accurately identify and develop avoidance strategies for mold sensitivities.

The subject was mute, did not recognize or respond to others and did not indicate an awareness of where he was. The methodology as was described above. The focus was not on the Alzheimer's disease at all, but on the identification of and cause and effect associations with the fluctuating symptoms for which correct cause and effect associations could be made. In this example the only clue was that the subject enjoyed spending large amounts of time digging in the flower beds, and was especially eager to participate when mulch was applied to flower beds. His wife reported that he was eager to handle the mulch himself. Following this subtle clue, measures to avoid mold exposure were taken and areas inside the home that smelled moldy and musty were cleaned and corrected. The result was a pronounced improvement in the subject's Alzheimer's related symptoms, such awareness of surroundings, sociability, and his usage of words increased.

As the exposures were eliminated to substances that could be clearly identified as causing the subject to experience symptoms, even if those symptoms were in themselves insignificant, it was possible to provide the expected relief from the symptoms that could be directly associated. In addition, there was a significant, impressive improvement in the symptoms of Alzheimer's disease in this subject, even though the disease itself was not the direct focus.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described, and then becomes 3) a setting in which simplified symptoms and knowledge that food as a factor is completely eliminated, makes it possible to accurately conduct cause and effect associations for chemical exposures as they are related by the subject, and then causes 4) such a dramatic, abrupt reduction in symptoms that an individuals' attempts to compensate for the abrupt drop in these exposures can be accurately observed and interpreted making it possible to rapidly and accurately identify additional allergies, sensitivities and intolerances that otherwise would be unable to discern, and in addition provide 5) .a setting in which overall symptom picture is clear enough and simple enough that accurate cause and effect associations can be made for subtle symptoms and effects that would otherwise be completely unrecognizable, and that are 6) often associated with very important major chronic diseases, these diseases themselves being not possible often to otherwise associate with their underlying causes.

THE INSTANT METHOD FOR RECOGNISING AND ADDRESSING ANXIETY AND OTHER EMOTIONAL ISSUES: rely on the simplified symptom patterns achieved as a result of the above dietary intervention strategy, to recognize a wide array of symptoms associated with anxiety and other emotional issues.

Individuals, particularly adults beginning the instant intervention program of applicant generally have experienced myriad numbers of confusing symptoms that have responded poorly to a wide variety of treatment techniques. They have seen an average of 4 physicians of different specialties, and they have sampled a variety of alternative approaches, generally including environmental physicians, chiropractors and naturopaths. Each of these persons has prescribed a treatment approach with assurances that the approach will solve their problems. These people generally have been told they suffer from allergies, sensitivities and intolerances, multiple chemical sensitivities, Candidiasis, leaky gut, toxic effects from mercury amalgam fillings, pesticides in their tissues that need to be sweated out in daily sauna treatments, enzyme deficiencies and other nutritional deficiencies that require many supplements, enzymes, and the like, all of the above, and then none of the above. Most of these persons have been advised to seek psychological help, which they have generally ignored or tried only briefly with no results.

During the time period, often extending to many years for adults, in which the subject is trying these various therapies, each is tried with great hopefulness that at last the solution has been found and relief is at hand. Unfortunately, the subject has generally been disappointed. The typical pattern is that the subject will experience initial symptom relief, sometimes that relief is impressive, but the relief is temporary. The subject experiences a gradual and disheartening return of symptoms.

As the symptoms return the health provider becomes generally less interested or helpful. This is usually due to the fact that at this point there is much less that the provider has to offer and it is becoming apparent that the patient's problems are not as appropriate for the practitioner's discipline as had been originally thought.

Although this may be appropriate from the standpoint of the health provider, it is devastation from the viewpoint of the patient who finds him/her self feeling repeatedly abandoned and left often to try to determine the next appropriate direction to take on his or her own. After repeated cycles of similar experiences, the subject learns to be wary and less trustful of the health professional, and finds that the preferred path is to believe first in what the subject can observe for him/her self.

Unfortunately the subject, although truly accurate about what he feels and experiences internally, is ill equipped to make accurate cause and effect assessments, and begins to be governed by his/her fears. The fear and anxiety cause new symptoms—heart palpitations, nausea, vomiting, diarrhea, constipation, shortness of breath, tightness of the chest and throat, abdominal cramping. Unfortunately many of these are similar to the symptoms already being experienced by the individual, so they are not recognized as new, but are recognized as 'worse'. The patient simply believes the problems are becoming worse and becomes more frightened, and experiences even more anxiety-related symptoms.

Treatment for anxiety is generally not seen as effective since at best only the anxiety related symptoms are relieved and the patient continues to experience all of the original symptoms, which were significant problems to begin with.

Thus treatment for anxiety alone does not relieve the symptoms caused by food, chemicals, pollens, mold and the like, and treatment for foods, chemicals, pollens, mold and the like does not relieve the symptoms caused by anxiety.

The high accuracy of the instant invention of applicant makes it possible to effectively identify and avoid the symptoms due to foods, chemicals, pollens, mold and the like and simultaneously identify and address the symptoms due to anxiety, fear and other emotions.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described, and then becomes 3) a setting in which simplified symptoms and knowledge that food as a factor is completely eliminated, makes it possible to accurately conduct cause and effect associations for chemical exposures as they are related by the subject, and then causes 4) such a dramatic, abrupt reduction in symptoms that an individuals' attempts to compensate for the abrupt drop in these exposures can be accurately observed and interpreted making it possible to rapidly and accurately identify additional allergies, sensitivities and intolerances that otherwise would be unable to discern, and in addition provide 5) .a setting in which overall symptom picture is clear enough and simple enough that accurate cause and effect associations can be made for subtle symptoms and effects that would otherwise be completely unrecognizable, and that are 6) often associated with very important major chronic diseases, these diseases themselves being not possible often to otherwise associate with their underlying causes, and in addition provides 7) a setting in which the overall symptom picture is clear enough that symptoms associated with emotions, such as fear and anxiety can be accurately identified and addressed through counseling.

Many of the subjects entering the instant program of Applicant are very fearful and anxious. Many also have bizarre beliefs that stem from their attempts to understand their miasma of confusing symptoms. Examples include individuals who are convinced or afraid that:

1) Their body is unable to tolerate any oils
2) Their body is unable to digest any form of protein.
3) Their body is unable to eat any food more that once per day without symptoms.
4) Their body is unable to tolerate any vegetables.
5) Their body is unable to tolerate any form of carbohydrates.
6) Their body is unable to handle any food at all.
7) They fear becoming allergic to everything and dying.
8) They fear being unable to work and being unemployed.

Startling symptoms are generally described, for example immediate abdominal bloating, severe cramping, diarrhea, shortness of breath, and choking sensations.

The instant invention of Applicant is a highly effective tool in these circumstances, for several reasons, 1) the unusual foods of the diet are not ones the individual has eaten before, 2) the patterns associated with symptoms caused by food sensitivities are different from the symptoms caused by fear and anxiety, and 3) because the instant invention is a methodology of discovery that aims to find out and clearly understand and accurately interpret how a person's body works, the individual can be directed toward and participate in the process of discovery, thereby achieving a feeling of control as opposed to helplessness.

If anxiety, fear or other emotional issues are present they generally become obvious early in the instant program of Applicant. For example the program begins with dietary intervention; thus during presentation of the initial diet, when the foods to be eaten on the diet are described, the above described fears, anxieties, symptoms etc are relayed earnestly by the subject.

A great improvement and advantage over any other approach in the Art is that none of the foods in the diet are familiar to the subject. Thus the subject is directed to the fact that the sincerely believed fears, associations and symptoms are not associated with the new foods, but with the old foods.

The subject is assured that the purpose of this approach is to find out how the subject's body works and to understand in such a clear, precise way that the cause and effect associations will be readily obvious to both the investigator and the subject. With the new clarity, the subject will be able to see the truth and deal with it, not simply try to ineffectively cope with misinterpretations and fears.

The first step with the anxious subject, then, is help the subject separate the anxieties and fears associated with other foods and intervention approaches with the past, and keep them there. To encourage the subject to understand that their past experiences were caused by foods that are now also in the past. That the experiences they will have in the future will be different, and the things they learned in the past do not apply to the present.

The second step is to actively involve the subject in observing and learning about the new experiences, sensations and symptoms they will be experiencing. This distracts the subject by leaving less time for irrational fears about what is coming and what will happen, since their time is occupied with observing with interest the changes in their bodies that they are experiencing, and planning and preparing for the next day's foods, which are completely different from the previous day.

The third step is to actively involve the subject in the process of observing the changes that occur once food or other problems are identified and eliminated. The subject is finally, often after years of effort, able to see sustained improvements that occur after the items causing problems are correctly identified and eliminated. As this occurs the subject is able to relax and becomes much less fearful.

The fourth step is to carefully assess and observe the symptom patterns described by the patient. Foods, for example, on the instant invention of Applicant, which includes a seven day rotation diet of the most well-tolerated foods in the world, do not cause the same symptoms day after day; there are simply too many days between the days that a food is eaten. Even delayed symptoms will generally have disappeared several days before the $8^{th}$ day when the food is eaten again. The fact that very few foods in the diet, if any, are causing symptoms, and the fact that the symptom fingerprint (array of effects on various organ systems) is unique for each food allows the investigator to distinguish between causes for foods, chemicals, pollen, molds, etc. For the instant invention of Applicant, any food problem present causes wildly fluctuating symptom patterns that recur and repeat themselves identically, in very predictable patterns, for example always on the sixth day of the rotation diet. The chemical exposures may be wildly fluctuating as well, but because of the reductions in exposure levels overall and large periods of time out of doors, will occur in a more random pattern. Pollens and molds cause symptom patterns that are consistently associated with places or certain rooms or buildings.

The pattern that points to anxiety or a fear based issue, is a symptom that is present consistently, with little variation all of the time. Much of the anxiety and fear dissipates quickly and spontaneously in the first few weeks in the instant invention program of Applicant. The cause and effects assessments coupled with simple confirming changes followed by permanent changes that provide significant, long lasting relief is a great comfort to the subject. Anxiety and fear convert to interested discovery and increasing control.

The overall patterns of the symptoms themselves become less frightening at this time. Prior to the instant invention of Applicant, heightened symptom and adverse reactions often signaled a downward spiral of illness. The subject was filled with concern and apprehension that the illness was worsening again, and would dwell with great fear and dread on the dismal future prospects. Fears of incapacitation, inability to provide an income, inability to handle medical bills, fears of loss of family support, fears of becoming totally disabled, great unhappiness and depression over prospects for solving the problems, and fears of loss of life often occupied the subjects' thoughts much of the time. The instant invention program of Applicant is an immediate and effective counter for much of this worry, hurt and fear, since these are replaced by practical, demonstrable actions the subject can take that directly helps to solve the problems and improve their lives.

During the time the subject is undergoing the instant invention program of Applicant, fluctuations in symptom levels continue initially. As the symptoms separate into distinguishable patterns they also become less frequent and the overall level of symptoms, the symptom baseline, drops. The result is that the reaction-associated symptoms the subject experiences are more obvious and more pronounced. For example, prior to the diet, an individual who rates the way he feels most of the time a 45 (0=symptom free and 100 being the worst one could possible feel) and then experiences a symptoms associated with an exposure that feel like a score of 50 on the same scale, has experienced only an increase of 5 points. After beginning the instant invention program of Applicant and responding well to the initial dietary intervention program often will experience a dramatic drop in symptoms, to a level the subject experiences as a 10 for example. When the subject now experiences symptoms associated with an exposure that feels like a score of 50, the same symptoms level is felt more strongly, now a difference of 40 points, because the overall symptom level is much lower.

This reaction, although exactly the same, now feels stronger and is scary to the anxious subject. The prior fears return, especially those of developing new sensitivities, becoming more ill, and all of the associated consequences. The subject may experience new symptoms that are anxiety related. Fortunately the reaction does not last and within a few hours or days the symptoms subside. The patient quickly realizes that the appearance of symptoms does not signal a new downturn, but merely are symptoms associated with an exposure to understand and assess with curiosity. Even the most anxious person begins to relax as the irrational fears are substituted with patterns they are helped to clearly recognize and understand. The subjects become visibly and obviously less anxious. Generally the anxiety disappears.

In those individuals in which the majority of the of the anxiety is not underlain by allergies, sensitivities and intolerances to foods, chemicals, pollens, molds and the like, but are associated to these items, the instant intervention program is also highly effective. Because the items associated with their symptoms have been eliminated, much of the anxiety is greatly relieved. In other words the instant invention program of Applicant is highly effective for anxiety and fears that are focused on foods, chemicals, pollens, molds and the like because the instant invention program of Applicant eliminates the items on which the fear and anxiety are based and eliminates much of the context and frame of reference.

In those individuals who do not spontaneously recover as a result of the highly effective and accurate program, the anxiety itself is the cause of a great majority of the symptoms experienced by the individual. These individuals generally experience significant symptom relief because of the above described elimination of familiar foods and other frames of reference. The remaining symptoms are generally easily identified as fear and anxiety based because of the patterns of symptoms described by the individuals. The generalized fears and anxieties cause symptoms that are the same day after day after day, regardless of the changes in foods, the changes in location, or the changes in air quality. Relatively constant symptoms that do not respond to the subject's highly varied and variable circumstances are not related to those now changing circumstances.

In one example, the subject, although much improved on the diet experienced symptoms every time she included oil in her diet, as she had related to us previously. For a short period of time the oils were eliminated from her diet, and the subject experienced great improvement, and was delighted. This investigator then pointed out that one of the meats in the subjects diet was very high in fat, and the subject had been eating it without any problem at all, thus fully disproving the 'all fat causes problems belief of the subject.' The subject was able to realize that this showed that her body was able to tolerate fats without difficulty. She was then gently advised that these symptoms were most likely due to her anxiety and fears. She was encouraged to talk about her feelings and began describing a desperate longing to reconcile with her divorced husband and proceeded into counseling for those and other issues. In addition, the subject was advised to re-include the oils in the diet, but to initially stir them into cereals and mashed potato-type foods so that they although present, would be less initially obvious to her. The subject did this and was able to immediately include the fats and oils in her diet without symptoms, and now uses them without concern in any manner she chooses.

It is a major advantage of the instant invention program of Applicant that it is possible to accurately distinguish between food, chemical, pollen and mold and other environmental related symptoms and anxiety related symptoms. Until now there has not been available a program that was able to accurately distinguish between real and stress-related reactions that the subject could observe and see for themselves.

In the process of the instant invention program of Applicant, because it requires that the subject take specific and purposeful action for his or her benefit, many other issues become obvious and are addressed through problem solving, counseling and support. These include but are not limited to: boundary issues, poor relationships in the family, power struggles in the family between parent and child, unassertive caregiver, overassertive, uneasy and guilt ridden about providing for her/his own needs.

The new circumstances and context of the instant invention program of Applicant are ones in which these and other problems if present cannot go unrecognized. They are also effectively addressed in the instant invention program of Applicant.

THE INSTANT METHOD FOR RECOGNISING AND ADDRESSING SOMATIC DISORDERS: rely on the simplified symptom patterns achieved as a result of the above dietary intervention strategy and the dramatic changes in frames of reference, to recognize somatic disorders.

Individuals, particularly adults beginning the instant intervention program of applicant generally have experienced myriad numbers of confusing symptoms that have responded poorly to a wide variety of treatment techniques. They have seen an average of 4 physicians of different specialties, and they have sampled a variety of alternative approaches, generally including environmental physicians, chiropractors and naturopaths. Each of these persons has prescribed a treatment approach with assurances that the approach will solve their problems. These people generally have been told they suffer from allergies, sensitivities and intolerances, multiple chemical sensitivities, Candidiasis, leaky gut, toxic effects from mercury amalgam fillings, pesticides in their tissues that need to be sweated out in daily sauna treatments, enzyme deficiencies and other nutritional deficiencies that require many supplements, all of the above, and then none of the above. Most of these persons have been advised to seek psychological help, which they have generally ignored or tried only briefly with no results.

The high accuracy of the instant invention of applicant that makes it possible to effectively identify and avoid the symptoms due to foods, chemicals, pollens, mold and the like and also make it possible to accurately identify individuals suffering from somatic disorders in a highly effective manner.

The initial diet is 1) first a method for quickly achieving a symptom-free diet for foods, the diet then becomes 2) a testing setting in which new foods can be introduced and it can be determined accurately whether the tested foods are well-tolerated, and any associated symptoms may be described, and then becomes 3) a setting in which simplified symptoms and knowledge that food as a factor is completely eliminated, makes it possible to accurately conduct cause and effect associations for chemical exposures as they are related by the subject, and then causes 4) such a dramatic, abrupt reduction in symptoms that an individuals' attempts to compensate for the abrupt drop in these exposures can be accurately observed and interpreted making it possible to rapidly and accurately identify additional allergies, sensitivities and intolerances that otherwise would be unable to discern, and in addition provide 5) .a setting in which overall symptom picture is clear enough and simple enough that accurate cause and effect associations can be made for subtle symptoms and effects that would otherwise be completely unrecognizable, and that are 6) often associated with very important major chronic diseases, these diseases themselves being not possible often to otherwise associate with their underlying causes, and in addition provides 7) a setting in which the overall symptom picture is clear enough that symptoms associated with emotions, such as fear and anxiety can be accurately identified and addressed through counseling, and provides 8) a setting in which enough of the frames of references have been removed that it is possible to clearly and unequivocally identify somatic disorders when present.

The instant invention program of Applicant has the distinct advantage of completely removing or eliminating all foods, chemicals, pollens, molds and other environmental exposures the subject is suffering symptoms from. The action-oriented effect to do whatever it takes to provide the complete symptom relief desired by the subject can be applied effectively even in extraordinary circumstances such as below.

For example, this investigator was asked to work with a very ill woman age 40 who had been bedridden for years and on total disability for over 8 years. She had reacted severely to every agent tested for in skin and scratch test generally passing out in the process. She suffered from system infections in virtually all parts of her body that were barely controlled with a long series of antibiotics, she suffered from severe asthma which required intensive intervention multiple times each day, she suffered from severe constipation, she suffered from muscle stiffness and spasms that racked her body from head to toe; she suffered from swelling and fluid retention, from sleep difficulties, and the like. She had been ineffectively treated by every conventional method available, internists, allergists, family practitioners, psychiatrists, neurologists, gastroenterologists, ear nose and throat specialists, environmental specialists, environmental allergists, chiropractors and the like. Over many years, virtually every conventional and unconventional therapy known had been thoroughly tried without improvement, and the subject's condition continued to gradually worsen.

The subject was placed on the instant dietary invention approach of Applicant and experienced immediate improvement. Because the symptoms of chemical exposures were so severe, the subject was directed to spend her waking hours and sleeping hours on her back deck where she could be free of chemical exposures. This resulted in a dramatic improvement in the subject who quickly became symptom-free most of the time. The long list of medications she had needed was gradually eliminated as was appropriate for her greatly improved medical condition.

One appointment she related a strong reaction to one of her foods, water chestnut flat bread. The reaction was swift, dramatic and severe. The subject reported chest tightness, severe wheezing, massive congestion, bloody mucous pouring from sinuses, and racking muscle spasms. The subject reported no symptoms at all from water chestnut when eaten as a creamed cereal.

Because of the highly accurate instant invention program of Applicant, and the experience gained from the instant program, this investigator knew with certainty that food allergies, sensitivities, and intolerances if present occur consistently, and not off and on like a caution light. The investigator then examined the differences between the water chestnut flat bread and the cream of water chestnut products. Having manufactured both products, the investigator also knew that the flat bread contained no added or different ingredients at all. Therefore the product type was eliminated as the cause of the observed reactions. The only difference between the two products that could be found was that one was very easy to chew and that the other was much harder to chew. This investigator then considered seriously the possibility that the strong reaction was related to muscle clenching of the subject during chewing.

Without advising the subject as to the reason so as to avoid introducing bias, the subject was advised to eliminate the water chestnut flat bread, given time to fully recover and then asked to perform a series of exercises that involved muscle clenching, such a clenching her teeth tightly, biting down on her finger, doing pull ups, doing sit ups, and so forth. With each exercise the subject became similarly ill as described above.

It became clearly obvious to the subject and to the investigator that the symptoms although real and life threatening were not associated with food, chemicals, mold, pollen, and other environmental factors. At this point the subject was encouraged to free her mind and see what thoughts and memories came when she clenched her muscles, especially her face and jaws. When she did so, the subject immediately recalled a horrific beating she received as a teenager in which she felt no pain because of intense muscle clenching. The subject was then encouraged to describe this event and recall and re-experience the physical feelings and emotional pain that she had internalized, and to appropriately direct her grief and anger to those who deserved it. She did this repeatedly until she felt no more pain and anger, and was able to eat the flat bread without effect.

This was the entée into a long series of similar experiences that led ultimately to complete relief for the subject who is now completely free of symptoms and free of all dietary or environmental restrictions, and who is now a strong, healthy, vital, vibrant woman.

The instant invention program of Applicant is powerfully effective for accurate identification of somatic disorders that have previously been the subject of contentious controversy in the field. Some physicians and other health providers have insisted that all individuals suffering from an array of food sensitivities and environmental sensitivities in fact from somatic disorders and simply need therapy. Other health providers and most patients are angered at the apparent arrogance and seek treatment to provide symptom relief and address their very real sensitivities.

Until now there has been no accurate, logical, systematic method for accurately distinguishing between the two, i.e., the real symptoms caused by exposures to foods, chemicals, pollens, molds and other environmental factors, and the real, identical symptoms triggered by associations with past abuse and other causes of somatic disorders.

The instant invention program of Applicant first begins with full acceptance of the symptoms and so forth related by the subject.

The second step involves proceeding appropriately through the instant invention program of Applicant as described above, since in the beginning the possibility of a somatic disorder is not a factor. The dietary intervention will be conducted using the instant diet of the invention.

As appropriate, exposures will be eliminated to substances for which accurate cause and effect assessments can be made. The process continues as needed until appropriate symptom relief is achieved. In the process, the use of entirely unfamiliar foods, and changing the environmental circumstances as necessary removes the frames of references for the subject. In other words, for an individual suffering from a somatic disorder, removing problem foods removes the symptoms because the frames of reference triggering the symptoms are removed.

The third step involves the recognition of reports of symptoms and reactions that do not fit the patterns for directly caused reactions and symptoms, particularly symptoms and reactions that directly conflict with each other.

The fourth step involves performing a series of simple tests that confirm the cause and effect associations.

The fifth step involves counseling to assist the individual in appropriately addressing the issues from the past.

The instant invention program of Applicant thus has the great advantage of now being able to accurately distinguish between allergies and sensitivities and somatic disorders. This has previously been an area of great contention and controversy, in the prior art. Health providers previously claimed all sensitivities were somatic disorders, particularly reports of chemical sensitivities, and other health providers claimed that no sensitivities were the result of somatic disorders. The instant invention of Applicant provides an approach and structure that allows the health provider for the first time to be able to accurate distinguish between those suffering from somatic disorders, those suffering from allergies, sensitivities and intolerances, and those suffering from both, and finally to provide appropriate and productive assistance to both.

THE INSTANT METHOD FOR RECOVERING FROM CHRONIC DISORDERS: focus on the underlying causes, rely on the simplified symptom patterns achieved as a result of the above dietary intervention strategy and the subsequent identification and elimination of all other exposures, to completely relieve the underlying causes for a large number of chronic diseases.

There has been a steady increase in the incidence of chronic diseases in the past several decades. This investigator notes that the incidence of chronic diseases also parallels the rise in allergies and sensitivities and intolerances.

This investigator has found that through the instant invention program of Applicant individuals can recover completely from early to moderate stages of chronic diseases unless the damage caused by the disease has caused permanent tissue damage from which tissue regeneration is not possible, which is generally characteristic of later stages.

This investigator has found that years of continual exposures to substances that cause the continuous symptom levels and patterns described earlier, generally precede the emergence of recognizable chronic disorders.

Thus this investigator has further found that the above described approach for foods, chemicals, pollens, molds and other environmental factors, emotional issues and somatic disorders, is highly effective in providing complete relief from chronic disorders that have not proceeded to the final stages.

The investigator has found that using the instant dietary intervention approach of applicant as the first step, and following the approach as outlined above, causes complete relief from the chronic disorder itself. The approach is identical, regardless of whether the individual suffers from allergies and sensitivities in general or has proceeded to the point that the individual is now suffering from a recognized chronic disease.

Examples include but are not limited to: multiple sclerosis, autism, PDD, hyperactivity, Crohn's disease, irritable bowel syndrome, arthritis, migraine headaches, Alzheimer's disease, diabetes.

Unique to the instant invention program of Applicant is the emphasis on complete elimination of symptoms, including symptoms that are mild and subtle, although chronic. This investigator has found that chronic symptoms, and the prolonged expression of chronic symptoms are the early signs of serious chronic disorders. For example a large percentage of early onset autistic children begin with an early diagnosis of colic. Similarly adults suffering from a variety of digestive disorders experienced colic as an infant. Conversely, this investigator has found that focusing on complete elimination of all symptoms, even minor ones, and completely eliminating their cause, consistently leads to the reversal of even serious chronic diseases.

This investigator recognizes that the current intent of the Art is to alleviate acute symptoms, and serious health problems, while mild and subtle complaints are left essentially unaddressed. Examples of these are post nasal drip, fatigue, mild congestion, mild to moderate constipation, mild to moderate diarrhea, lethargy, itching, headaches, muscle aches, muscle stiffness. For these an individual is generally left to treat on his or her own.

This investigator has discovered that the identification and complete elimination of agents that cause these symptoms is the vital and essential link that prevents or eliminates serious chronic diseases in these subjects. Further this investigator has found that left unaddressed, years of experiencing such relatively minor symptoms as these, and their chronic effects on overall body function, most certainly leads to a variety of serious chronic diseases.

The instant invention program of Applicant is one that allows an investigator to, through careful application of the above described intervention program and the cause and effect process that this involves, identify specific causative agents underlying symptoms an individual is experiencing, and to continue that process until no symptoms remain. This investigator has further found that in this process, symptoms perceived as subtle and minor are equally important to those that are more serious.

The instant invention program of Applicant achieves relief from symptoms through intervention and avoidance, as opposed to providing a treatment that prevents the symptom from being expressed. For example, if a person is found to be suffering headaches from exposure to perfume, the exposure is removed in preference to treating the headache with an analgesic and continuing the exposure. The Applicant has found that the effects of the exposure, in this example the exposure is to perfume, in terms of the effect on and alteration of body function, is greater than solely causing a headache, but much of the remaining effect is not possible to discern. Applicant further has found that elimination of this exposure, not only eliminates the effects on and alterations in body function that can be observed, but also all other effects, including those that are important but are not observable, many of these involve biochemical processes.

By eliminating what can be observed, thus simplifying the symptoms and making it possible to observe other symptoms and their causes, by again eliminating what can be observed, and continuing this process until no further symptoms remain, the improvement experienced by the subject is greater than the symptoms that were recognized and for which exposures were eliminated.

The instant invention program of Applicant is a method for eliminating all symptoms, certainly the most obvious and serious of the symptoms, but most importantly, also eliminating the subtle, moderate and minor symptoms, thus effectively treating a wide variety of chronic diseases.

Further Applicant has found that when mild, subtle, moderate symptoms are considered, and the agents responsible for symptoms are identified and eliminated, that each individual is unique in terms of his or her symptom patterns. In other words, the particular way in which substance 'A' affects person 'A' is found to be unique. The particular set of symptoms and the 'fingerprint' of symptoms is as unique as a fingerprint. Using headaches as a example, the substance or substances causing person 'A' to experience a headache, may be virtually anything: any food, and chemical exposure, any pollen, any mold, any other environmental exposure. Further when the headaches of the next 100 persons are carefully studied, each of these individuals may also experience a headache from virtually anything: any food, and chemical exposure, any pollen, any mold, any other environmental exposure. When the exposures causing the headache effects for each individual are fully known, the causes will be uniquely different for each individual.

Similarly when a particular item is considered, such as a food, chemical, mold, pollen, or other environmental exposure, for example a perfume, for any given 100 persons sensitive to that perfume, when the symptoms are clearly described, each person will experience a uniquely different array of symptoms, which could be any symptom at all—digestive, emotional, loss of vision, headaches, effects on skin, congestion, infection, fatigue, asthma, seizures and on and on.

This investigator finds that mild, moderate, subtle symptoms are unique expressions of the body's functioning processes of each individual, and therefore, the instant invention program of Applicant is a process and a methodology for understanding and identifying, through simplified symptom patterns, cause and effect associations, the unique exposure-response patterns for each individual and their effects expressed in terms of specific, uniquely expressed symptoms, and further for using this information to develop effective avoidance strategies that result in alleviation of the associated symptoms and associated chronic diseases.

This instant invention program of Applicant is a method for treating chronic diseases that identifies and eliminates the unique, underlying, individual causative agents due to allergies, sensitivities, intolerances, emotional factors, and somatic disorders.

The instant invention program of Applicant is a method for developing an individually tailored assessment and treatment plan that is uniquely appropriate for each individual.

The instant invention program of Applicant is a method for effective treatment of chronic disorders and diseases that simplifies the extraordinary complexities and challenges presented by individually unique arrays of symptoms and exposures in which no two patterns are alike.

The instant invention program of Applicant is an approach for evaluation and assessment of individually unique arrays of symptoms and exposures in which no two patterns are alike.

The instant invention program of Applicant is an approach for cause and effect assessment of individually unique arrays of symptoms in which no two patterns are alike.

The Instant Method for Conducting Effective Research:

The final advantage of the instant invention program of applicant is that for each type of symptom and chronic disorder, it is now possible to conduct accurate, and effective research programs that can investigate chronic disorders and more fully describe the mechanisms involved. Can more clearly describe and biochemically characterize the mechanisms of chemical allergies, sensitivities and intolerances, and can finally begin a productive investigation between the chronic disorders and psychological and emotional issues and chronic diseases.

EXAMPLE 1

Recovery Patterns in Autistic Individuals Who have Achieved Complete Symptom Relief from Food Allergies and Sensitivities with the Special Foods Diet Children and young adults following the instant invention program of Applicant show the following patterns. In virtually all cases there is a sudden, abrupt disappearance of a number of symptoms, and this disappearance coincides with the elimination of the last problem food. The types of symptoms that suddenly disappear are not generally related to learned behaviors. The abruptly disappearing symptoms are generally related to the disappearance of pain, disappearance of hypersensitivity to external stimuli, disappearance of agitation and the like such as screaming, head banging, rages, and obsessive compulsive behaviors. In place of these symptoms is an apparent new state of peacefulness and calm, both day and night, and frequently includes the child being able to consistently sleep through the night for the first time. There follows a quiet period in which the child appears to simply savor the new state of being. After adjusting to the change, there is then a rapidly increased awareness of and interaction with the environment, and a rapid learning period.

This is the pattern observed in individuals whose symptoms are primarily caused by food allergies, sensitivities and intolerances. Individuals also experiencing symptoms from chemicals, pollens, molds, and other environmental factors, experience a similar pattern, but do not reach the zero symptom level until exposures to the other factor has been eliminated.

FIG. 1 traces the changes in symptoms exhibited by autistic children and young adults beginning with the time the diet is begun.

(1) Symptom level prior to intervention with the Special Foods Diet: The prior symptom level represents the starting point for each person.

(*) The starting point for the Special Foods Diet is represented with the asterisk. Generally the symptom level was found to remain relatively unchanged for the first one to two days.

(2) Withdrawal and resistance to the diet: The withdrawal period for the Special Foods Diet is very similar to that described for other kinds of dietary intervention strategies; although because the method more completely eliminates problem foods, the withdrawal intensity may be slightly stronger. In general, it was found that the symptoms most enhanced during a withdrawal period were those most likely to be abruptly eliminated when a problem-free diet was achieved.

Withdrawal and resistance to the diet was found to be the least among the most severely autistic children, who were the least aware of their surroundings. They have occasionally progressed through the withdrawal period and toward a symptom-free state before they were aware of a change. Greatest resistance was found in high functioning individuals.

The duration of withdrawal and dietary resistance was found to be highly variable. This was not unexpected. In general this occurred during days 3-7 of the diet, but could be as few as 0 days and as many as 14 days.

(3) Weeks 3-5, times of healing and observing: Even before achieving a symptom-free diet, significant improvements were generally observed during this period. This is represented by the slope of line three (3). The observed improvement is probably due to the fact that for most persons, there are generally only a very few (1-2) problem foods remaining in the Special Foods Diet, even from the outset. Thus over 90% of the food-related stress has been eliminated on the first day of the Special Foods Diet. A significant amount of healing occurs simultaneously with symptom observations and with limited food challenges and reaction observations (if any); this is because there are in fact so few problem food exposures in comparison to the person's recent past. Wounds and irritated mucous membranes begin healing during this time, with very positive concomitant changes in gut absorption; this also contributes to the observed improvements. By 3-5 weeks, stool consistency and evacuation should be completely within normal limits.

(**) Achieving a problem food-free diet: The full extent of a food-related symptom pattern can only be fully appreciated when the final food is eliminated from a child's diet. This point is achieved at week five (5) of the Special Foods Diet. It is so important and essential, that when necessary weeks 4 and 5 should be repeated in several cycles until this point is achieved. There does not appear to be a symptom so subtle that it can be ignored. Because autistic children are frequently unable to assist verbally in determining when a food is a problem food, and reactions can be subtle or delayed, it may often take several cycles of food challenges, food elimination, and repeated observations. In the most difficult cases, this required 2-3 months. A problem-free diet is achieved when there is no change in behavior, no 'good' days and 'bad' days, over a full rotation.

(4) Precipitous drop in symptoms: There is a sudden, abrupt disappearance of food-related symptoms that coincides with the elimination of the last problem food. The types of symptoms that suddenly disappear are not generally related to learned behaviors. The abruptly disappearing symptoms are generally those that have been associated with intense pain, intense irritation and inflammation of mucosal linings, hypersensitivity to external stimuli, emotional distress such as intense agitation and the like. Examples include screaming, head banging, rages, obsessive compulsive behaviors, migraine headaches, and severe stomach aches, agitation, and insomnia.

Such symptoms are similar to those experienced by individuals with moderate food allergies and sensitivities, but tend to be far more intense in the autistic child with food sensitivities. This accounts for the more intense behaviors that can include self abuse or abuse of others. Thus the mechanisms, on a biochemical basis are similar, the effects are more severely experienced by the autistic child.

The importance here is to note that a definite type of initial response has been observed when a diet completely free of all problem foods is finally achieved. The response tends to be immediately and directly physical, although the physical relief may be expressed indirectly, such as by no longer pounding on one's head since the migraine headache is gone.

(*) THE ZERO POINT: A primary goal of the Special Foods Diet is to achieve this point. The release of the last food related stressor, and therefore a full body relief from the effects of reactions and associated biochemical alterations is a very noticeable physical shift.

Food-related reactions have long been known to cause a multitude of alterations of biochemical mechanisms in the body. Repeated reactions cause the immune system to become hypersensitive. This very tangible, discernable shift in body function and state of well being experienced by every person who has achieved 'the zero point' with the Special Foods Diet, may be related to biochemical shifts away from abnormal response patterns associated with food reactions to normal biochemical food response patterns. This noticeable shift in body function has been observed only when complete elimination of every food-related stressor is achieved.

(5) Quiescent period: This period is the point at which the response of autistic children to the Special Foods Diet, has been found to differ significantly from that of individuals with food allergies and sensitivities who are not autistic. The quiescent period is not observed for the other groups of individuals. They simply maintain the 'zero point', heal, and go on with their lives. When 'the zero point' is achieved and maintained in an autistic child there is a quiescent period that can be either very short or can last for months. In young children, age three (3) and below this period can be short, lasting only days or weeks. In the oldest individual studied (21 years of age), this period lasted about ten (10) months.

The quiescent period is a time of peace, rest, and adjustment. In place of the old all-consuming horrific symptoms is a very apparent new state of peacefulness and calm, both day and night, and frequently includes the child being able to consistently sleep through the night for the first time. During this time the child appears to simply savor and become accustomed to a new state of being. Because this response is so consistently observed, it is an apparent important part of the recovery process. After what for some has been years of horrific, unexpressed pain, the mere absence of the pain must be quite a shock to adjust to. Dramatic personality improvements generally are associated with the beginning of the quiescent period; these changes are sustained as long as the 'zero point' is maintained. Rages, flailing, self-abuse, abuse of others and the like, are replaced by peacefulness, quiet, calm, and often accompanied by smiles from within.

(6) Learning period: The end of the quiescent period is marked noticeably by a sudden, pronounced increased awareness of and interest in people, things, and all aspects of the surrounding environment. The non-verbal child may suddenly start to babble. The non-interactive child may look a parent in the eyes and smile. Interactive play and responsiveness to commands suddenly become more appropriate. The best description is that after becoming used to the absence of horrific pain and the like, and finally deciding that it is not coming back, they are suddenly ready to see what the world beyond their inner place is all about!

However, change from the quiescent period to the learning period has tended to be sudden and obvious. Because it is so easily recognized, it is not difficult to tell when to introduce approaches to enhance and accelerate the learning process. Implemented at this time and in this way, learning strategies tend to be associated with rapid progress.

EXAMPLE II

An Example of a Dietary Intervention and Guidance to Study Participants Undergoing the Instant Invention Program of Applicant This instant invention of Applicant was called the Special Foods Diet, in reference to the concentrated forms of tropical root crops and the other unusual food on the diet.

The purpose of this booklet is to suggest to you what we believe is the best method for fast, total relief of symptoms due to food allergies, sensitivities and intolerances. In spite of the complexities associated with determining specific food allergies, sensitivities and intolerances, the diet represents a fast, accurate way to find a set of foods that are the best, most well tolerated foods that exist anywhere. It is based on the philosophy that in the same way there a foods that cause people problems, there is a set of foods that are the best in the world for a person, so right that the body seems to say . . . Ahhh! a sigh of relief. These foods are most likely unusual foods that have never been eaten before, that are specially prepared to avoid molds and chemical contamination eaten in a 7-day rotation plan with optimum balance and quantities of calories, carbohydrates, fats and proteins. So this diet becomes a wonderful experience in which your body receives the most nourishing well-tolerated food you have ever had in your life. The results are fast, frequently occurring within four to seven days, and by staying on this diet long enough, complete recovery from food allergies, sensitivities and intolerances is possible for many. We will tell you how to determine the best foods in the world for you, how to develop a diet based on these foods that is the most nourishing you have ever experienced, how to achieve all the variety in serving choices you desire, and we will tell you how to give your self the best chance of recovery possible.

I—Background

The symptoms and problems that have been associated with food allergies, sensitivities and intolerances are many and varied. The symptoms and problems can involve virtually any system of the body, often in combinations involving multiple systems simultaneously, and can express themselves in symptoms of varying intensity, ranging from barely noticeable to life threatening. Often the simultaneous expression of symptoms in multiple systems occurs together with this widely ranging array of intensity of symptoms, with some symptoms being obvious and others being barely discernable. Of the rare times when it has been possible to fully identify and describe the complete symptom expression pattern for food reactions, the results show that each food tends to cause a unique pattern of expression and that this pattern is different for each person.

For this reason food allergies, sensitivities and intolerances have been called the great mimicker, because the array of symptoms can appear to be like any number of chronic disorders, and can even mimic several at once. Of course it is also possible for there to be both chronic disorders and food allergies, sensitivities and intolerances occurring simultaneously, making diagnosis even more complicated and difficult.

If this isn't bad enough, there seems to be a feed back loop that causes an over reactive (thus hyper strong) immune system to behave as if it were very weak! When the immune system over reacts, for example to a food, there appears to be a feed back loop that tries to compensate for this over reacting. It is an attempt on the part of the body to reduce the tendency to over reaction. Unfortunately, it appears that the immune system, instead of dampening responses to food reactions, actually dampens ability to resist infections. Thus persons suffering from prolonged problems related to food allergies, sensitivities and intolerances frequently suffer from repeated infections of various kinds, and appear to have difficulty overcoming infections. It can be a vicious cycle: food and other reactions causing various mucous membranes to become swollen and irritated, providing an improved site for invading bacteria and other organisms, while at the same time providing reduced ability of the body to fend off these organisms. This may be the reason that many persons report a history of frequent, repeated treatment with antibiotics.

Consider also the recently published studies indicating that many chronic disease processes have systemic infections as underlying causes. Ulcers are now known to be commonly caused by *Helicobacter pylori*, and more recently infectious organisms have been linked to ulcerative colitis, Crohn's disease, arthritis, and diabetes. This means that the person suffering from food allergies, sensitivities and intolerances may be at greatly increased risk of such disorders, and of experiencing great difficulty responding successfully to antibiotic treatment for these disorders.

In addition food allergies, sensitivities and intolerances can express their effects in a myriad of ways that result in substantial alterations of biochemical processes and substantial interference with the body's ability to absorb and assimilate nutrients from food. This causes a 'chicken or the egg' type of dilemma, ie, which comes first, the malabsorption and/or biochemical imbalance or the food sensitivity? When dietary intervention is accomplished first, all food-related causes of altered biochemical functioning can be eliminated and the body will finally have a chance to function in its own normal way. Only then is it appropriate to consider whether biochemical imbalances remain. Generally the problems that remain are small, if any. And again when dietary intervention is accomplished first, other contributing factors, if present, will be much more easily discerned and addressed.

It would be nice if there were a 100 percent accurate test available for food allergies, sensitivities and intolerances, but alas, there probably never will be. Foods contain literally hundreds of thousands of substances. Some food intolerances are simply the lack of a particular enzyme; some allergies are clearly immunological in nature; the underlying biochemical mechanisms of many sensitivities have yet to be adequately described or understood. In any person food allergies, sensitivities and intolerances can occur at any step in the cooking process and in the metabolic processes of breakdown, assimilation and elimination. It is hard to imagine that there will ever be a test that measures every metabolic step of digestion for all of the substances in a food in the cooked and uncooked form, and peeled and unpeeled form, accounting for immunological responses and enzymatic and other insufficiencies possible in skin, in mucous membranes in the mouth, stomach, intestines, and those possible intracellularly. Fortunately, to search for the foods that are best for you, tests are not very helpful, since you are not likely to have eaten these foods yet and they are not likely to have been included in the testing protocol. Testing may be more helpful after you have a good diet and are symptom free, to help guide your choices of what foods to add back into your diet first.

The only universally accepted approach is to believe what your body actually tells you. It is true if you eat a food and it causes problems, and you can reasonably correlate the cause and the effect, you can believe the results. It is also true that, if a food causes problems of some type and you do not eat that food, it can not cause those problems. Because most people eat so many different foods, because of the times period involved for digestion, assimilation and elimination, because reactions many be immediate or delayed, and because reactions may be short or long in duration, accurate dose-response assessments can be very difficult. In individuals who have been carefully tested, food allergies, sensitivities and intolerances are almost always accompanied by chemical sensitivities. Because of this eating a diet of only well-tolerated foods is important because it eliminates the symptoms caused by foods and thus makes it easier to correctly interpret symptoms caused by all other remaining factors. Food allergies and sensitivities can be completely avoided by changing the foods one eats, and thus it is relatively easy to eliminate food-related problems. When this is accomplished first, other contributing factors, if present, will be much more easily discerned and addressed.

Considering the above, a Dietary Intervention Approach that can quickly and effectively eliminate symptoms due to food allergies, sensitivities and intolerances is important to a great many people:

II—The Diet

The instant invention program of Applicant is a simple, fast way to determine the maximum benefit in terms of symptom relief that is possible to achieve from an elimination diet, while at the same time optimizing nutritional content and minimizing the chances of developing new food sensitivities. The Special Foods! Diet began as a set of instructions describing a way in which each person could develop an individually tailored diet. Although we still wholeheartedly endorse this approach and the instructions are included in this booklet (see Appendix B), the response from many was essentially—just do it! When food allergies are unclear as they are for virtually everyone, and the foods are unfamiliar, how is anyone going to be able to know enough to set up a diet? Believing that our guess would be as good as theirs would be, we have repeatedly been asked to recommend a specific diet. And that is just what we have done. The diet below is the Special Foods Diet. It is a gluten-free diet, and contains the complex carbohydrates, that in our experience are the most well-tolerated. These complex carbohydrates are also very high in soluble and insoluble fiber, and contain very high levels of many vitamins and minerals.

The diet shown in Table 1 is for person wishing to emphasize food allergies, sensitivities and intolerances. The diet shown in Table 3 is for persons who know they are very severely mold sensitive. In this version the nuts and fruits have been removed.

TABLE 1

The Special Foods! Diet

| Type of Food & Recommended Quantity for Adults | Day 1 | Day 2 | Day 3 | Day 4 | Day 5 | Day 6 | Day 7 |
|---|---|---|---|---|---|---|---|
| Complex Carbohydrates As fresh vegetable, about 5 lbs per day As dry flour or seed, at least ▢pound (women), at least 1▢ pound (men) | White sweet potato | Water chestnut | Malanga | Arrowroot | True yam | Lotus | Cassava |

TABLE 1-continued

The Special Foods! Diet

| Type of Food & Recommended Quantity for Adults | Day 1 | Day 2 | Day 3 | Day 4 | Day 5 | Day 6 | Day 7 |
|---|---|---|---|---|---|---|---|
| Green Leafy and Other Vegetables Eat as much as desired, generally 1–2 pounds per day, but do not count as a calorie source. Be sure to leave room for the complex carbohydrates. | Chinese cabbage, kohlrabi, turnips | fresh water chestnuts, acron squash, spaghetti squash chayote | celery root, parsnip, fennel | beet greens, chard | alfalfa sprouts, jicama | endive, burdock root, dandelion greens | asparagus okra |
| Meats approx 5 oz per day total | turkey | swordfish | Duck | clams | crab | venison | rabbit |
| Nuts and Oils Oil: use approximately 4 Tablespoons per day. Nuts: Use in moderation, reduce amount of oil slightly if you use nuts | canola oil; pinyon nuts | pumpkin seed oil, pumpkin seeds | macadamia oil, macadamia nuts | hazelnut oil, hazelnuts | Brazil nuts avocado oil, avocados | coconut oil, fresh coconut meat | apricot oil |
| Fruits Eat as desired, but do not use in place of foods and quantities listed above. | kiwi fruit | mango | persimmon | Fresh figs | papaya | starfruit | fresh persimmon pomegranate, lychee, custard apple |

Nutrition is extremely important in any diet, and particularly important in this diet. Therefore we have translated the Recommended Dietary Allowances (RDA) of the National Research Council into quantities a person needs to consume throughout the course of a day in order to meet the requirements of the RDA. Although these numbers seem high, they accurately reflect the RDA values, and illustrate very vividly why so many people get into trouble when they try to make dietary changes. When one type of food (carbohydrate source), i.e., mashed potatoes has to stand in for several forms of carbohydrates, i.e., bread, milk, dessert etc, then multiple servings of the one food must be eaten. This is where most people make their mistake and end up eating only 20-25 percent of what their body needs.

The recommended quantities included in the right hand column of the table above, are quantities recommended for adults. The table below presents the recommended daily quantities for children. Select the column in Table 2 that corresponds to your child's age. During the time on the diet, after the first 1-2 rotations, you should make sure that you or your child eats, as a minimum, the recommended quantities listed in the appropriate column of Table 2.

TABLE 2

Daily Quantities for Children on the Special Foods! Diet

| Type of Food | Children 1–3 years | Children 4–6 years | Children 7–10 years | Girls 11–18 years | Boys 11–22 years |
|---|---|---|---|---|---|
| Complex Carbohydrates | As fresh vegetable, eat about 2½ pounds per day. As dry flour or seed, at least ½ pound per day. | As fresh vegetable, eat about 3¾ pounds per day. As dry flour or seed, at least☐ pound per day. | As fresh vegetable, eat about 5½ pounds per day. As dry flour or seed, at least 1 pound per day. | As fresh vegetable, eat about 5½ pounds per day. As dry flour or seed, at least 1 pound per day. | As fresh vegetable, eat about 5½ pounds per day. As dry flour or seed, at least 1½ pound per day. |
| Green Leafy and Other Vegetables | Eat as much as desired, generally ½–1 pound per day, but do not count as a calorie source. Be sure to leave room for the complex carbohydrates. | Eat as much as desired, generally 1–1½ pounds per day, but do not count as a calorie source. Be sure to leave room for the complex carbohydrates. | Eat as much as desired, generally 1–2 pounds per day, but do not count as a calorie source. Be sure to leave room for the complex carbohydrates. | Eat as much as desired, generally 1–2 pounds per day, but do not count as a calorie source. Be sure to leave room for the complex carbohydrates. | Eat as much as desired, generally 1–2 pounds per day, but do not count as a calorie source. Be sure to leave room for the complex carbohydrates. |

TABLE 2-continued

Daily Quantities for Children on the Special Foods! Diet

| Type of Food | Children 1–3 years | Children 4–6 years | Children 7–10 years | Girls 11–18 years | Boys 11–22 years |
|---|---|---|---|---|---|
| Meats | Eat approximately 2½ ounces per day total. | Eat approximately 3½ ounces per day total. | Eat approximately 4 ounces per day total. | Eat approximately 5 ounces per day total. | Eat approximately 5 ounces per day total. |
| Nuts and oils | Oil: use approximately 2☐ Tablespoons/day Nuts: Use in moderation, reduce amount of oil slightly if you use nuts. | Oil: use approximately 3½ Tablespoons/day Nuts: Use in moderation, reduce amount of oil slightly if you use nuts. | Oil: use approximately 5 Tablespoons/day Nuts: Use in moderation, reduce amount of oil slightly if you use nuts. | Oil: use approximately 5 Tablespoons/day Nuts: Use in moderation, reduce amount of oil slightly if you use nuts. | Oil: use approximately 6 Tablespoons/day Nuts: Use in moderation, reduce amount of oil slightly if you use nuts. |
| Fruits | Eat as desired, but do not use in place of foods and quantities listed above. | Eat as desired, but do not use in place of foods and quantities listed above. | Eat as desired, but do not use in place of foods and quantities listed above. | Eat as desired, but do not use in place of foods and quantities listed above. | Eat as desired, but do not use in place of foods and quantities listed above. |

TABLE 3

The Special Foods! Diet for Severely Mold Sensitive Persons

| Type of Food & Recommended Quantity for Adults | Day 1 | Day 2 | Day 3 | Day 4 | Day 5 | Day 6 | Day 7 |
|---|---|---|---|---|---|---|---|
| Complex Carbohydrates As fresh vegetable, about 5 pounds per day As dry flour or seed, at least ☐pound (women), at least 1☐ pound (men) | White sweet potato | Water chestnut | Malanga | Arrowroot | True yam | Lotus | Cassava |
| Green Leafy and Other Vegetables Eat as much as desired, generally 1–2 pounds per day, but do not count as a calorie source. Be sure to leave room for the complex carbohydrates. | Chinease cabbage, kohlrabi, turnips | fresh water chestnuts, acron squash, spaghetti squash chayote | celery root, parsnip, fennel | beet greens, chard | alfalfa sprouts, jicama | endive, burdock root, dandelion greens | asparagus okra |
| Meats approx 5 oz per day total | turkey | swordfish | duck | clams | crab | venison | rabbit |
| Oils Oil: use approximately 4 Tablespoons per day | canola oil | pumpkin seed oil | macadamia oil, | hazelnut oil | avocado oil, avocados | coconut oil, | apricot oil |

III—Recommendations that Help Make the Diet Easier to Follow and More Successful 1) Regarding foods:
   a) Resist the temptation to try a 'partial' diet—There is a much greater chance of developing sensitivities to the new foods when you do this. Do not consume any food that is not listed on the diet.
   b) The quantities of the various types of food which have been recommended in the preceding tables for children and adults are particularly important. Other than during the first week or two on the diet, these quantities should be carefully followed. The recommended quantities are based on Recommended Dietary Allowances (RDA) published by the National Research Council, National Academy of Sciences.

Do not restrict the total amount a child wants to eat; if he or she wants to eat even 50% more, let them, but do insist that they eat all foods in the general proportions given. If the child consumes 50% more, it should be 50% more of everything.

c) Once you start on your diet, try to follow it carefully. You can occasionally switch foods around, but then continue to follow the changed diet. One important feature of your diet is that foods are not eaten more frequently than once every seven days. When food switches are made frequently this important time period begins to be lost.
d) Cook fresh, frozen or dried foods; do not use canned foods. Do not use any food that has any other than approved ingredients on the package.
e) As much as possible select only organically grown foods for this diet.
f) Include non-iodized sea salt as desired in the diet; iodized forms contain corn or substances derived from corn. Although you should not use excessively large quantities of salt, you should definitely use salt, so for most people it is appropriate to use salt as desired.
g) This diet is well balanced, and you will need no vitamins other than calcium. Use a pure mineral form of calcium such as dolomite or calcium carbonate; follow instructions on the label.

2) Regarding water: For drinking and cooking use spring water or distilled water only. Use water only (as spring water or distilled water) for drinking on this diet.

3) Regarding chemicals: Persons with food sensitivities are invariably also sensitive to many chemicals. You are very likely to begin observing this as food-related symptoms begin to subside. The more you can avoid chemical exposures, the better. Use only unscented soaps, detergents, shampoos, and personal care products. Do not use perfumes or other scented products during the five-week period. You or your child should spend as much time outside in fresh air and sunshine as possible; the best would be to be outside during waking hours (easiest for a child)—work toward this goal. Stay indoors in air conditioning with windows and doors closed when pollen or mold counts are high outdoors.

IV—What to Expect on Your Diet

1) For the first rotation and possibly two rotations, do not expect too much. Whatever you observe, do your best to ignore it, unless, of course, something is happening that is unrelated to the diet. Remember that appendicitis or ear infections can occur at any time. Other than this, the first week or two is a time when withdrawal may occur, so you may notice temporarily heightened symptoms. You may also notice frustration since a person may really be missing foods and other items that had been relied on. Also, there may be delayed food reactions during this time. Try to remember that whatever occurred on one day due to a food cannot be repeated the second day because the foods are completely different.

2) Know before you begin your diet the amount of each type of food to eat each day; see Table 1 and 2, above, for general guidelines on appropriate quantities. Especially during the first week of the diet, do not insist that a child eat the quantities listed if he or she does not want to. Many times children just do not feel like eating much while their bodies adjust. Begin to be more insistent during the second week, and by the third week you should insist that the appropriate quantities are consumed every day. If a person gets full quickly, the solution is to eat more frequently.

3) Beginning with the third week, you should begin to look for very real signs of change/improvement. Any symptoms which appear consistently on the same rotation day regardless of changes in environmental settings, would more likely be food related, and you should adjust the diet by eliminating the problem food or foods, if you can tell which is the problem. If you cannot tell what food is causing the problems, try single food meals on the next rotation day. For example, meat in the morning, carbohydrate for lunch, etc. This will make it easier to determine what food is causing the problem and therefore needs to be eliminated. Symptoms that seem to occur at random or symptoms that sometimes occur but then do not always occur are generally not indicators that point to a food problem. The occurrence of random symptoms is generally the first indication of chemical sensitivities.

4) When you begin to see significant signs of improvement, continue carefully on the diet, and be particularly aware of environmental influences; it will be particularly important to avoid as many chemical exposures as possible during this time.

Detailed Dectription of the Diet Selection Embodiments Selection of Carbohydrates for the Instant Invention of Applicant In one embodiment of the instant invention of Applicant, any of the carbohydrates below that have been eaten more than twice per year previously, are eliminated from the diet. In a more preferred embodiment the carbohydrates are selected from sources that are not the most frequently eaten and most common problem carbohydrates, such as common cereal grains from the grass family; and are selected from sources that have not been eaten more than twice per year previously. In a more preferred embodiment, carbohydrates are selected from sources that are not the most frequently eaten and most common problem carbohydrates, such as common cereal grains from the grass family, and are selected from sources that have not been eaten more than twice per year previously, and are selected from carbohydrates not known to cause reactions for the subject. In another preferred embodiment, the carbohydrates are selected from sources native to tropical Africa and Asia. In a more preferred embodiment, the carbohydrates are selected from sources that are not the most frequently eaten and most common problem carbohydrates, such as common cereal grains from the grass family, are selected from sources that have not been eaten more than twice per year previously, are selected from carbohydrates not known to cause reactions for the subject, and are selected from sources native to tropical Africa and Asia.

In one embodiment of the instant invention of Applicant, each carbohydrate is selected from a different food family. In a more preferred embodiment, the carbohydrates are selected from sources that are not the most frequently eaten and most common problem carbohydrates, such as common cereal grains from the grass family, are selected from sources that have not been eaten more than twice per year previously by the subject, are selected from foods not known to cause reactions for the subject, are selected from sources native to tropical Africa and Asia, and each carbohydrate is selected from a different food family.

EXAMPLE III

Examples of Carbohydrates for the Instant Invention of Applicant

These carbohydrates have been shown to work well in the instant invention of Applicant.

| | | |
|---|---|---|
| Sweet potato family (Convolvulaceae): white sweet potato | Aroid family (Araceae): malanga | Spurge family (Euphorbiaceae): cassava |
| Water lily family (Nymphaceae): lotus | Water chestnut family (Cyperaceae): water chestnut | Dioscorea family (Dioscoreaceae): yam (true yam) |
| Arrowroot family (Marantaceae): arrowroot | | |

EXAMPLE IV

Examples of Other Carbohydrates for Instant Invention of Applicant

The above examples have been shown to work well in the instant invention of Applicant, and are listed above for purposes of illustration and example. The edible roots of each of the families listed below are tropical root crops that are also included in the instant invention of Applicant. They represent the primary carbohydrate sources of man as the human race emerged.

The term root or tuber is used below and throughout this application to refer broadly to the edible underground storage structures of each taxonomic family. The term is intended to be applied broadly to all members, regardless of whether the actual structure is a root, rootlet, corm, tuber, tuberous root, rhizome, bulb or the like.

EXAMPLE V

Examples of Carbohydrates Available to Add to the Diet on a Trial Basis After Achieving the Zero-symptom Baseline During initial diet expansion usual items that are not tropical root crops are introduced first, prior to the common members of the legume, grass, and nightshade families. No food is introduced, even on a trial basis for which the subject previously experienced reactions.

At this time carbohydrates from the above list may also be included, including the non-tropical roots, rhizomes, bulbs, corms, tubers, tuberous roots, and the like of each of the families listed above. The non-tropical roots, rhizomes, bulbs, corms, tubers, tuberous roots, and the like of each of the families listed above are hereby included in the embodiments.

| | | |
|---|---|---|
| Mallow family: cotton seed flour | Palm family: sago palm starch | Sorrel family buckwheat |
| Goosefoot family: sugar beet, amaranth quinoa | Legume family: mung beans | Bromeliaceae, v high Calcium content bulb, Bromelia laciniosa |
| Gentianaceae family: buckbean | Campanulaceae Chinese bell flower root | |

| | | |
|---|---|---|
| Sweet potato family (Convolvulaceae): other tropical roots | Aroid family (Araceae): taro, tannia, dasheen, eddo, amorphophallus, malanga lila, cocoyam, cocoeddo, Portland arrowroot, and many others | Spurge family (Euphorbiaceae): cassava (many tropical roots), Brazilian arrowroot |
| Water lily family (Nymphaceae): Chinese arrowroot, blue water lily, many tropical roots | Water chestnut family (Cyperaceae): tiger nut, *Cyperus* sp., *Scirpus* sp., and other edible tropical roots | Dioscoreaceae family: yam, guinea yam, (many tropical yams), Figi arrowroot, tacca, Tahiti arrowroot, including edible roots of Taccaceae |
| Arrowroot family (Marantaceae): other tropical roots | Alismataceae family: arrowhead, ci gu, Chinese potato, swamp potato | Cannaceae family: Queensland arrowroot, canna |
| Cycadaceae family: Florida arrowroot, Mexican arrowroot, cycas arrowroot, Dioon edule, and other edible tropical roots | Milkweed family Asclepiadaceae edible tropical roots | Zingiberaceae family: east Indian arrowroot, curcuma, and other edible tropical roots |
| Iris family (Iridaceae) edible tropical roots Liliaceae edible tropical roots | Leguminosae tuber of African yam bean, wing bean root, vigna roots (*Vigna* sp.), morama bean tuber, and other edible tropical roots | Banana family (Musaceae): enset (Ensete ventricosum), and other edible tropical roots |
| Typhaceae family: roots of cattails and bullrushes | Nettle family (Urticaceae): edible tuberous roots including roots of ramie | Mint family Lamiaceae Livingstone potato, Plectranthus esculentus, Coleus esculentus, Coleus edulis, Hausa potato, Solenostemon rotundifolius, and other edible tropical roots |
| Cucurbitaceae family edible roots of anchote (*Coccina* sp.) and others | | |

EXAMPLE VI

Examples of Green Leafy and Other Unusual Vegetables Included in Initial Diet In one embodiment of the initial diet, any of the foods below that have been eaten more than twice per year previously, are eliminated from the diet. In a preferred embodiment, the vegetables and roots are selected from plants native to tropical Africa and Asia. In a more preferred embodiment, the green leafy or other vegetable are selected from the same family as each of the root vegetables. In a still more preferred embodiment, the green leafy or other vegetables are provided from the same plant as the starchy root vegetable.

| | | |
|---|---|---|
| Sweet potato family | Aroid family | Spurge family |
| sweet potato leaves, | Callaloo, malanga leaves, taro | (Euphorbiaceae): |
| Chinese water spinach | leaves and shoots | cassava leaves |
| Water lily family: | Water chestnut family | Mallow family: |
| edible shoots, leaves, stems | edible shoots and leaves | okra, jute |
| Arrowroot family | Palm family: | Gourd family: |
| (Marantaceae) | hearts of palm | acorn squash, chayote |
| edible shoots, leaves, stems | | spaghetti squash, guava bean |
| Carrot family: | Composite family: | Mustard family: |
| celery root, parsnip, fennel, | endive, dandelion greens, | Chinese cabbage (bok choy) |
| pennywort, rau má | burdock root | kohlrabi, turnips, mizuni |
| Goosefoot family: | Nasturtium family | Lily family: |
| beet greens, chard | nasturtium | asparagus |
| Purslane family: | Sorrel family: | Carpetweed family: |
| claytonia, winter purslane | sorrel, rhubarb | New Zealand spinach, foo yip, rau |
| Moringa family: | Valerian family: | dang |
| moringa, drumstick, chumngay | mache, corn salad, lamb's lettuce | |
| Sauris family: | Fern families | Basella family: |
| Lizard's tail, rau dâp cá | fern fronds | ceylon spinach, mong toi |
| | Legume family: | Pepper family: |
| | alfalfa sprouts, jicama | la lot, cang cua |

Selection of Animal Sources for the Instant Invention of Applicant

In one embodiment of the instant invention of Applicant, any of the meats below that have been eaten more than twice per year previously, are eliminated from the diet. In a preferred embodiment, the meats and animal proteins are selected from animals that are not the most frequently eaten and most common problem foods; thus are not selected from the bovid family, the Suidae family, and the pheasant family. In a more preferred embodiment the meats and animal proteins are selected from animals that are not the most frequently eaten and most common problem foods; thus are not selected from the bovid family, the Suidae family, and the pheasant family and are selected from animals that have been eaten more than twice per year previously. In a preferred embodiment, the meats and animal proteins are selected from animals that do not eat any food known to cause reactions for the subject. In a more preferred embodiment, the meats and animal proteins are selected from animals that are not the most frequently eaten and most common problem foods; thus are not selected from the bovid family, the Suidae family, and the pheasant family, and are selected from animals that have been eaten more than twice per year previously, and are selected from foods not known to cause reactions for the subject. In another preferred embodiment, the meats and animal proteins are selected from animals native to tropical Africa and Asia.

In a more preferred embodiment, the meats and animal proteins are selected from animals that do not eat any food known to cause reactions for the subject and are selected from animals native to tropical Africa and Asia. In a still more preferred embodiment the meats and animal proteins are selected from animals that do not eat any food known to cause reactions for the subject. In a more preferred embodiment, the meats and animal proteins are selected from animals that are not the most frequently eaten and most common problem foods; thus are not selected from the bovid family, the Suidae family, and the pheasant family, are selected from animals that have been eaten more than twice per year previously, and are selected from foods not known to cause reactions for the subject, and are selected from foods not known to cause reactions for the subject.

In one embodiment of the instant invention of Applicant, each animal source is selected from a different food family. In one embodiment of the instant invention of Applicant, each animal source is selected from a different food family, and any of the meats below that have been eaten more than twice per year previously, are eliminated from the diet. In a preferred embodiment, each animal source is selected from a different food family, the meats and animal proteins are selected from animals that are not the most frequently eaten and most common problem foods; thus are not selected from the bovid family, the Suidae family, and the pheasant family. In a more preferred embodiment each animal source is selected from a different food family, the meats and animal proteins are selected from animals that are not the most frequently eaten and most common problem foods; thus are not selected from the bovid family, the Suidae family, and the pheasant family and are selected from animals that have been eaten more than twice per year previously.

In a preferred embodiment, the meats and animal proteins are selected from animals that do not eat any food known to cause reactions for the subject. In another preferred embodiment, each animal source is selected from a different food family, and the meats and animal proteins are selected from animals that do not eat any food known to cause reactions for the subject. In a more preferred embodiment, each animal source is selected from a different food family, the meats and animal proteins are selected from animals that are not the most frequently eaten and most common problem foods; thus are not selected from the bovid family, the Suidae family, and the pheasant family, and are selected from animals that have been eaten more than twice per year previously, and are selected from foods not known to cause reactions for the subject.

In another preferred embodiment, the meats and animal proteins are selected from animals native to tropical Africa and Asia. In a more preferred embodiment, the meats and animal proteins are selected from animals that do not eat any food known to cause reactions for the subject and are selected from animals native to tropical Africa and Asia.

In a still more preferred embodiment the meats and animal proteins are selected from animals that do not eat any food known to cause reactions for the subject. In a still more preferred embodiment the meats and animal proteins are selected from animals that do not eat any food known to cause reactions for the subject and each animal source is selected from a different food family. In a more preferred embodiment, each animal source is selected from a different food family the meats and animal proteins are selected from animals that are not the most frequently eaten and most common problem foods; thus are not selected from the bovid family, the Suidae family, and the pheasant family, are selected from animals that have been eaten more than twice per year previously, and are selected from foods not known to cause reactions for the subject, and are selected from foods not known to cause reactions for the subject.

EXAMPLE VII

Example of Meats Selected for Instant Invention of Applicant

In each meat section below, each line lists foods from a different taxonomic family.

| Fowl | Fin fish: | Mammals: |
|------|-----------|----------|
| ostrich | tilapia | moose |
| duck | mahi mahi | rabbit |
|  | orange roughy |  |

EXAMPLE VII

Example of Alternate Meats Available for Initial Diet and Subsequent Diet Modifications

| Large game: | Salt water fish: | Marine non-vertebrates: |
|---|---|---|
| reindeer, elk, caribou, venison | monkfish | octopus |
| bear | oreo dory | squid |
| antelope | sweetlips | clams |
| lion | swordfish | oysters |
| kangaroo | wahoo | langastinos |
| zebra | shark | conch |
| llama |  |  |
| alligator |  |  |
| Small game: | Game birds: | Fresh water fish: |
| beaver | guinea hen | smelt |
| raccoon | Squab | walleye pike |
| turtle | goose |  |
| rattlesnake |  |  |

EXAMPLE IX

Examples of Meats Available to Add to the Diet on a Trial Basis After Achieving the Zero-symptom Baseline During initial diet expansion unusual choices for more common meats are introduced first, prior to the common members of the bovid, Suidae, and pheasant families. No food is introduced, even on a trial basis for which the subject previously experienced reactions.

| wild turkey | whitefish (salmon) | scrod (cod) |
|---|---|---|
| wild boar | halibut | turbot |

Selection of Fats and Oils for the Instant Invention of Applicant

In one embodiment of the instant invention of Applicant, any of the oils and fats below that have been eaten more than twice per year previously, are eliminated from the diet. In a more preferred embodiment the oils and fats are selected from sources that are not the most frequently eaten and most common problem foods; and are selected from sources that have not been eaten more than twice per year previously. In a more preferred embodiment, the oils and fats are selected from sources that are not the most frequently eaten and most common problem oils, and are selected from sources that have not been eaten more than twice per year previously, and are selected from foods not known to cause reactions for the subject. In another preferred embodiment, the oils and fats are selected from sources native to tropical Africa and Asia. In a more preferred embodiment, the oils and fats are selected from sources that are not the most frequently eaten and most common problem oils, are selected from sources that have not been eaten more than twice per year previously, are selected from foods not known to cause reactions for the subject, and are selected from sources native to tropical Africa and Asia.

In one embodiment of the instant invention of Applicant, each oil and fat is selected from a different food family. In a more preferred embodiment, the oils and fats are selected from sources that are not the most frequently eaten and most common problem oils, are selected from sources that have not been eaten more than twice per year previously by the subject, are selected from foods not known to cause reactions for the subject, are selected from sources native to tropical Africa and Asia, and each oil and fat is selected from a different food family.

EXAMPLE X

Examples of Oils and Fat Sources for the Instant Invention of Applicant

| Gourd family: | Rose family: | Mulberry family |
|---|---|---|
| pumpkin seed oil | Rose hip oil | hemp oil |
| Palm family: | Borage family | Laurel family: |
| coconut oil, palm oil | borage oil | avocado oil |
| Onograceae family: |  |  |
| evening primrose oil |  |  |

EXAMPLE XI

Example of Alternate Fats and Oils Available for Initial Diet and Subsequent Diet Modifications

| | | |
|---|---|---|
| Mustard family: canola oil, camelina oil | Mallow family cottonseed oil | Protea family: macadamia oil |
| Birch family: hazelnut oil | Palm family: palm oil | Rose family: apricot oil |
| Sapucaya family: Brazil nut oil | Dillenia family kiwi seed oil | Walnut family: pecan oil |
| Thea family camellia oil | Cashew family pistachio oil | Grape family grape seed oil |
| Passionflower family passionflower oil | Various animal oils: emu oil, also rendered fats from fatty meats: such as duck, bear, goose | |

EXAMPLE XII

Examples of Fats and Oils Available to Add to the Diet on a Trial Basis After Achieving the Zero-symptom Baseline During initial diet expansion unusual choices of fats and oils are introduced first. No fat or oil is introduced, even on a trial basis for which the subject previously experienced reactions.

| Flaxseed family: | Sesame family: | Walnut family: | Composite family: |
|---|---|---|---|
| flaxseed oil | sesame oil | walnut oil | safflower oil, sunflower oil |

The following are examples of diets of the instant invention of Applicant.

EXAMPLE XIII

Example Diet of the Preferred Invention of Applicant

This diet is an example of a commonly used diet of the instant invention of Applicant.

| Concentrated forms of Carbohydrates: | Oils and Fats: | Animal Protein: | Other Vegetables: |
|---|---|---|---|
| white sweet potato | pumpkin seed oil | ostrich | acorn & spaghetti squash |
| malanga | coconut oil | tilapia | bok choy kohlrabi, turnips |
| cassava | hemp oil | duck | celery root, parsnip, fennel |
| lotus | borage oil | mahi mahi | beet greens, chard |
| water chestnut | avocado oil | moose | alfalfa sprouts, jicama |
| true yam | evening primrose oil | orange roughy | endive, dandelion greens |
| arrowroot | rose hip oil | rabbit | asparagus, okra |

EXAMPLE XIV

Example Diet of the Preferred Invention of Applicant

Oil choices selected from tropical sources.

| Concentrated forms of Carbohydrates: | Oils and Fats: | Animal Protein: | Other Vegetables: |
|---|---|---|---|
| white sweet potato | pumpkin seed oil | ostrich | acorn & spaghetti squash |
| malanga | palm oil | tilapia | bok choy kohlrabi, turnips |
| cassava | hemp oil | duck | celery root, parsnip, fennel |
| lotus | camelina oil | mahi mahi | beet greens, chard |
| water chestnut | avocado oil | antelope | alfalfa sprouts, jicama |
| true yam | camellia oil | orange roughy | endive, dandelion greens |
| arrowroot | rose hip oil | rabbit | asparagus, okra |

EXAMPLE XV

Example Diet of the Preferred Invention of Applicant

Vegetable choices of tropical origin.

| Concentrated forms of Carbohydrates: | Oils and Fats: | Animal Protein: | Other Vegetables: |
|---|---|---|---|
| white sweet potato | pumpkin seed oil | ostrich | acorn & spaghetti squash |
| malanga | palm oil | tilapia | bok choy, mizuni |

| Concentrated forms of Carbohydrates: | Oils and Fats: | Animal Protein: | Other Vegetables: |
|---|---|---|---|
| cassava | hemp oil | duck | celery root, penny wort, rau ma |
| lotus | camelina oil | mahi mahi | Lizard's tail, rau dap ca |
| water chestnut | avocado oil | antelope | asparagus |
| true yam | camellia oil | orange roughy | ceylon spinach, mong toi |
| arrowroot | rose hip oil | rabbit | okra |

EXAMPLE XVI

Example Diet of the Preferred Invention of Applicant

Vegetable choices from the same plant as the complex carbohydrate, when possible.

| Concentrated forms of Carbohydrates: | Oils and Fats: | Animal Protein: | Other Vegetables: |
|---|---|---|---|
| white sweet potato | pumpkin seed oil | ostrich | sweet potato leaves |
| malanga | palm oil | tilapia | malanga shoots |
| cassava | hemp oil | duck | cassava leaves |
| lotus | camelina oil | mahi mahi | lotus leaves, blossoms |
| water chestnut | avocado oil | antelope | asparagus |
| true yam | camellia oil | orange roughy | jute, okra |
| arrowroot | rose hip oil | rabbit | arrowroot shoots, leaves |

EXAMPLE XVII

Example Diet of the Preferred Invention of Applicant

Increased fat from animal sources.

| Concentrated forms of Carbohydrates: | Oils and Fats: | Animal Protein: | Other Vegetables: |
|---|---|---|---|
| white sweet potato | emu oil | ostrich | sweet potato leaves |
| malanga | palm oil | tilapia | malanga shoots |
| cassava | rendered duck fat | duck | cassava leaves |
| lotus | camelina oil | camel | Lotus leaves, blossoms |
| water chestnut | avocado oil | antelope | asparagus |
| true yam | camellia oil | guinea fowl | jute, okra |
| arrowroot | rose hip oil | rabbit | arrowroot shoots, leaves |

EXAMPLE XVIII

Example Diet of the Preferred Invention of Applicant

Other tropical roots selected as carbohydrate sources; animals selected that are not grain-fed.

| Concentrated forms of Carbohydrates: | Oils and Fats: | Animal Protein: | Other Vegetables: |
|---|---|---|---|
| Hausa potato | pumpkinseed oil | bear | sweet potato leaves |
| Dasheen | palm oil | tilapia | malanga shoots |
| Enset | hemp oil | lion | cassava leaves |
| Florida arrowroot | camelina oil | mahi mahi | lotus leaves, blossoms |
| African yam been root | avocado oil | moose | asparagus |
| Guinea yam | camellia oil | orange roughy | jute, okra |
| Chinese potato | rose hip oil | shark | arrowroot shoots, leaves |

EXAMPLE XXIX

RESEARCH STUDY: Instant Intervention Methodology in Difficult and Complex Cases

Summary Of Investigation: Difficult and complex cases are those in which a subject experiences a myriad of moderate to severe symptoms from foods and multiple chemical sensitivities, sensitivities to pollens, dusts, molds and the like. These sensitivities also contribute to reduced resistance to infections, Candidiasis, irritated and injured mucous membranes of the GI tract causing a variety of malabsorption problems, and anxiety and fears of the subject associated with past exposures and misinterpretations by the subject. For these subjects, cause and effect assessments are difficult, and helpful approaches for one condition often causes adverse effects for another condition, making the desired progress for these subjects more difficult to achieve.

The purpose of the investigation was to 1) further document a highly effective stepwise, systematic approach for complex, difficult cases, and 2) to show that this stepwise, systematic approach can be broadly applied to a large group of varied cases.

Each person accepted into the study, met the following criteria:
1) Physician diagnosis as difficult and complex.
2) Physician diagnosis of food allergies, sensitivities or intolerances as an important factor.
3) Subjects each agreed to fully comply with the requirements of the study; including compliance with the diet provided, and with all subsequent recommendations. In addition to instructions provided in a subject handbook, additional individualized instructions were be provided orally. Subject agreed to participate in a weekly telephone consultation for the first two months and monthly consultation for the subsequent 5 months.

Subjects proceeded through a stepwise treatment program that scientifically controls variables and achieved a symptom-free diet within the first two months and achieved a full zero-symptom baseline by the end of the six-month program for all sensitivities. When participants were ready to expand their diets, assistance was provided to help participants choose foods that were likely to be well-tolerated. Staff also instructed the participants on food reintroduction methods. A subject's final diet was achieved that maintained the zero-symptom status of the subject.

Prior to the beginning their diet, each subject was asked to prepare a comprehensive list of all symptoms and complaints they had experienced in the last 2 months without regard to whether-or not they felt the symptoms were related to allergies, sensitivities or intolerances. The subject was then asked to rank each symptom on a scale of 0-10, with 10 being the most severe a reaction could be experienced, with 2 being the lowest level a symptom can be experienced with certainty that it is still present, 1 being unable to tell whether a symptom is present, and a score of '0' being certain the symptom is absent. At intervals of 1-2 weeks thereafter, each subject was asked to rank the symptoms being experienced at that moment, according to the same scale. Each participant was used as a self control; the symptom rankings obtained initially for each individual represented the symptom levels each subject had experienced for the previous 6 months. The changes in symptom levels during the 6 months prior to entering the Special Foods Intervention Program and the treatment approach during this time are compared to the results achieved with the Special Foods Intervention Program.

Subjects: Case studies are described herein for 16 individuals. Six additional subjects enrolled but did not start or stopped within the first week. A total of 50 participants are currently enrolled in and proceeding through the research program. Approximately 50% of participants were referred by their physicians; the remaining 50% were self referred with physician approval. Approving physicians represented a wide array of specialties—pediatricians, gastroenterologists, dermatologists, internists, neurologists and are from a wide array of organizations—private practice, major medical centers, and HMO's. Nine of the 16 cases are severe and complicated cases ranging from severe eczema, seizures, various cases of severe digestive problems, and a variety of conditions all caused by underlying food, chemical and environmental sensitivities. All of the adults in the study have been ill for many years. The remaining seven cases are autistic children. Each participant had received at least one of the following prior diagnoses: leaky gut, Candidiasis, fatty acid imbalance, levels of mercury, heavy metals, or pesticides, and a variety of biochemical imbalances. Every participant had previously tried other dietary approaches and many supplements.

Summary Of Results: Results are reported for cases ranging from 1 month to 10 months, and one case is described for 28 months. The latter describes an individual who began the diet with minimal guidance, much of which was not followed. After two difficult years, they entered the intervention program, followed through with the suggestions provided initially and achieved the dramatic improvement they were seeking.

Of the 16 cases reported herein, 8 achieved an 80% or greater improvement in overall symptoms. This is value was determined by averaging the percentage improvements reported by the subject for each symptom. By the method of scoring used, this means that 8 individuals reported that the average level of their symptoms was reduced to such a low level that they were barely able to discern any symptoms. Time required to achieve this low symptom level varied from 1 to 6 months with a mean of 2.8 months. The remaining cases all showed continuing declines in symptom levels, and none of these had yet achieved a steady state symptom level. Thus symptom levels in each of the remaining 8 cases are likely to continue to decline further.

Some symptoms were completely eliminated in every participant in the study. Symptoms showing essentially complete elimination were constipation, diarrhea, and eczema. Selected individual symptoms were tracked across all participants. Of the 5 individuals reporting congestion, after 2 months, the congestion was reduced to an average of 14 percent of it's original level; 4 subjects reported a complete elimination of congestion and 1 reported a 71% reduction in congestion. Of the 8 individuals reporting constipation, all 8 subjects report normal bowel function after one week. There were 13 subjects reporting problems with diarrhea. The average percent improvement for all 13 by the end of the first week of the instant invention program of Applicant was is 68.5%. For the 10 subjects who have been participating in the program over 1 week, the average reduction in diarrhea is 83.4%. By the method of scoring used, this indicates that all 10 individuals experienced a symptom reduction to such a low level that they were barely able to discern whether the diarrhea existed.

Three of the participants studied experienced complete relief from all symptoms through dietary intervention alone. The remaining 13 participants required exposure reductions related to mold, chemical sensitivities, pollen and so forth, 5 of these achieving symptom-free status so far. In most of these cases the sensitivities were complex and extensive. Complete elimination of food-related symptoms made accurate assessments of cause/effects in these other areas possible.

Emotions, particularly anxiety, were found to be an important factor in two cases; however in all cases as participants began to see the cause and effects and experience significant symptom-relief, there was a noticeable relief and they were much calmer.

Some persons in the study were suffering severe, debilitating symptoms, including seizures and loss of muscle tone. In every case, these individuals experienced dramatic improvements, however, much longer time periods are required for these individuals to recover, due to the severity of the damage. Participants experiencing hypotonic muscle tone, for example, are experiencing a steady, continuing improvement in muscle tone; however return to normal function will require several additional months. In 2 cases some of the damage was severe enough that permanent damage has occurred. One of these cases, a child suffering from many severe seizures each day, became seizure-free after 5 months of treatment.

Figure 2:
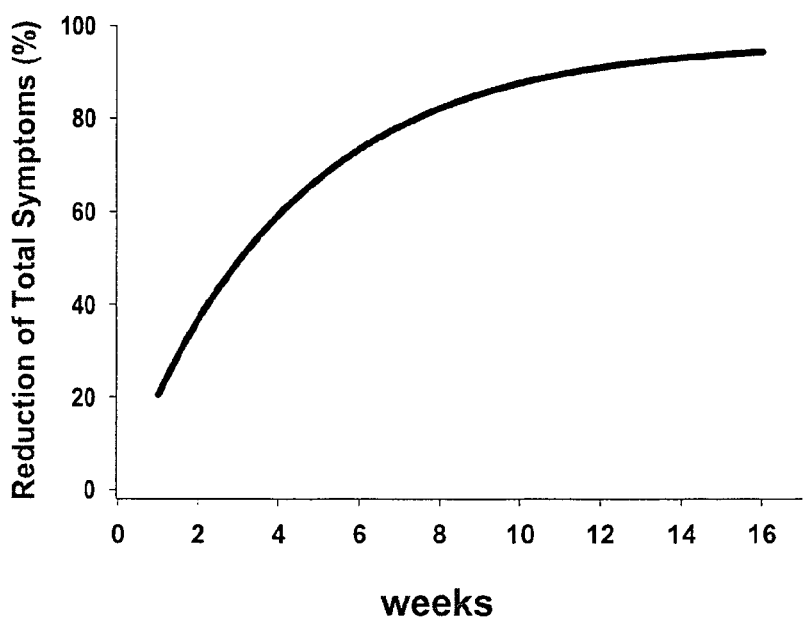
FIG. 2 is a graph showing reduction of total symptoms.

FIG. 2 shows a reduction in average symptoms reported by the subjects for all participants in the study.

Example Case Study I. Fatigue, Diarrhea, Anxiety

Figure 3:
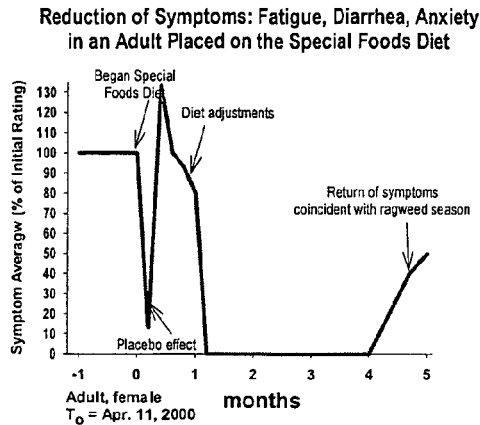
FIG. 3 is a graph showing reduction of particular symptoms in an adult placed on the special foods diet.

Case Summary: FIG. 3 shows the improvements in symptom averages for an adult experiencing fatigue, diarrhea and anxiety. Emily entered the research program in April of 2000 with an exasperating case. Emily had suffered for many years from several food-induced ailments including diarrhea, stomach grumbling, and intestinal cramps; she was also debilitated with severe fatigue that limited most activities. In addition, because her diarrhea was so severe, Emily was losing a lot of fluids. For years Emily had been unable to leave her home. Emily had also been unhealthily thin all of her life. She had tried numerous treatments from a variety of clinics and found nothing to help her.

After just three days on her diet, the initial step of the instant invention program of Applicant, Emily showed phenomenal improvement. All of her previous symptoms were virtually non-existent. Her intestines had quieted, and she had little or no bloating caused by gas. She no longer suffered from the cramping that had pained her just a short time ago. Emily was excited about the change and confident of a full and immediate recovery.

Unfortunately, Emily's condition relapsed during the second half of the first week of her diet. Her ailments had returned stronger than before. This sudden reversal led the research investigator and counselors to believe that the initial improvements were the results of a placebo effect. Prevalent more so in adults than in children, this effect is based on the subject's expectation that the treatment will cure them completely. That is, the brain suggests to the body that the symptoms are cured and the body follows suit. This effect is a faulty representation of recovery and must be disregarded as a step taken towards true recovery.

By the end of the third week on the program, Emily noticed a change many experience on the diet—she became more smell sensitive. She also felt very tired, and spent much of her time in the bathroom with her persistent diarrhea. Because these relapses predominantly occurred during the second half of the week, the research investigator and counselor reexamined Emily's diet looking for possible "problem foods." In addition, the research investigator and counselor observed the presence of pollen sensitivities. The research investigator and counselor advised her to keep pollen contact to a minimum. Emily's symptoms due to pollen sensitivities were eliminated easily.

At the end of the fifth week, it became obvious that the removal of the last "problem foods" from the diet had yielded positive results. Emily's symptoms displayed a steadier overall decline as opposed to the sudden drop caused by the placebo effect. She now had normal stools, experienced no intestinal cramps, and was generally more upbeat and lively. The research investigator and counselor speculated that any additional problems were anxiety related.

Emily was symptom-free for months! The focus of the program has shifted toward maintaining this zero-symptom trend. Both Emily and her husband are amazed with the improvement. Emily has been cleared to eat as much from the diet foods as she wants, in order to gain weight. She has been advised to exercise regularly to build up conditioning. With a surge of renewed energy, Emily has begun to travel, enjoying her first vacation in years. On September $23^{rd}$ she and her husband will be featured in a song and dance festival. She is handling a grueling practice schedule with ease.

During pollen season this fall, Emily has experienced a partial return of symptoms. This was expected since Emily was doing so well that she simply forgot to return to the pollen protection procedures she was advised to use in the spring. She has been taking long daily walks outside during ragweed season, running and playing with her son. Because her symptom-free status had been maintained for months, the appointments were occurring about every 6 weeks, and so the partial return of symptoms was not observed quickly by her research investigator and counselor. Immediately after her dance and song performance Emily will be carefully following her pollen prevention procedures, and her symptoms are expected to quickly disappear.

Approach:

Emily came to the Instant intervention program of Applicant hoping to cure herself of the bothersome diarrhea and fatigue that had plagued her for some time. Through instant intervention program of Applicant, there was implemented a strict, well-balanced diet, eliminating the foods responsible for her irregular bowel movements. Along with these dietary measures, Emily was advised to chew her food slowly and thoroughly and to drink plenty of water. As the frequency of her diarrhea diminished, appearing only a few scattered days of the week so did her fatigue. Now, individual food testing could be carried out, identifying "problem foods" to be removed and replaced. With this new agreeable diet, Emily feels 'like a new person' and can now lead a normal life.

1. Dietary Considerations

A. Elimination of Harmful Foods: The degree of success of the dietary program relies largely upon the removal of the foods responsible for the flaring-up of symptoms. The instant invention program of Applicant is then used to analyze the nature of these reactions. Once the "problem foods" are singled out, they are replaced with nutritious substitutes that cause no reaction.

B. Elimination of Retarding Supplements: Emily used to market certain dietary supplements. In addition to being exposed to them on a daily basis, she consumed them regularly as a part of her diet. For two years, Emily used these herbs thinking that they could only yield positive results. They most likely had the opposite effect, minimizing the power of the Diet and forming a chemical dependence.

2. Environmental Considerations

A. Avoid obvious chemical exposures: The instant intervention program of Applicant aims to seek out and eliminate the allergic reactions caused by certain foods in a subject's diet. Once this issue has been resolved, the focus switches to the revealed environmental sensitivities. In most cases specific considerations are dealt with, but there are also universal pollutants that should be avoided by everyone. The research investigator and counselor familiarized Emily with these chemicals and offered methods to limit her contact with them.

B. Pollen: Some of Emily's digestive symptoms, apparent after the third week of treatment, and again in August and September resulted from a sensitivity to pollen. The symptoms of diarrhea and fatigue experienced in August and September were entirely due to pollen exposures. Pollen exposure and associated symptoms were completely eliminated in the spring and similar results are expected this fall.

Example Case Study II. Extensive Food Allergies, Chemical Sensitivities

Figure 4:
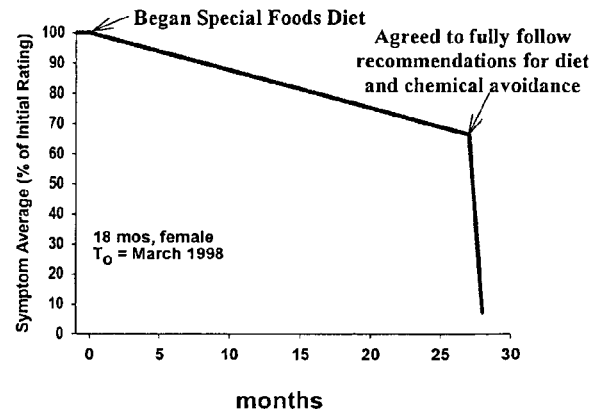
FIG. 4 is a graph showing reduction of particular symptoms in an adult placed on the special foods diet.

Case Summary: FIG. 4 shows the improvements in symptom averages for a child experiencing extensive food allergies and chemical sensitivities. Caroline first contacted the instant intervention program of Applicant in 1998. At 18 months, her daughter, Anne, suffered from extensive food allergies. Constantly bloated and nauseous, Anna had very frequent loose and bloody stools. Her constant stomachache and overall discomfort made her generally irritable and fatigued. To Caroline, Anna's eyes looked glossed over; she always seemed distant, withdrawn, and "zoned out." Anna's face was covered with a severe eczema-like rash and she always had dark circles and puffiness under her eyes. Furthermore, Anna had frequent ear infections and red, hot feet. Also, Anna was often extremely thirsty, but due to her bed-wetting habit, Caroline was hesitant to give her many liquids.

Anna was one of the first customers to be placed on the instant invention program of Applicant. After 27 months, her overall symptom level dropped by over 40 percent. Her eczema was almost 70 percent clear. Her diarrhea and frequent ear infections had also declined. With these physical improvements, Anna was also less withdrawn and more alert.

During this time period, Caroline contacted The Applicant periodically for serving suggestions or cooking techniques. Due to this limited involvement of the staff, Anna's progress was significantly hindered. Specifically, the research investigator and counselor's suggestion to end trips to public places was consistently rejected by Caroline. As a result, Anna's immune system continued to be subjected to chemical and environmental sensitivities. In addition, Caroline varied Anna's foods quite a bit, without consulting the staff. By the end of the 27 month period, Anna's diet had decreased to an ineffective 3-day rotation. Consequently, Anna had developed sensitivities to many of the diet foods, as well. Regretfully, Anna has lived with food allergies over two years longer than necessary. Once Caroline finally agreed to follow the research investigator and counselors' recommendations, Anna showed immediate and drastic improvement. A new 5-day rotation diet was put into action, minus arrowroot and other allergenic foods. Finally, the trips to church and stores were ended. Within just one month of the new regulated diet, Anna's symptoms have decreased to 7.3 percent of her original condition, and then the next month to an overall symptom ranking of 0.1.

This essentially complete elimination of symptoms was the result of a strictly controlled rotation diet of unusual foods, as recommended by the staff, eliminating her exposures to environmental chemicals. Now at age four, Anna is finally ready for dietary expansion.

Approach: Officially, Anna began the Instant diet in 1998. Although a strict 7-day rotation diet was set up, her mother rearranged the foods without consulting the staff. Therefore, This investigator had limited involvement during the first 27 months of Anna's diet. Furthermore, the recommendation for the termination of Anna's exposure to chemical and environmental irritants of church and stores was consistently rejected. As a result, only a 40 percent reduction symptoms occurred. In addition, an ineffective 3-day rotation of the foods caused Anna to develop sensitivities to several of the unusual foods. During the 28th month, Anna's mother finally agreed to follow a 5-day rotation diet of the remaining non-allergic foods and consented to limit Anna's exposure to environmental sensitivities. As a result, the overall symptom level dropped 92.7 percent. At the moment, Anna's diet is being held at this stable and comfortable level in order to allow her body to adjust. Once her system has "healed," Anna will finally be ready to begin dietary expansion.

1. Dietary Consideration: Developed Sensitivities to Diet Foods: Due to improper rotation of the new diet foods over the initial 27 month period, Anna developed sensitivities to the unusual foods. At the start of the 28th month, her diet was redesigned to allow a 5-day rotation of non-allergenic foods.

2. Environmental Considerations: Over the course of 27 months, numerous environmental sensitivities were suspected. Due to her intolerance of chemical fumes from polyesters and plastics in particular, it was suggested that Anna be kept away from stores, church, and other public places. These recommendations were rejected during the first 27 months. Consequently, Anna's system continued to be exposed to irritating chemical compounds. Once Anna's mother finally agreed to limit such exposures, the symptom level dropped dramatically.

Example Case Study III. Constipation, Bloating, Severe Pain, Leaky Gut, Fatigue

Figure 5:
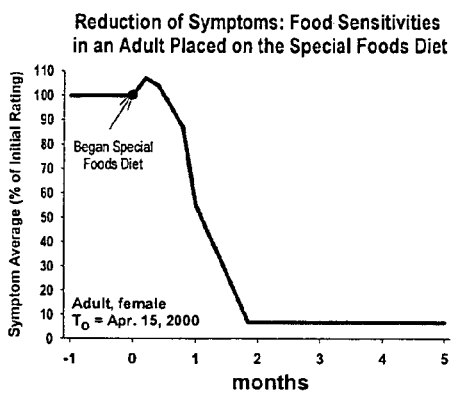
FIG. 5 is a graph showing reduction of particular symptoms in an adult placed on the special foods diet.

Case Summary: FIG. 5 shows the improvements in symptom averages for an adult experiencing constipation, bloating, severe pain, leaky gut, and fatigue. For 41 year-old Susan, food sensitivities and trial treatments were nothing new. After contracting an unusual virus 4 years ago, she developed an autoimmune complication that impacted all areas of her life. Aside from excruciating lower gastro-intestinal pain caused by leaky gut syndrome, Susan also suffered from persistent bloating, constipation and gas. Her general feeling of sluggishness was intensified immediately after eating—she truly could not keep her eyes open.

Although Susan had been following a strict diet for several years, her symptoms showed no signs of improvement. Despite her conviction that eating beef or poultry would make her ill, her hitherto vegetarian diet had not brought her any substantial relief. Neither her digestive debilitation nor her energy deficiency had improved over the years since developing this autoimmune disorder. This investigator tailored a diet to accommodate her concerns; her rotations consisted of seven types of fish, which she was instructed to eat in relatively small quantities.

As with her previous diet programs, Susan experienced an unpleasant withdrawal period that lasted for about 2 weeks. However, at the end of four weeks on the diet, her symptoms had dropped nearly 10 percent from her original condition. Although she was experiencing increased acid reflux problems, her lower gastro-intestinal pain had decreased and the occurrence of her severe fatigue spells had disappeared. A week later, following a colonic irrigation procedure, her overall symptom rating was cut in half. She reported that she was feeling "great!"

It was at this time that Susan mentioned a possible allergy to pollen. This investigator advised her about protective measures against pollen and mold exposures. By eliminating her food-related problems, environmental sensitivities could become more easily discerned.

By the eighth week, Susan had achieved a fantastic drop in symptoms. Now at under 7 percent of her original condition, her gastro-intestinal problems have disappeared! Additionally, her energy has increased ten-fold: her previous sluggishness is no longer a problem. Her previous food cravings are also a thing of the past. This outstanding improvement has remained consistent for months. With Susan's symptoms held at near zero-symptom level, she is now beginning dietary expansion. This investigator is thrilled about Susan's outstanding results and looks forward to her continued progress.

Approach: Susan's debilitating condition, characterized primarily by severe lower gastro-intestinal pain and fatigue, was symptomatic of food allergies. Her aversion to beef and poultry required a rotation diet consisting of several types of fish. After the initial two-week withdrawal period, Susan's symptoms showed a rapid decline. After just 2 months on the Instant diet, Susan's condition was a mere shadow of the initial condition. She has maintained this low level and is making steps toward dietary expansion.

1. Dietary Consideration: Susan's concerns about her reactions to beef and poultry required a diet consisting of several types of fish. Although she was reluctant to eat meat of any kind, this diet resulted in a dramatic decrease in symptoms after just 2 months on the program.

2. Environmental Considerations: As Susan progressed on the Instant invention program of applicant, she began to wonder about a sensitivity to pollen and mold particles. With the elimination of her problem foods, such an observation of environmental exposures could be more legitimately determined, and the proper steps to eliminating such exposures were given to her.

Example Case Study IV. Severe Eczema, Hyperactivity

Figure 6:
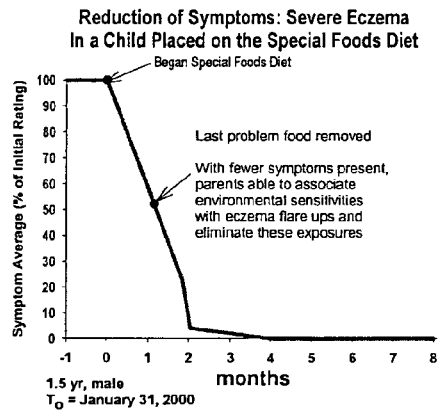
FIG. 6 is a graph showing reduction of particular symptoms in a child placed on the special foods diet.

Case Summary: FIG. 6 shows the improvements in symptom averages for a child experiencing severe eczema. When Spencer's mom called the instant intervention program of Applicant, it was as a last resort. At 13 months old, Spencer already had a variety of medical problems. He had trouble eating, and was only in the 25th percentile on the growth chart. He didn't sleep well at night and although he had a charming personality, he was in constant pain. Worst of all was the eczema. Since he was two months old, Spencer had been suffering from severe eczema covering 75% of his total body surface. This eczema had not responded to any treatment. A picture of Spencer at a year old shows a brave little boy, smiling cheerfully through a face covered in a painful rash. As well as swollen, puffy eyes, Spencer also had a horseshoe shaped patch of bright red, raw sores spreading from his mouth and chin up to both of his eyes; and the rest of his body looked much the same. His chest, upper arms, thighs, and neck all had severe patches of eczema. It is very hard to imagine how this little boy could still be smiling.

In an effort to help the eczema, Spencer's mom was almost exclusively breastfeeding. She had eliminated all but red meats and vegetables from her diet. Spencer was on a hunger strike and refused to eat any solid foods. Not only was Spencer not growing, but his constant nursing and her limited diet was causing his mother to lose weight. For 10 months Spencer had been treated using a wide variety of medical approaches. The consistent diagnosis his parents received was that severe food allergies were the basis for his eczema, but the medical experts advised that there would be no foods Spencer would tolerate. Spencer's parents began looking for an approach that emphasized dietary intervention. They found The instant intervention program of Applicant and began the dietary intervention process with the help of the staff.

Spencer's mom was planning on continuing to breastfeed. This meant that both she and Spencer needed to go on the diet. To eliminate confusion in evaluating symptoms, Spencer was breastfed exclusively for the first six weeks. This removed the problem of accurately correlating symptoms due to the delay of food absorption in his mother's body. The initial diet was basically the standard Instant invention program of applicant, modified by eliminating coconut oil and some of the vegetables. Spencer continued to be bathed in therapeutic bath oils that his mom felt helped avoid infection and improve the eczema. Other than the bath gels, Spencer and his mom followed the diet and other requirements with no compromises. After three weeks, startling results were already apparent. 55% of Spencer's skin surface was clear. The improvement showed no signs of stopping. Spencer's mom had noticed that on day 1 of the diet, known as white sweet potato day, Spencer seemed to be having outbreaks, and she developed a rash. There were a variety of possible culprits for the outbreaks. It could have been the white sweet potato, ostrich, hemp oil, kohlrabi, or turnips. Because of the delays inherent in breast-feeding, testing these items individually seemed like a poor idea. Instead we dropped them down to a six-day diet, completely eliminating the white sweet potato day. At this point we realized we would probably go beyond our five-week time frame to find the perfect diet for them.

A week later we got a call from Spencer's mom. She was concerned that Spencer had eaten dirt. Was there anything in the dirt that he might react to? Although dirt was not our first choice in food, this was a fabulous sign. Spencer was feeling good enough to get into everything, like a 14 month old should. His mom reported that his skin was about 70% clear, with his face clearing up last. The healing process was occurring all over his body. He was happier, and much more interested in playing and having fun.

As the clearing continued, the negative effect of the skin gels was becoming apparent. Before his baths his skin would be very clear, but within minutes of getting out of a treated bath his back, arms, and neck would be red and blotchy. Spencer would also scream as his mom approached him with the gels and lotions. As well as eliminating the bath gels and lotions, we suggested that they make sure his bath water was free from chlorine and other organic compounds. Spencer's mom was concerned that his skin would get too dry without the lotions. We felt that when his skin became normal the gels would not be necessary, just wait and see.

At the end of five weeks Spencer's eczema appeared to be on the road to recovery. His skin was about 85% clear. The best part was, that without the constant general symptoms, it became possible to tell what other things he was reacting to. A hug from his dad in a wool sweater, the babysitter's shampoo, air from the heat pump; these were all triggers to outbreaks in the little boy.

At six weeks the eczema was 95% gone. At nine weeks it was 99% gone. It is amazing to compare pictures of Spencer from before the diet and now. The smile and charm are the same, but he looks so much healthier. His mom is excited because this is the best he's looked in a year. Spencer has been reintroduced to solid foods, and is eating well.

The next step for Spencer and his family was to focus on environmental issues. It is obvious that at least part of Spencer's problems were with fumes he's inhaled (paints, perfumes and cigarette smoke) and fabrics he's touched. After these environmental issues were addressed, the process of food reintroduction began.

One or two foods were introduced each week, with sufficient time between foods to allow for complete recovery from any symptoms the previous food caused. Spencer displayed minor temporary eczema and diarrhea relapses. The onset of Spencer's teething has instilled the desire not to eat, but he has been cleared to eat as much as he wants in hopes of stabilizing his weight. His eczema however is virtually non-existent! The research investigator and counselor is now concentrating on maintaining these current results, and dealing with each instance of symptom flare-up individually as they appear. Spencer's final, expanded diet will allow him to maintain a healthy, pain-free life.

Approach: Spencer was found to be suffering from a combination of food allergies and environmental allergies. Providing him relief was a two-step process. First his symptoms due to food allergies had to be eliminated using the Diet. Because food reactions can present so many symptoms, it was hard to identify what his other allergies were as long as the food sensitivities were present. A careful dietary intervention eliminated these symptoms, allowing his parents to begin to recognize cause and effect associations with environmental exposures. Once these associations became easy to see, The research investigator and counselor assisted Spencer's parents in extrapolations based on the chemical compositions of the environmental exposures. Using these categories of irritants, effective environmental avoidance strategies were developed to eliminate Spencer's exposure.

1. Dietary Consideration

A. Accidental Starvation (both Spencer and his mom): Spencer and his mom were both not eating enough. Spencer's lack of calories showed in slowed growth, his mother's was apparent with her weight loss. As limited as their diet had become, it was hard for them to get all the calories they needed. This is an important cause of declining health and proliferating food sensitivities. By providing them a well-tolerated diet with variety and sufficient calories, this problem was solved.

B. Problems with Day 1 of the diet: In other situations, it is best to test individual foods at each meal. Because of the delay caused by nursing, this was not possible. Total elimination of the day was the approach that was selected.

C. Proliferation of Sensitivities: Before entering the Instant Intervention Program the diet of Spencer and his mother had become increasingly limited; Spencer's sensitivities were becoming more severe. A new diet was necessary to alleviate this increase in sensitivities. The lack of sufficient calories in Spencer's diet and frequent eating of foods closely related to his poorly tolerated foods had led to the proliferation of his food sensitivities.

2. Environmental Considerations

A. Cloth fibers (wool, polyester, etc.: Spencer's sensitivity to synthetic fibers and wool became very apparent during the fourth and fifth week. A hug from a person wearing wool was enough to begin a flare-up of the eczema. His clothes were changed to 100% cotton, as were sheets and other materials. His bed was wrapped in foil underneath all cotton sheets.

B. Combustible fumes (cars, heaters, cigarette smoke, etc.): The residue of smoke on his babysitter's clothes was enough to start an outbreak in his sixth week. His parents are adjusting their work schedules to avoid leaving him with anyone whose clothes and fragrances they cannot control. Spencer has to avoid gas stations and exhaust fumes. The gas heat in his house caused an immediate breakout when it kicked on in the sixth week. His house has been shifted to electric heat, with space heaters. His parents will isolate two rooms of the house that are Spencer friendly. A cotton sheet hanging over the window will allow the fresh air in while keeping the pollen out.

C. Chemical contamination (paint thinner, paint, solvents, personal care product, fragrances, etc.): A basement renovation project coincided with the onset of Spencer's symptoms at 2 months. Much of the renovation dust is still present. To avoid all of the dust and chemicals; Spencer's parents were advised to completely isolate the basement from the rest of the house. All paints and solvents have been removed from the house. Pure sodium carbonate based soap is now used on Spencer's clothes and on his body. Bath gels and lotions have been completely eliminated from his routine. Spencer avoids trips to the dry cleaner and fabric stores. Wal-mart specifically appears to be a problem for him, possibly a chemical used to preserve the clothes. Spencer's parents now avoid taking him in to the store, as well as avoid the use of any products purchased from there.

Example Case Study V. Eczema, Severe Pain, Sleeping Difficulties

Figure 7:
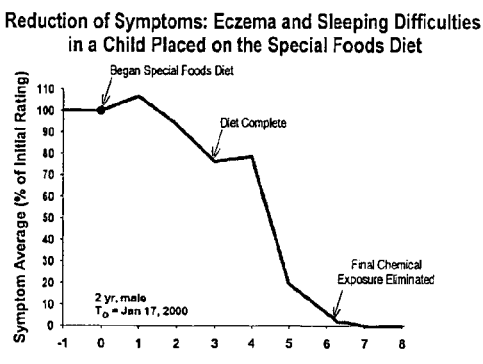
FIG. 7 is a graph showing reduction of particular symptoms in a child placed on the special foods diet.

Case Summary: FIG. 7 shows the improvements in symptom averages for a child experiencing eczema and sleep difficulties. Leslie contacted The instant intervention program of Applicant seeking help for her two year-old son, James. He suffered from terrible eczema breakouts behind his knees and elbows.

Unable to speak, James expressed his great pain through his constant screaming, crying and whimpering. His skin condition clearly caused him great irritation throughout the day, as he would constantly attempt to scratch the affected areas.

James's discomfort lasted into night, making sleeping very difficult. His trembling and jerking as he fell asleep was extremely disconcerting. At the slightest noise or movement, young James would startle awake with fear; getting him to go back to sleep was next to impossible. For comfort, the two year-old would engage in prolonged nursing and continued his pitiful weeping.

Still nursing, Leslie had tried to feed her son many different foods. Unfortunately, once she found a food that he tolerated, she restricted the diet to just those foods. Without proper rotation, James quickly became allergic to all of them as well. It was clear that these dietary changes were simply ineffective. Then Leslie heard about the instant intervention program. Because Leslie was still nursing, both mom and child were placed on the strict diet.

After four weeks on the Diet, James had not shown much improvement. His eczema had gotten worse and the persistent sleeping difficulties seemed to have become more intense. Leslie mentioned that a similar reaction occurred earlier that year when James was placed on a homeopathic remedy program using diluted oils. Then, after one week without the oils, Leslie reported that the oil-related symptoms were gone.

By the two-month checkup, James's eczema was improving. More specifically, it became easier to distinguish between individual flare-ups: rather than being a constant problem, the eczema seemed to come and go. The cause? Leslie noticed that whenever James had direct contact with plastic, the eczema seemed to get worse. For example, on Days 1, 4 and 5 of the seven-day rotation his food was wrapped in plastic and the eczema flared. However, on Days 2 and 3, when there was no plastic, his eczema seemed to fade. With the food problems now eliminated and his diet under strict control, his environmental sensitivities could be more easily identified and eliminated.

Moreover, by evaluating the rest of the home environment, it was clear that the pervasive volatile compounds throughout the house created a perfect environment for the terrible eczema condition. The air was filled with the fumes from the gas heating system and a HEPA filter was releasing chemical residue into the air. With the garage located just off the kitchen, fumes from paints and chemical solvents were seeping into the area where food preparation was taking place. In addition, James played with plastic toys on a floor covered with interlocking foam/plastic squares.

The research investigator and counselor recommended the removal of all plastic materials and scented items from James's immediate environment. The research investigator and counselors also suggested that Leslie use electric space heaters instead of the gas heat and that the HEPA filter be removed. Leslie was also asked to air out the house during rainstorms and to check the water system for carbon filters. It was also recommended that James's foam bed be covered in aluminum foil and all bedding be changed to cotton. Leslie also dressed James in long-sleeved shirts and pants to try to keep his furious itching to a minimum.

Two weeks later, Leslie reported that James was doing well. He was nursing frequently and seemed to enjoy eating small amounts of the new foods. Leslie noticed that he was even starting to feel heavier and had lost his previous sickly-thin appearance. With the gas heat replaced by electric space heaters and the plastics removed, James appeared to be almost completely cleared of his eczema.

With the diet under control, environmental irritants truly seemed to be a great source of James's problems. When Leslie took James to visit his grandparents, he immediately started wheezing upon entering the house full of perfumed items and gas heat fumes. Leslie was even more convinced of his environmental sensitivities when she used the gas oven during James's nap and he woke up screaming with worsened eczema behind his knees and elbows. Even a ten-minute ride in a plastic shopping cart sent him into hysterics; he continued to scream and scratch his affected areas into the night. With more time spent playing outside, James also began to display intolerance to pollens. The research investigator and counselor suggested several protective measures, including putting a bandana over his nose and mouth when outside and getting him to play in the sandbox instead of on the grass.

By the fourth month, James finally seemed able to sleep almost peacefully. There was no more wailing, flailing or scratching misery. If he did wake up, he fell quickly back to sleep. During the day, James's behavior was also noticeably better: he was not as easily agitated, much more subject and able to sit still. Although he still had ups and downs, the cause of each flare-up could be tied to each of the particular reactions. This would not have been possible without the controlled diet. With environmental sensitivities continually being identified and eliminated, James's symptoms were set on a downward trend.

Two weeks later, Leslie had very good news to report! James had weaned very quickly and was a brand new person. Now sleeping straight through the night, he was relaxed during the day and had a happy and cheerful attitude. With most of his pain gone, the last hurdle was to clear his eczema once and for all.

Leslie and the research investigator and counselors continued to identify and eliminate possible environmental sensitivity exposures. By the 28th week, James's eczema finally seemed to clear. Leslie reported that that the skin behind his knees was no longer red or pink, but just slightly rough. The spots on his elbows were now the correct flesh color. Best of all, without the need to scratch these irritated areas, he was able to sleep comfortably and peacefully.

From now on, the goal is to maintain this zero symptom level. By continuing to protect James from pollen, plastic and other environmental exposures, his immune system can rest and recover. This investigator expects that once his improved condition becomes completely stable, James will be able to enjoy an expanded diet, and will eventually make a full recovery.

Approach: Nursing mom Leslie had tried several dietary changes to no avail. Both Leslie and her son, James, were placed on a controlled rotational diet that sought to effectively eliminate any possible problem foods. It was predicted that once his painful eczema flare-ups were healed, James's sleeping difficulties would also disappear. Through careful and systematic evaluation of James's home environment, it was quickly discovered that external chemical factors were largely responsible for his eczema breakouts. With the diet under control, the specific cause of each of the incidental flare-ups could be more easily discerned. As each environmental sensitivity exposure was eliminated, James's symptoms decreased. Once James was weaned, he was able to sleep relatively comfortably and soundly and the eczema soon faded. The goal now is to maintain the zero-symptom level while expanding James's diet to more common foods.

1. Dietary Consideration

A. Avoiding Foods from Previous Exposures: Because Leslie had already tried various alternative dietary approaches, the Diet could not contain any foods that James had already been exposed to. Leslie's concerns about the adverse effects of the oils resulted in their removal from the diet; new oils were gradually added in one at a time.

B. Controlling the nursing mom's diet: Two year-old James had not yet been weaned when he began the Instant intervention program of Applicant program. For this reason, his mom Leslie had to restrict her food intake to only those foods specified by her diet plan. By five months, however, James was weaned and showed remarkable improvement.

2. Environmental Consideration

A. Chemical sensitivities, particularly formaldehyde residues (plastics, foam, and fumes from gas heat): Once the diet was restricted to non-harmful foods, the environmental sensitivities were revealed. Heated by gas and full of plastic and foam materials, James's polluted home proved to be the largest cause of his eczema breakouts. With these plastic items removed and less irritating air and water systems installed, James showed great improvement. Furthermore, with each incidental re-exposure, James's symptoms worsened. This only reinforced the impact of these chemical irritants.

B. Other environmental sensitivities: James displayed intolerance to pollen and mold. Although The research investigator and counselor recommended some protective measures, completely guarding young James against these ubiquitous particles, this proved to be a nearly impossible task. However, with James's symptom level so close to zero, the present goal is to maintain limited exposure while expanding James's diet beyond the unusual foods.

Example Case Study VI. Severely Underweight, Food Sensitivities, Anxiety

Figure 8:
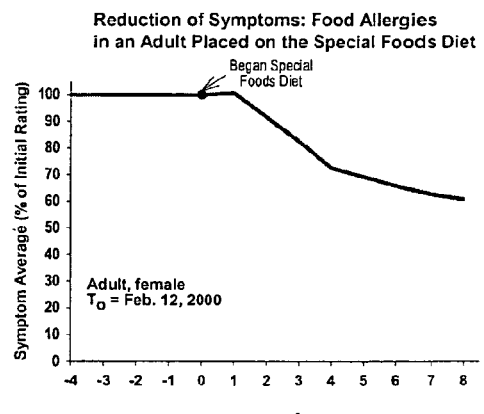
FIG. 8 is a graph showing reduction of particular symptoms in an adult placed on the special foods diet.

Case Summary: FIG. 8 shows the improvements in symptom averages for an adult experiencing symptoms from food allergies. When Sherrie first called the instant intervention program of Applicant to talk about beginning a new diet she was anxious to begin but worried about the results. Previous diets for her allergies and illnesses had left her severely underweight—a meager 95 pounds to her 5'-8" frame—and caused her sensitivities to proliferate and increase greatly in severity. She described frequent choking sensations in her neck and throat among many other symptoms. Her difficulty in concentrating and comprehending was obvious. She expressed great fear, and reported crying most days because she was so hungry, frustrated and frightened. Sherrie was sure that she was going to starve to death. Her food history was so difficult that she was extremely nervous about eating anything at all.

She decided that she had to try the Instant intervention program of Applicant, but she was convinced that she would react to at least half of the foods on the diet. She had spent so long combating her food allergies she was very hesitant to turn control of her diet over to someone else. Through a series of phone conversations and many questions, a diet was tailored for her, which she scrutinized in minute detail. She had to have continual reassurance that the staff had done diets before, for people equally as sick, and been successful. Sherrie was also excited about the increased variety of foods and the ability to eat as much as she wanted.

Initially Sherrie made daily phone calls with questions and concerns; these quickly focused on oils. Sherrie had experienced problems with many oils previously. In the early weeks of the diet she experienced daily choking sensations in her neck and throat and became very worried about the recommended oils. On her own she eliminated them all, and did see improvement. In preparation of the diet, because of her concerns about oils, we purposely included bear, a high fat meat, in her diet. At this point we were able show her that she still had fat in her diet with no effects, thus providing strong evidence that her body possessed the capability to handle oils. She was gently reminded that the symptoms were likely expressions of her fear and that she had already been consuming oils in her meat with no trouble at all.

This was an amazing turning point for Sherrie. She was able to add other higher fat meats to her diet without effects. Over several weeks Sherrie slowly worked the oils back in to her diet. Initially she reacted to oils only when she knew they were present (in cookies, for example). We recommended that for the next week Sherrie stir her oils into instants, creamed cereals and so forth, so that they would not be obviously present in the food. This helped Sherrie to realize that the symptoms she had generalized to large categories of foods were only specific to her old foods. The next step was eating the oils in obvious ways, e.g., spread on toast. When the imitation nut butters were finally introduced, Sherrie ate them and talked only of how much she enjoyed them.

By week four of the diet, the overall benefits of the diet were already manifesting themselves. She was beginning to look healthier. In fact, people were commenting on how well she looked. She was experiencing more energy and beginning to think more clearly. She gained five pounds and was looking forward to gaining more.

She was still experiencing minor choking sensations, but now was able to discern a pattern: On days when she was hungry and had plenty to eat she would generally feel fine. On days when she had to stretch her foods because she was afraid of running out, she would have an acid build up and the choking sensation and tightening in her chest would occur. The anxieties over food were creating reactions that had little physical basis. She was now able to evaluate her situation realistically, and recognize the basis for some symptoms. At present all of Sherrie's choking sensations have proven to be anxiety related.

During week 5 on the diet, it was learned that Sherrie had been boiling and then drinking city tap water instead of the recommended bottled water. Bottled water in plastic had previously caused severe chest tightness and pain.

She had been unable to locate distilled water in glass bottles so it was recommended that she buy the water in the plastic bottles and run it through a Brita Filter into a glass jar, and then boil the water vigorously. The purpose of the Brita filter was to remove the phthalate esters and unreacted monomers leaching from the plastic container the purpose of the boiling water was two fold: 1) to denature any mold filaments in the water, and 2) keep a procedure that Sherrie was comfortable with. Sherrie was able to use this water without effects.

Overlying fear symptoms, once eliminated, as described above, now made it possible for Sherrie to more correctly interpret her remaining symptoms. During week 5, Sherrie realized was experiencing diarrhea on Mondays and Tuesdays, and she was not feeling well after eating okra. Once okra was removed during the sixth week, the diarrhea was eliminated. After six weeks the diet seemed to be working well. Sherrie's doctor recommended that she hold this diet constant and spend the next two months just resting. With her diminished weight, and overall poor health, the doctor felt like this time would allow her body the recovery it needed for her to be able to re-establish her health.

Approach: The Instant intervention program of Applicant was important for Sherrie in two ways. First, it solved the food allergy problems that had been plaguing her for the past several years. Second, the solid information gained while on the diet, allowed her erroneous conclusions, which caused her to be unnecessarily fearful, to be replaced by correct ones. In the absence of this anxiety and fear, she began to make new cause and effect associations that were consistent with her body. These provided still further reductions of fear and anxiety.

1. Dietary Consideration

A. Accidental Starvation: When Sherrie started working with The instant intervention program of Applicant her limited diet and illnesses had brought her to a dangerously low weight. She had not found any foods that were well tolerated by her body. It was important to be able to offer her alternative foods that her body could tolerate. Much of the work with her revolved around ensuring she consume enough calories. She was initially hesitant to use the oils that were high calorie, so she needed to be diligent about eating large servings of carbohydrates.

B. Dietary Balance: Prior to beginning the Instant intervention program of Applicant, the only foods Sherrie was able to eat were vegetables. She would eat massive quantities of vegetables, however, because vegetable are so low in calories she was not able to maintain her weight. As she began the diet Sherrie wanted to do what was comfortable for her and eat mostly vegetables. It took many conversations before she was able to comprehend the need for her to focus her energy on eating carbohydrates, fats, and proteins.

2. Emotional Considerations

A. General Food Fears: Food sensitivities had made Sherrie unable to confidently eat anything. Her pattern of developing sensitivities had made her fearful of trying any foods. When she was introduced to foods that she knew nothing about, the fears were less strong.

B. Specific Food Fears: Sherrie had been sick for so long that the thought of becoming sick again was a paralyzing fear. Many of the reactions she reported on the diet were linked to specific food fears. For instance, she believed that all oils would cause her reactions. However, they only gave her reactions when she knew they were present in the foods. The simplicity of the Instant approach made it possible to construct a scenario that would honestly answer the question for sure—"Do I have problems with all oils or not?"

Figure 9:
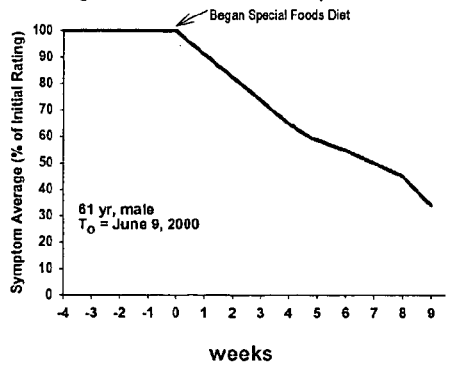
FIG. 9 is a graph showing reduction of particular symptoms in an adult placed on the special foods diet.

Example Case Study VII. Alzheimer's Disease, OCD, Noise Sensitivity, Violent Jerking Case Summary: FIG. 9 shows the improvements in symptom averages for an adult experiencing symptoms from Alzheimer's disease, and experiencing violent jerking symptoms. Seven years ago, Charles was a district manager for one of the largest insurance companies in the country. With over thirty years of experience, he had spent the past fifteen overseeing five separate claims offices in the region. In short, his professional responsibilities were substantial. However, his ability to concentrate on a specific task or to follow the contents of a conversation was slowly decreasing. His wife, Alice, noticed the change first and forced him to see a doctor. Finding the position as district supervisor too much to handle, he decreased his charge to just one office. Two years later, Charles left work completely, resigning due to apparent disability. Soon thereafter, the 55 year-old was diagnosed with Alzheimer's disease—seven physicians supported the initial diagnosis.

Five years later, Charles's condition had deteriorated rapidly. Several times a day, Charles's body would erupt into violent jerking and shaking. Not under his control, these fits would hit suddenly and cause him to fall down. Over the past few years, he had become very sensitive to noise and would complain loudly about nearby construction. He had also developed obsessive-compulsive tendencies. For example, he would keep putting on layer after layer of clothing and would refuse to undress before going to bed. His enormous frustration in not being able to perform simple tasks, such as shaving or raking, resulted in violent outbursts of rage. In addition, Charles was now almost completely non-communicative and rarely made eye contact. Alice also reported that Charles had become indifferent to his friends and family-members, herself included. Nobody was treated with particular attention or affection.

Alice tried to place Charles on a gluten-free, casein-free diet two years ago. While there had been no evidence that a change in diet could influence the Alzheimer's disease, Alice was concerned that many of his symptoms were precipitated by food allergies. Indeed, Charles had been having ribbon stools for the past 3 years and had recently been diagnosed with Leaky Gut Syndrome, a known consequence of food allergies. Also, the back of one of his hands was completely covered with eczema. At the very least, she hoped that a change in diet would ease this discomfort.

Although Charles's behavior did improve at first, after a few months of eating rice-products everyday, he was soon worse than he'd ever been before. Realizing the need for a rotation diet of unusual foods, Alice contacted the instant intervention program of Applicant to eliminate his food allergies. She also replaced his citrate form of calcium supplements with calcium dolomite.

After four weeks, Charles's symptoms were below 65 percent of his original condition. He no longer suffered from diarrhea and the severity and frequency of the involuntary jerking had disappeared. He also seemed much less sensitive to noise, more affectionate toward his family, and more able to engage in conversation. His obsessive-compulsive behavior had also dropped by over 37 percent. Best of all, his previous intense frustration at not being able to perform simple tasks had been cut in half!

For this Alzheimer's sufferer the Instant intervention program of Applicant was able to eliminate all of his symptoms caused by food allergies, and the methodology of the Comprehensive Intervention Program provided a framework for identifying and eliminating chemical sensitivities. At six weeks and 55 percent of his original condition, Charles was really starting to show some signs of his old self. For the first time in over six months, Charles answered a question with a complete sentence. He even tried to tell her something about a man: this was his first attempt to initiate communication in over a year. On his own, Charles went next-door to play basketball: he shot hoops and bounced and retrieved the ball all by himself.

After 2 months on the diet, Charles has shown impressive improvement: he's now at 34 percent of his original condition. With daily doses of calcium dolomite, the occurrence of violent jerking has been eliminated. He also initiates affectionate exchanges, giving hugs and "love pats," and seems to enjoy spending time with his family. His obsessive-compulsive behavior has also subsided and his rages of frustration are noticeably less severe.

Approach: Sixty-one year-old Charles was diagnosed with Alzheimer's disease five years ago. Hoping to eliminate those symptoms caused by food allergies, his wife contacted the instant intervention program of Applicant to set up a rotation diet of unusual foods. Charles's symptoms have shown steady improvement and his environment is being monitored for possible chemical sensitivities. We expect continued improvement as the symptoms are reduced even further.

1. Dietary Considerations, Calcium Supplements: Alice noticed that his violent jerking subsided when she gave him calcium supplements. Charles had been taking a citrate form of calcium supplement before starting the diet. Once he started the diet, the calcium supplements were switched to calcium dolomite and the violent jerking stopped.

2. Environmental Considerations, Gas heat: Charles's heat and hot water were controlled by a gas system. With food sensitivities, Charles was also probably affected by possible chemical sensitivities. The research investigator and counselors suggested that the system be switched to electric.

Figure 10:
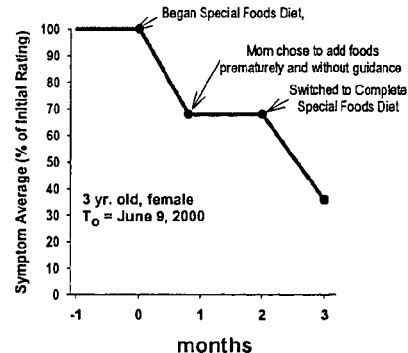
FIG. 10 is a graph showing reduction of particular symptoms in a child placed on the special foods diet.

Example Case Study VIII. Constipation, Gas, Congestion, Delayed Motor and Social Skills Case Summary: FIG. 10 shows the improvements in symptom averages for a child experiencing severe constipation, gas, congestion, and delayed motor and social skills. Two year-old Emma was born with the genetic malformation, Robinow syndrome, or "Fetal-face" syndrome. Characteristic of the condition, Emma's body had distinctive skeletal abnormalities; these were not the focus of our work with Emma. In addition to her condition, Emma was beyond miserable. Her problems with constipation and gas were severe, rating a 10 on a scale of 0-10. Night after night, day after day she screamed and writhed in pain. Her congestion was constant. Emma was so consumed by her constant pain that she was simply uninterested in social activities. Although she had a nice disposition she was far too uncomfortable to socialize normally, and was also behind in talking. She was able to say one word, 'ma' occasionally. Because of low muscle tone, she was unable to walk, although she was able to crawl.

Emma's mom began the Instant intervention program of Applicant, and there were many questions and issues. Early on there was concern that the additional fiber and associated bulk might be difficult for Emma to handle due to her low muscle tone. Her constipation was so severe that a longer period of time was required for her system to rid itself of the old foods. Emma's mom was advised to administer enemas as needed. To avoid adding additional exposures, Emma's mom was advised to use the distilled water Emma used for drinking, warmed to body temperature. The severe, painful gas became essentially imperceptible within about 3 weeks, but there was relatively little change in constipation.

Emma's mother believed that because of the low muscle tone, the constipation would always be a problem, and she did not expect much improvement in congestion or socialization. Feeling that further appointments were not going to be helpful, Emma's mom took matters into her own hands and began to add additional foods. She added a number of carbohydrates, of various seeds and grains, kept a few of the Instant carbohydrates, mixed in with a variety of common vegetables.

Two months after beginning the initial program, Emma's mother reentered her into the Instant Intervention Program. During the period that Emma's mom worked alone, Emma showed no progress. There was no change in the constipation, no further improvement in congestion, motor skills or socialization. Emma was still miserable.

Emma's research investigator and counselor carefully listened to Emma's mom, and determined that the initial discouragement was probably due to problems with foods on two days on Emma's original diet. A new, modified 5-day diet was developed for Emma. This time progress was made in all areas.

After one month on the new diet, contrary to Emma's mother's beliefs, the problems with constipation and gas completely disappeared. Emma's stools were well formed but soft, were passed easily, the gas was gone and the congestion greatly improved. Her muscle tone also improved 40%.

Now that Emma is completely pain-free, we will be watching for major improvements in socialization skills in the coming months. With the improvements in muscle tone already evident, Emma is expected to begin walking soon.

Approach: Emma suffered with severe constipation and gas, and less severe congestion, low muscle tone. These problems contributed the delayed social skills and delayed abilities to speak and walk.

1. Dietary Consideration: Mom was too easily discouraged and misinterpreted early results. One of the most difficult tasks was establishing a productive relationship with Emma's mom and helping her overcome her deeply held conviction that no help was available for her child's severe constipation and low muscle tone. These beliefs caused Emma's mom to misinterpret problems on two days in the diet, and become discouraged early. This caused a six-week delay for Emma.

2. Environmental Consideration: Pollen sensitivities. As digestive problems were eliminated, there was a simultaneous improvement in congestion; however this improvement was variable, sometimes improving, sometimes becoming worse. Because the fluctuations do not follow the patterns of a rotation diet, and because the variation was noticed during ragweed season, pollen prevention procedures were recommended. These are expected to eliminate the congestion problems.

Example Case Study IX. Hyperactivity, Acid Reflux, Irritability, Congestion

Figure 11:
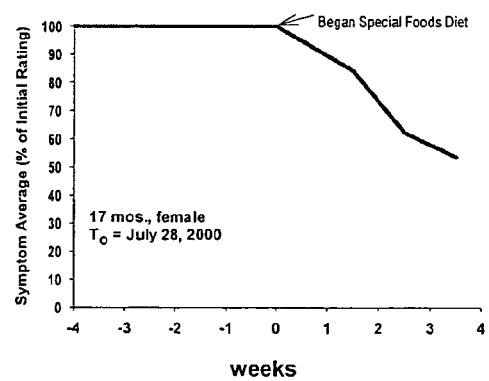
FIG. 11 is a graph showing reduction of particular symptoms in a child placed on the special foods diet.

Case Summary: FIG. 11 shows the improvements in symptom averages for a child experiencing hyperactivity, drooling and acid imbalance. To Barbara, contacting the instant intervention program of Applicant was a last resort. Her seventeen month-old adopted daughter, Amy, had a very severe fatty-acid imbalance, which interfered with every aspect of her life. Amy had been taking a number of various herbal supplements but achieved no relief. Her severe acid reflux caused her to spit up after every meal. She also drooled constantly and had hiccups at least three times a day. Her bowel movements were highly variable, ranging from severe diarrhea to normal stools, and were especially painful, due to the ring of raw red skin around her anal opening.

She also had tremendous difficulty breathing as her system was constantly congested. Her circulatory system seemed significantly inefficient: her body temperature was always below normal and her blood vessels never dilated in response to heat. Barbara reported that Amy had never broken out into a sweat and, despite frequent sickness, she had never run a fever.

In addition, Amy was extremely hyperactive. When awake, she was extraordinarily restless and seemed unable to sit still. She invariably woke up screaming in the middle of a nap. She was generally irritable and often threw tremendous temper tantrums. She also seemed very sensitive to touch. Although she craved the closeness and comfort of being held, any light brushing touch was immediately met with a loud scream. Also, she was extremely intolerant of any loud noises or commotion around her and hated to be moved around in a swing or stroller.

Amy had been eating baby formula and some solid meals. Before starting the Diet, Barbara stopped giving Amy the herbal supplements. Naturally, the withdrawal period was full of uncomfortable adjustments. She rejected most of the foods for the first few days and Barbara reported that young Amy would scream whenever she was left unattended, even if just for a second.

On the other hand, her previously severe diarrhea had disappeared and her severe acid reflux was waning. Also, the area around her anal opening was less red. Now her hiccup spells occurred only once every 2 days instead of three times a day. Even the volume of her constant drooling was going down. By the second week, Amy was having six well-formed normal stools a day; a good sign that her body was adjusting properly to the new foods.

Now into the third week on the instant intervention program of Applicant program, Amy's diet is still being finalized. Her previously severe gas is now completely gone, as is her diarrhea and acid reflux. The irritation around her anal opening has also disappeared. Without the irritation of her digestive system, her body should be better able to adjust to the new diet. Once her body is comfortable, it is expected that the restlessness and hyperactivity will also diminish.

Approach: Amy's intense hyperactivity and restlessness seemed to be a behavioral manifestation of her physical discomfort. The seventeen month-old had been diagnosed as having a severe fatty acid imbalance, which caused painful irritation of her digestive system. Among her most severe symptoms were severe acid reflux, variable stools, constant drooling, and irritation around the anal opening. Within one week, these symptoms had shown improvement. By the second week, nearly all of the digestion-related were substantially decreased. Dietary changes are still being made, as necessary. Once the physical symptoms reach a stable zero level, the behavioral problems should also decrease.

1. Dietary Consideration

A. Dietary Supplements: Amy had been taking a large number of herbal supplements in an attempt to combat her severe fatty acid imbalance and elevated yeast problems. Before starting the Instant intervention program of Applicant, all herbal supplements were discontinued.

B. Baby Formula Diet: Until starting the Instant intervention program of Applicant, Amy had been eating a couple bottles of formula today and a few solid-food meals. She was not used to eating all solid foods and longed for her bottle. The research investigator and counselor recommended that the new foods be pureed, diluted and given in a bottle.

Figure 12:
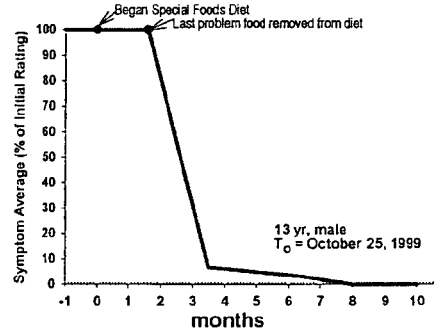
FIG. 12 is a graph showing reduction of particular symptoms in a patient placed on the special foods diet.

Example Case Study X. Autistic 12-Year Old Recovers Through the Instant Intervention Program Case Summary: FIG. 12 shows the improvements in symptom averages for a child suffering from autism and OCD, and exhibiting violent outbursts. On the inside Ben was tormented with severe OCD and autistic behaviors. He suffered from hypersensitivities to noise and motion, was unable to tolerate any mistakes in himself or others, he adhered to compulsive schedules and demanded the same from others. Ben spent as much time as he could in his preferred place, a dark, quiet corner of the basement away from everyone, including his family. He struggled with barely controlled feelings of frustration and rage that erupted into frightening violence when overwhelmed by noise, mistakes and other things, or when his schedules were disrupted slightly. Although Ben was able to do his schoolwork and he could be loving and affectionate with his family, this was not enough to counter his compulsive rituals and overwhelming rages.

Ben displayed uncontrollable anger, sometimes rational and sometimes irrational, for when overwhelmed or provoked he would attack the nearest person or item. His anger would flare up abruptly in public. He was home-schooled because he would become so upset by other children's mistakes that Ben would attack them, punching and kicking. Ben's doctors prescribed Bu-Spar, to help control his anger. The drug was merely the difference between somewhat contained rage and constant violent eruptions.

Ben's hypersensitivity to noise and motion, and his inflexibility in changing environments made it virtually impossible to go out in public. The only place Ben could tolerate was a Saturday church service, because it was quiet and there were no children. After church, however, the family would have to return home immediately. If there were any side trips or stops, Ben would explode. Once they got home Ben would immediately run down to the basement, and would not emerge for the rest of the day. If his mother took Ben on short trips and errands he could not deal with the sounds of the local shopping malls and stores. He would often erupt into a violent rage, punching and yelling, directed at whoever was within arm's reach, even strangers. These fits were usually accompanied by insults and murderous threats, and would last until someone would restrain him. Nothing but time seemed to calm him down.

His parents eventually stopped trying to control him, in an effort to avoid any possible outbreaks of rage. The family arranged their lives around his, constantly walking on eggshells. So chainsaws, drills and vacuum cleaners were not part of their lives. The family lived in a bizarre pattern of schedules and rituals wrapped around Ben's needs. He disliked any situation that called for a change in plans. There was a specific time for everything he did, from eating dinner to going to bed. If these patterns were shifted Ben's rage was overwhelming. Still Ben was overwhelmed by the world around him, and he spent most of his time in the quiet comfort of a corner in the basement. The basement was dark with no human interaction. Ben's mother was at an impasse. In many ways her son had come far. Gluten-free and casein-free diets and other strategies had helped. Ben felt an array of emotions, could be loving, was able to learn easily, and possessed an awareness and presence in his world, but these strategies had not been able to help Ben break through the violent rages, obsessive/compulsive rituals, and sensory sensitivities. Because of his insistence on food rituals, including eating only muffins, she reasoned that there must be more to achieve with dietary intervention.

In October 1999, Ben's mom enrolled Ben in the instant intervention program of Applicant. 'Ben has come so far, but something is still holding him back. I think gluten-free, casein-free is not enough.' Pamela left the conference with an individually tailored diet that was the diet Ben needed and with a method to make sure not one single problem food remained in his diet. Ben still needed to begin with food choices that were appropriate for the rituals he surrounded himself with. So Pam's initial 5-week food choices were a first for the instant intervention program of Applicant, an all muffin version of the Instant dietary intervention program of Applicant.

Pamela reported that Ben's diet worked fairly well from the beginning. There were, however, patterns that she began to notice almost immediately. She noticed that on certain days, Ben would wet the bed heavily, and on arising would seem to be in a daze and glassy eyed. One by one Ben's mom tested each food. Since the reactions were delayed, spacing foods apart on the same day would not be helpful, so she selected foods most likely and switched days. She reasoned that if the reaction pattern followed the foods from day to day, then those foods were the problems, and she adjusted the diet.

Dietary adjustments took about two months, and it was then that the truly dramatic changes began. She noticed that Ben stopped waking up with glassy eyes and bed-wetting was a thing of the past. The sense of calm and peace was beautiful to watch and to experience. Pam gradually eliminated the medications that had futilely attempted to diminish his rages; he simply did not need them anymore.

By the time Ben had been on his diet for five months he was still improving every day. Ben was able to tolerate change. He could go with the flow and he was beginning to show flexibility. His sensitivities to noise had decreased and he was now not bothered by the vacuum or drills. He could go out in public with moderate to zero symptoms. He had been able to go shopping with his family, and actually enjoyed (!) the camaraderie. He fully participated in a shopping trip, including looking for new things when a first choice was not found. He had just become an Acolyte at his local church. He walked down the aisle in front of the congregation and lit the candles by himself. On his first Sunday the other acolyte lit the candles in the wrong order. His mother held her breath. Before starting the Instant intervention program of Applicant, this would have been a sheer nightmare. An intensely enraged Ben would have attacked and punched the other boy's lights out in front of the whole church. Luckily that wasn't the case. In fact Ben didn't seem to mind the mistake. The rages were simply gone.

At home Ben no longer sought the quiet sanctuary of the darkened basement, but became a member of the family in a new way. His obsessive/compulsive rituals had disappeared. Finally the parents are able to be parents, providing the loving guidance and discipline that has never been possible before. In just five short months, Ben had almost fully recovered from his autism.

His mom continues to monitor his food carefully to ensure that Ben's reactions remain under control. He has gained about 15 pounds and grown about an inch.

Just two weeks ago, Ben went back to school—really back to school. Not to the quiet sanctuary of the home school he had been forced to attend for two years, but to a large, noisy, bustling junior high school he has never attended before. Ben is a happy, thrilled 7th grader who is enjoying everything—the bus rides to school, the noisy hallways, the large assemblies, the hustle and bustle of his mainstream classroom. He particularly enjoys the freedom of attending school without an aide. BEN IS BACK!!!

Ben's Dad is amazed at the wonderful changes. It was the diet that made the difference.—'I can hardly believe the answer is so simple! Just foods!"

After about two months on his diet, when the dramatic changes really began, Ben sat one day talking to his aunt—"You know, I'm almost over this autism. It won't be long and it'll be gone." He was right.

Approach: Ben's condition was debilitating. Although he was fairly healthy and energetic, the emotional problems caused by his food allergies prevented him from behaving and interacting appropriately. Unless these issues were resolved Ben would be dependent of his parents for the rest of his life. After being helped to put together the initial diet, Ben's mom was able to update it as she saw the need. Although Ben's diet is still not very large, everything on the diet works very well for him.

Dietary Consideration

A. Proliferation of Sensitivities: The previous severe limits on Ben's diet had caused many of his proliferating sensitivities. Before starting the diet Ben ate very few different foods. His immune system was still having unhealthy reactions to foods and this causes sensitivities to develop towards other foods. Along with this, his lack of calories led to the proliferation of sensitivities. It was very important for Ben to be able to eliminate all foods, have a rotation diet of new foods, and eat the right amounts of calories to keep the proliferation from spreading further.

B. Accidental Starvation: Ben will never be a heavy person. However, when he started the Instant intervention program of Applicant he was very underweight. His diet did not contain enough calories to keep his weight constant as his body grew. The Instant intervention program of Applicant provided a high calorie, well tolerated solution that allowed Ben to eat enough to maintain his weight, in fact he has already gained weight.

C. Specific Intolerances: It took several months for Ben's mom to make final important adjustments to Ben's diet. His sensitivities did not show themselves with rashes or digestive problems. When Ben was sensitive to a food the delayed symptom of bed-wetting was the best predictor. By testing his foods in a variety of orders his mother was able to determine which days were causing the problems. When these foods were eliminated Ben's bed wetting stopped. After the bed-wetting stopped, the autistic behaviors rapidly disappeared.

Behavioral Considerations

A. The benefit of the Instant intervention program of Applicant is to eliminate the direct effects and direct symptoms that have been preventing normal interaction and development. In Ben's case the direct effects were: rage, frustration, OCD, deep stuporous sleep, bed wetting, hypersensitivity to noise, hypersensitivity to motion and commotion. These abruptly were eliminated at about 2 months on the diet, when the last problem food was removed. The last three months have been times of adjusting to the tremendous change in sensation and brain function associated with the elimination of pain and other physical symptoms, and learning what normal function feels and acts like. We have observed that this time period lasts about 4-7 months in individuals Ben's age; after that time Ben was ready to complete his integration into normal living.

B. Discipline: Ben's rages had been so severe that his parents stopped attempting to give him direction or discipline him in any way. Now that Ben's rages have been eliminated, discipline and parental control and guidance were reintroduced.

Example Case Study: XI. Autism, Eczema and Hyperactivity

Figure 13:
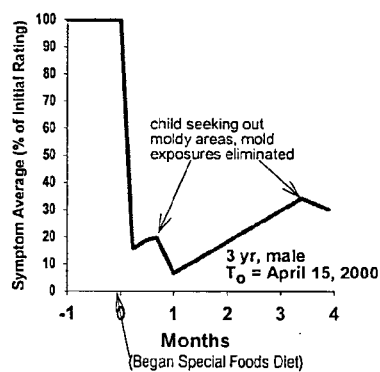
FIG. 13 is a graph showing reduction of particular symptoms in a child placed on the special foods diet.

Case Summary: FIG. 13 shows the improvements in symptom averages for a child suffering from autism, eczema and hyperactivity. Tony's behavior was so out of control it was barely tolerable by his family. He had temper tantrums that involved fierce hitting and biting. The tantrums were set off by nearly everything including sudden noise, removal of his toys and attempts to quiet him. His hyperactivity was constant; he ran back and forth, waving his hands and engaged in visual self stimulation in the form of rolling his eyes back and forth, turning his eyes sideways and looking at things very closely.

In conjunction with the aforementioned behavioral problems, Tony seemed to have trouble registering sensations. Therefore, he was attracted to anything that elicited a physical response. This attraction resulted in Tony wanting to taste everything, from sucking on the carpet to licking windowpanes. He often pressed on his eyes very hard and gagged himself with his fingers and xylophone sticks. Tony only responded emotionally to his mother and very little to his father. He was isolated socially, often unresponsive when called, and only engaged in brief eye contact.

In addition to his behavioral and emotional problems, Tony lived with a variety of physical ailments. His skin was constantly dry and rough with patches of eczema, and he had red ears and cheeks. He had constant diarrhea and congestion resulting in multiple ear infections.

Tony's parents contacted The instant intervention program of Applicant hoping to improve Tony's behavior and physical health. Setting up a diet for Tony was tricky since he would only eat crunchy and crisp foods that his mother had fried. These limitations were taken into consideration and Tony began the Instant Autism Intervention Program in April of 2000.

At first it was difficult for Tony to become adjusted to his sudden change in diet. He went through an intense withdrawal period as his old foods were eliminated. He became lethargic and sleepy, looked pale and developed dark circles under his eyes. He wailed loudly and went on a hunger strike for three days. His mother had to physically hold Tony's mouth closed for him to begin tasting the new foods. However, once he began tasting the foods, he slowly ate more and more. Tony's mother, Terry, noticed a remarkable reduction in many of Tony's most severe symptoms after just one week on the Instant intervention program of Applicant.

After two weeks, the strict diet exposed other problems such as environmental sensitivities that had been affecting Tony's behavior. Terry discovered that Tony was highly sensitive to mold and reacted to cleansing products like toothpaste and soaps. Tony would actively seek out moldy spots in his home. After contact with these spots his autistic symptoms returned. It was recommended to Terry that she thoroughly clean these areas with hypoallergenic soaps and cover them in aluminum foil. These environmental allergens were eliminated and Tony continued to improve.

At Tony's four-week check up his dry skin and eczema were no longer present. The redness in his cheeks and ears had also subsided. In addition, he no longer had diarrhea or excessive congestion. Although these physical improvements are certainly wonderful, perhaps the most dramatic changes could be observed in Tony's behavior. His episodes of hyperactivity disappeared, as did his tantrums and violent episodes. He no longer pressed on his eyes, gagged himself, sucked on the carpet or licked the windowpanes. He now responds when called and often uses appropriate verbal phrases to express himself, playfully interacting with those he feels comfortable with. He has begun to initiate and maintain eye contact. Perhaps most importantly, Tony has been able to attend preschool and function normally around his classmates. Before beginning the Instant intervention program of Applicant, Tony did not seem to notice other children. Now, he is expressing emotions such as joy, fear, and affection. He enjoys being hugged by his siblings and is playing normally with his toys.

Tony used to have trouble sleeping and would wake up screaming and crying several times throughout the night. After being placed on the Instant intervention program of Applicant, Tony has been sleeping 10-11 hours a night and his mother is able to establish a daily routine instead of being governed by Tony's tantrums and crying episodes. Tony's environmental sensitivities remain a challenge and Terry has to work very hard to eliminate all moldy areas or keep them out of Tony's reach. However, Tony's individually tailored diet has allowed Terry to discover these sensitivities as his food reactions were eliminated.

It has taken the accurate descriptions of the parents, and the expert assessments of the research investigator and counselor to find Tony's re-exposure strategies hidden within his familiar self stimulating patterns. For example, Tony likes 'lining', looking and walking along any line-type edge. Based on the careful assessment of the parent's descriptions, the research investigator and counselor found that Tony was only 'lining' hedges, fence rows, and other more damp and mold-prone areas. Switching him to 'lining' in non-moldy places such as sun drenched steps resulted in an abrupt stop of the behavior and a dramatic improvement in his overall symptoms.

The entire family has noticed Tony's improvements. In fact, Tony's five year-old sister recently said to Terry, "Mom, I gave Tony a hug and he didn't hit me and he didn't scream!" His physical problems have completely disappeared and his behavioral problems have significantly improved.

The task now is keeping Tony out of reach of potentially harmful areas. As he improves, he also develops new subtle ways to re-expose himself, to molds especially. There is now a concentrated effort to seek out and eliminate exposure to the moldy areas he has been getting into. This battle has been somewhat challenging, with individual relapses occurring as each new exposure occurs. With continued monitoring and control of environmental allergens, Tony should continue to improve behaviorally and emotionally. Tony's father has definitely noticed the good the diet is doing, "The program is working." Pure and simple, it seems to be.

Approach:

Tony's condition was emotionally, physically, and socially debilitating. His behavior problems prevented him from having a balanced diet, sleeping through the night, forming relationships with other children, expressing his needs and showing affection to his family members. After putting Tony on the Instant intervention program of Applicant, with the guidance of The research investigator and counselors, his mother was able to identify and address previously unknown environmental sensitivities. Previously, he had been so controlled by environmental and food sensitivities that functioning normally had not been possible.

Dietary Consideration

A. Intense Withdrawal: Tony rejected his new diet at first and went through a strenuous adjustment period lasting approximately three days. Tony's withdrawal consisted of a hunger strike and irritability. Fortunately, Terry was not discouraged by this and Tony began eating normally after a few days.

B. Lack of Sensation: Tony's severe sensitivities had caused him to become incapable of being affected by his surroundings. This lack of sensation caused him to seek out any sort of object that would elicit a physical or emotional response. The result was constant sucking on the carpet, licking of windowpanes, actively searching for moldy areas, screaming, running in circles, and a tremendous amount of hyperactivity. This constant self-stimulation thoroughly exhausted his parents. The Instant intervention program of Applicant broke the barrier between Tony's numbness and his surroundings. He began to experience events normally and his behavior problems were dramatically reduced.

C. Physical Ailments: Tony's reactions were not limited to behavioral problems. He exhibited physical ailments as well. His diet was designed especially to eliminate his eczema, diarrhea, and congestion. After just one week on his diet, Tony exhibited no further ailments.

Behavioral Considerations

A. The benefit of the Instant intervention program of Applicant is that it allowed Tony to no longer need to engage in his hyperactivity and other irrational behaviors.

B. Tony has already shown a great deal of improvement in his social skills. He seems to be seeing other people for the first time in his life. Some of the new people Tony has become aware of initially frighten him. This fear was observed at a recent birthday party. However, the fact that Tony responds to others with emotion is a significant social victory for him and his parents because for the first time he has realized these others are present in his world. His frightened behavior was much like separation anxiety of 1 year olds. With help from his parents so Tony can avoid re-exposure to things he is sensitive to, Tony will now be able to progress socially following the normal pattern of social development and maturation.

Example Case Study: XII. Autistic, Hyperactive

Figure 14:
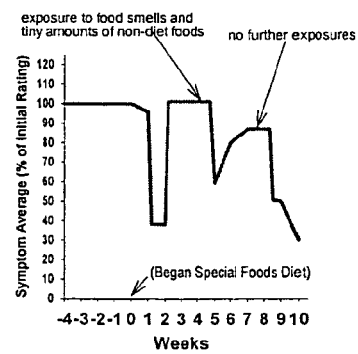
FIG. 14 is a graph showing reduction of particular symptoms in a child placed on the special foods diet.

Case Summary: FIG. 14 shows the improvements in symptom averages for a child suffering from autism, eczema and hyperactivity. Six-year-old Steven was exhibiting autistic behaviors and hyperactivity and suffering from eczema when he began the Instant intervention program of Applicant. Although Steven was able to swim, run, and jump on trampolines, and was affectionate toward his parents, he was hyperactive, slapped at objects that excited him, talked repetitive nonsense day and night, and was unresponsive to his parent's guidance in this area. Steven could not express his wants and needs to his parents. He had trouble sleeping through the night. He did not want to spend time with other children, preferring to play with his toys unconventionally and listen to his music books in isolation.

Perhaps the most persistent problem was Steven's compulsiveness with writing. He was constantly writing repetitive words and phrases, and also demanded that his parents write certain phrases for him, upon which he would examine their work and criticize any imperfections. If he was unsatisfied he went into tantrums and silly talked. This was frustrating for his parents, because they had worked diligently over the years to get Steven to speak well, and knew he was capable of doing so. Steven was also bothered by eczema spots found in several places.

At the end of Steven's first week on the Instant intervention program of Applicant, his symptoms and learned behaviors were essentially unchanged. Steven had no problem adjusting to the foods on the diet, exhibiting no withdrawal. He was used to restricted diets and old enough not to refuse something new. He did not show any reactions to the new foods. On about the eighth day Steven's symptom level abruptly dropped sixty percent. His hyperactivity had decreased, along with the accompanying hand slapping and silly talking. He complained more, therefore expressing his discomfort with certain situations, using longer sentences and pronouns. Steven's parents were very excited.

Unfortunately, just a few days later, his symptoms abruptly returned and quickly became worse than ever. At his one-month evaluation, it was clear that Steven's symptom trend had turned upside down! He was now running laps around tables, jumping on couches, and rolling the pencil he now carried with him at all times. He was running his words together, and screaming at all times of the day.

Steven's research investigator and counselor began a very careful evaluation of the events of the days just preceding the return of his symptoms, and found that two important events had occurred: 1) Steven had begun to take long, lingering inhalations of smells from the families' meals and desserts occasionally managing to eat traces of food, and 2) mom had baked large numbers of desserts over a two day period just prior to the return of symptoms, filling the house with wonderful aromas from baking. The food smelling had then become almost a ritual coinciding with continuation of high symptom levels for almost two weeks.

Since the cause/effect assessment indicated a strong possibility that Steven was highly sensitivity to odors from foods, the volatile components, it was highly likely that he would react similarly to volatile organic hydrocarbons in general. Also from the assessment of symptom fluctuations, it was found that Steven's exposure/symptom pattern was particularly complicated, he was a delayed reactor, requiring 1-2 days for symptoms to occur, and he generally required a full week, 7-8 days, for symptoms to disappear following an exposure.

The research investigator and counselor recommended a series of procedures for preventing Steven from eating even the smallest bit of food, completely preventing exposure to cooking fumes and mealtime odors from non-diet foods, and finally recommending ways to prevent exposure to volatile substances and synthetic materials in the home. In addition Steven was to spend the majority of his waking hours outdoors in the fresh air.

It was predicted that it would take at least a week for the symptoms to begin to drop, and then they would drop dramatically. This was precisely the case. Unfortunately about a week later, as soon as Steven's symptoms began to plummet, he managed to grab a bite of his brother's food, and his symptoms began to climb abruptly again.

This was the beginning of a most frustrating several week period of waiting for a week, and suffering a re-exposure at the end of the week and abrupt return of symptoms, making a change, waiting again, and in the process learning more about Steven's exquisite sensitivities. During this time, he proved to be particularly adept at finding and eating hidden food, apparently unerringly guided by the faintest of smells, and he was unintentionally exposed to a significant level of volatile substances, which caused a strong reaction.

With each new problem, the research investigator and counselors provided appropriate recommendations to prevent further exposures of that type, until finally all problem exposures were completely eliminated for good on week eight. At that time, after the requisite week, the symptom levels began dropping and continued to drop. This time they did not shoot back up.

To this day, the struggle is to keep Steven under supervision and out of the way of environmental substances that are harmful to him. Following the guidance of the research investigator and counselor Julie has diligently sought out and eliminated the hazards. Steven is doing much better overall and his symptoms continue to decrease. Because of Steven's age, the learned behaviors are expected to begin to show major improvement 2-4 months after Steven is able to achieve and maintain a consistent zero-symptom level.

Approach: By carefully evaluating the Steven's symptom pattern during the first two weeks on the Instant intervention program of Applicant, it was found that he experienced both delayed reactions and delayed recovery following exposure. This was very important in performing accurate cause and effect assessments of subsequent exposure patterns. It took longer to determine the nature and extent of Steven's sensitivities, and develop effective avoidance strategies, because of the delayed reactions and delayed recovery times and Steven's skill in getting into foods off the diet. Steven's problems were primarily caused by many food sensitivities, and exquisite sensitivities to food aromas and volatile chemical substances. The most difficult tasks involved effectively preventing this 'smell detective' from achieving repeated exposures.

1. Dietary Consideration

A. Keeping Away from Non-Diet Foods: Steven's desire for pies, pizza, and other regular foods did not stop until the 8th week of the Instant intervention program of Applicant when all food smells were effectively and consistently eliminated. Although not unique, his reactions to smells from off-diet foods occurred at very low levels. Sensitivities at very low levels made it necessary to eliminate not only foods (the Instant dietary intervention program of Applicant) but made it necessary to incorporate measures to eliminate exposure to food smells.

2. Environmental Considerations

A. Chemical sensitivities, particularly to volatile organic hydrocarbons: As Steven progressed in the Instant Assessment Program several environmental sensitivities were revealed (plastics, fumes from the computer, and chlorine and chlorinated hydrocarbons in bathwater). These caused a return of some of his previous symptoms; however, a newly paved driveway emitted fumes that caused a relapse, adding new symptoms as well (silly talk, sleeplessness). It was recommended that the family take a vacation to help reduce Steven's levels of chemical exposures.

B. Other sensitivities: Foods and sensitivities to volatile substances proved to be Steven's primary problems, sensitivities to mold, pollens and so forth proved to be relatively unimportant in comparison.

Example Case Study: XIII. PDD, Lack of Eye Contact

Figure 15:
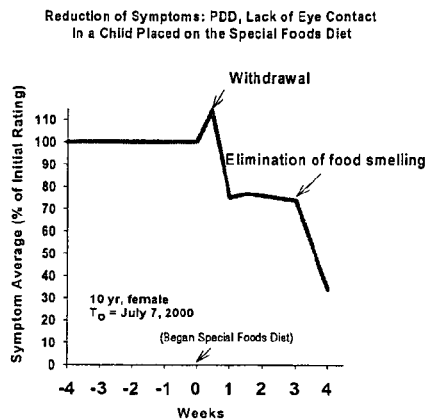
FIG. 15 is a graph showing reduction of particular symptoms in a child placed on the special foods diet.

Case Summary: FIG. 15 shows the improvements in symptom averages for a child suffering from PDD, and lack of eye contact. Ten year-old Maria displayed several symptoms of pervasive development disorder (PDD). Her social development seemed greatly underdeveloped. Although her relationship with her mother was comfortable and appropriate, interaction with others made her very tense, anxious and flustered. Her other family-members and strangers were held at a careful distance: she refused to make eye contact and her speech instantly became jumbled and agitated.

Whenever Maria got upset, she would clench her fists, turn bright red and make grunting sounds. She was extremely irritated by quarreling, crying or general commotion. She was also particularly distressed by others' singing. Although she enjoyed listening to the radio, if anyone hummed along, she would growl, become very rigid and clench her fists. The singing of the congregation at church was just unbearable for her; it pained her to the point of tears.

In addition, Maria's mother, Shannon, reported that her daughter's body temperature was slightly warmer than it should be. Maria had trouble falling asleep; she also tended to wake up several times during the night. Shannon also suspected that her daughter was sensitive to visual stimuli and had an acute sense of smell.

This kind of heightened sensory perception was consistent with the autism diagnosis. Furthermore, tests had shown that Maria's body was indeed producing the morphine-like chemicals of the "Opiate Effect" in response to gluten and casein. Although Maria had shown some gradual improvement after switching to a gluten-free and casein-free diet, Shannon hoped for more dramatic results with a complete dietary change. Maria had also been taking Prozac and melatonin; these medications were kept constant (in active ingredient form only) in an effort to isolate the effects of the dietary change.

Although Maria had shown minor withdrawal symptoms on the previous GFCF diet, she exhibited more intense withdrawal during the first week on the new diet. She refused to eat most of the new food, preferring to smell the foods being cooked for the rest of the family. While she seemed quiet and lethargic 90% of the time, she occasionally lashed out in a fierce rage. Although distressing for the family, this response followed the typical withdrawal pattern and was consistent with the initial predictions. The research investigator and counselor recommended that the food smelling be eliminated by running the exhaust fan, opening the windows, and by keeping Maria away from the kitchen during cooking. Should Maria refuse to eat completely, the research investigator and counselors recommended that a broth be made to squirt into the side of her mouth. This would prevent the irritating effects of stomach acid on an empty stomach.

By the middle of the next week, Maria was already showing significant improvement. Her appetite had picked up and she had regained her lively attitude. She also seemed to be less anxious in social situations. By the third week, she was noticeably happier, calmer and more content than she'd ever been before. Now she expressed a willingness to go the movies and create plaster sculptures. She even showed concern for her nanny, who was feeling ill. Shannon nearly fell over with delighted surprise at her daughter's new capacity for sympathy.

Her symptoms continued to decrease into the fourth week: social situations were less threatening and her sensory perception seemed to function at a more normal level. With the diet now completely under control, Shannon began noticing Maria's reactions to her environment. Suspecting a sensitivity to mold, Shannon moved Maria from her bedroom, where a leak in the ceiling had developed. She noticed an immediate difference in Maria's mood and behavior. The research investigator and counselor also recommended that the air ducts be covered to prevent the contaminated air from circulating throughout the house. Because Maria's symptoms seemed to worsen when in the car, the research investigator and counselors also suggested that she ride with the windows down, but to roll them up when around trucks, buses or road construction.

Now into the fifth week of the diet, Maria has really shown fantastic improvement. In fact, now that she's sleeping soundly and beaming a new happy attitude, her parents have decided to taper down her melatonin and Prozac medications. The family has also noticed that she is much more sociable and has been giving her mom huge warm hugs. She now seems to be actually reaching out to people for love and attention.

Approach: Diagnosed with PDD, Maria was a high functioning autistic ten year-old. Although her relationship with her mother was relatively warm and communicative, she became very tense and anxious when required to interact with others. She also demonstrated high sensitivity to aural, olfactory and visual stimulation. Previous tests had shown a neurological reaction to gluten and casein proteins; as expected, the withdrawal symptoms were fairly severe. Following the withdrawal period, Maria began a comfortable and appropriate decline. One of the most difficult tasks was to eliminate her exposure to food smells. By the fifth week, Maria's physical and behavioral symptoms have shown remarkable improvement. Continued progress is expected.

1. Dietary Consideration: Keeping Away from Non-diet Food Smells: Maria's acute sense of smell instantly recognized the aromas of non-diet foods. By the fourth week, smell avoidance strategies had been put into effect. Without the cravings induced by these smells, Maria has been able to adapt to her new diet without difficulty.

2. Environmental Considerations: Mold Sensitivities: The ceiling of Maria's bedroom had begun to leak and grow mold. Once she was removed from her bedroom environment, she showed immediate improvement. The air ducts were covered to prevent the mold particles from spreading throughout the house. Exposure to other moldy areas will continue to be eliminated.

Figure 16:
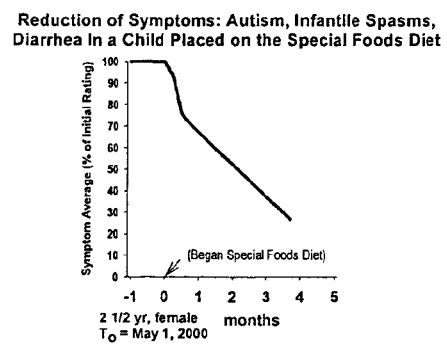
FIG. 16 is a graph showing reduction of particular symptoms in a child placed on the special foods diet.

Example Case Study: XIV. Hypotonic, Infantile Spasms, Diarrhea, Screaming, Autism Case Summary: FIG. 16 shows the improvements in symptom averages for an autistic child also suffering from infantile spasms and diarrhea. Born into a family with a discouraging medical history of multiple sclerosis, Heather came to the instant intervention program of Applicant with the odds stacked against her. Heather, a 27-month-old autistic child, is also affected with infantile spasms and seizures of the brain stem. Heather was also born colicky with a high sensitivity to light and sound. When Heather first came to the instant intervention program of Applicant in April 2000, her symptoms were severe and debilitating. She had 15-20 seizures per day and took several medications, including lamictal, topomax and B6, to keep the seizures from becoming even more frequent. Heather also had a severe diaper rash that created dry, bright red skin with bloody patches and raised areas. Furthermore, she had very painful bowel movements and diarrhea, which exacerbated the diaper rash irritation. She sometimes gagged resulting in the constant spitting up and vomiting, of foods. In addition, Heather's entire body was hypotonic, her head was sensitive to touch, and she had difficulty sleeping, vocalizing words and using her hands.

In addition to her physical ailments, Heather had many behavioral problems. She screamed constantly and engaged in self-stimulating behaviors, such as fast head shaking and grabbing at her face. She was also unable to show any emotion and hardly ever smiled thereby rendering personal relationships virtually impossible.

Because of her behavioral and dietary problems, Heather was unable to chew food. Her mother, Susan, had to puree the food, and give it in very soft forms or use a bottle. Her autistic behavior and seizures also did not allow her to communicate her dislike of the food before the diet. By the end of the second week on the Diet, however, Heather's symptoms began to lessen and she was more communicative about her food dislikes and likes. She began initiating eye contact and started crying to let her mother know when she was unhappy about a particular food. Her seizures were reduced to ten a day, and she was able to sleep easier at night.

Heather's case posed unique concerns because she was required to take medications for her seizures. Her mother was concerned that the impurities contained in the powerful medications were affecting the diet's success. It was recommended that her mother use the medications in pure form, powder or distilled water. Another suggestion was that her mother find a local compounding pharmacy to prepare the medication. B6 was removed from the medication cycle. To complicate matters, the new diet caused Heather to vomit more, preventing the digestion of her medication and causing her seizures to intensify. In an attempt to improve her daughter's digestion, The research investigator and counselor introduced exotic fruits to the diet and suggested that Heather be exercised by moving her legs and rolling her around.

Meanwhile, several of Heather's severe symptoms, including the diaper rash and painful bowel movements, were improving. She was beginning to show a more calm and quiet disposition was having less difficulty expressing her emotions. Even a pleasant smile started to appear on her little face!

After the third week Heather developed a rash under her chin and nose. Because the rash appeared just shortly after Susan had the carpeting professionally cleaned with a shampoo, it was concluded that the rash was a reaction to chemicals in the environment. As predicted, with the food allergies eliminated under Instant intervention program of Applicant, environmental sensitivities would be more easily observed.

By the end of the fourth month, Heather's symptoms have shown dramatic improvement. The screaming, spitting up, drooling have stopped. Her diaper rash, congestion and eczema have disappeared. Her eye contact is getting better every day, and Heather is engaging in more social interaction and is taking more interest in her toys. Her new happy smile and laugh show great hope for the future! She has steadily regained muscle tone, especially noticeable on her weak right side. She is able to push up with this hand, no longer loses foods when she eats due to inability to suck properly, and muscle tone in her legs is dramatically improved. She is no longer sensitive to light. At the end of 5 months of treatment through the instant invention program of Applicant, the child's seizures, having steadily and slowly declined, completely stopped and the child has been seizure-free for one month.

Approach: Debilitating infantile brain seizures that required large doses of medication to keep them under control compounded Heather's autism. She was also very sensitive to light, had severe diaper rash, lacked the ability to maintain eye contact, screamed constantly and showed an inability to form social relationships. While Heather's seizures are a persistent problem, her other symptoms have begun to disappear. She is now able to show some emotion and can interact more effectively with her family members.

1. Dietary Consideration: Seizure medication complications: Heather rejected the new diet at first. By throwing up the food, her medication was left undigested. To aid the digestion process, her mother attempted to exercise her and added some exotic fruits to her diet. She also diluted the food consistency to bring more water into Heather's system.

2. Environmental Considerations

A. Medication impurities: The necessity of the seizure medications meant that Heather's seizure medications had to be dealt with. A local compounding pharmacy was employed to provide the active ingredients only in distilled water. Her mother also excluded B6 from the medication cycle.

B. Rashes due to carpet chemicals: Environmental sensitivities were revealed when Heather developed a rash in reaction to the chemicals used in a professional carpet cleaning. Further environmental sensitivities will continue to be explored and eliminated.

Example Case Study: XV. Autism, Eczema, Hyperactivity

Figure 17:
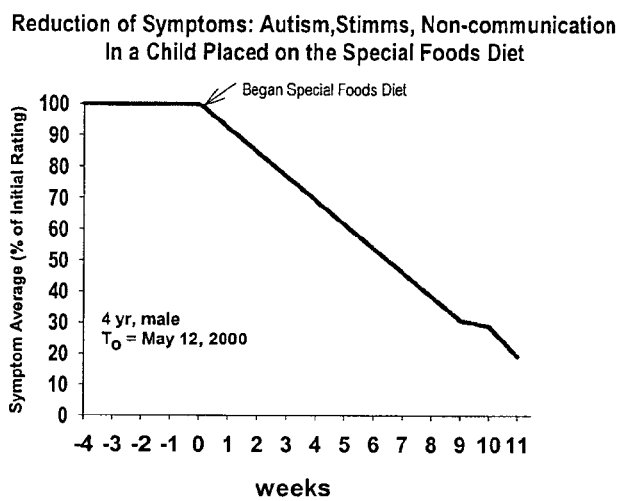
FIG. 17 is a graph showing reduction of particular symptoms in a child placed on the special foods diet.

Case Summary: FIG. 17 shows the improvements in symptom averages for an autistic child. At four years of age, Mark exhibited many classic symptoms of autism. Socially, Mark was extremely withdrawn. He ignored the activities of the rest of his family and never tried to communicate his wants or needs. Mark was also very hyperactive and was especially affected by visual stimulation. He would turn his head and move his body so as to look at one thing from various angles. He also loved to twirl sticks with his hands and insisted on lining up items in a row. Mark would throw a temper tantrum if this straight line would be even slightly disturbed. Mark's restless continued into the night: he had never gotten through a night without waking up, laughing hysterically.

Mark also suffered from several physical symptoms. Two to three times a day, Mark had very soft stools. Also, his legs were covered with eczema. Although always present, the dry red patches of skin were more apparent during periods of low humidity. Although his body seemed to be strong, his mother recognized that he wasn't eating enough food. Once he started a gluten-free, casein-free diet earlier this year, he immediately started to eat everything on his plate. His mother, Lisa, was excited about the improvement made during the first dietary change. However, she wished to completely eliminate all of his symptoms. She began using the instant products on her own, attempting to give him unusual foods in rotation.

After 8 weeks on Lisa's diet plan using the instant products, Mark had shown much improvement. His symptoms were down to 30.8 percent of his original condition. He tried to express his wants in one or two word commands: a very rare occurrence before the dietary change. He also played with the other children in the family: they chased each other around the house and splashed in the kiddy pool. Of all his symptoms, his sleeping had improved the most dramatically. Since eating the new foods, Mark had been sleeping for 9.5 hours every night with no interruptions. His eczema had also disappeared since using the instant products and his stools were now normal. Clearly, Mark had been tremendously affected by his food allergies.

After 9 weeks, Mark's diet was completely finalized: Lisa was following the research investigator and counselors' guidelines for a strict rotation diet of the foods. However, a few instances of food sneaking resulted in some setbacks. With The research investigator and counselor tracking Mark's progress, it was soon apparent that he had a delayed reaction pattern. He would react to foods within 4 to 24 hours after coming in contact with allergenic foods; recovery time took about 5-7 days. This delay of food reactions meant that it would be more difficult to assess diet-related issues.

Now at eleven weeks on the full Instant intervention program of Applicant program, Mark is now below 20 percent of his original condition. He sleeps like "a brick" through the entire night with no interruption. Aside from those few instances where exposure to non-diet foods occurred, Mark has been having regular, normal bowel movements. Most exciting for Lisa and the family is Mark's improved social interaction. He now tries to communicate his wants and needs with two or three words. He also engages in active play with his siblings. Although Lisa reports that he still needs help when imagination is involved, he is doing "a ton better than he was before starting the diet." Now he is able to imitate what he sees and focuses his attention to try to figure out what's going on.

This 80 percent improvement is fantastic news. This investigator expects this decline to continue as exposure to problem foods is eliminated.

Approach: Mark had been eating gluten-free casein-free foods since January 2000. Although this dietary change did yield positive results, his mother hoped for complete elimination of allergy symptoms. During the first eight weeks, Lisa followed the diet plan on her own. After the ninth week, the research investigator and counselors were consulted to formulate a more regulated rotation of the diet foods. Because Mark exhibited a delayed reaction to foods, cause-affect assessments were more challenging. Although Mark experienced a few setbacks due to the accidental re-exposure to non-diet foods, his symptoms have dropped over 80 percent from his original condition.

Dietary Considerations, Previous Exposure to Diet Foods: Because Mark's mother, Lisa, had been following the diet on her own, Mark had already been exposed to most of the diet foods for the two months. When the research investigator and counselors were consulted, they made sure to adjust his diet for the complete elimination of all food sensitivities. With his food allergies eliminated, Mark has an 80 percent improvement over his original condition.

Example Case Study: XVI. Autism, Constipation, Food Rituals

Figure 18:
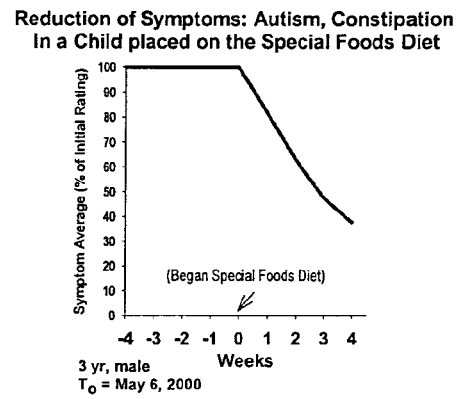
FIG. 18 is a graph showing reduction of particular symptoms in a child placed on the special foods diet.

Case Summary: FIG. 18 shows the improvements in symptom averages for an autistic child. Matthew's mom, Jenny, contacted the instant intervention program of Applicant seeking help for her three year-old autistic son. His repetitive self stimulating behavior, which included spinning in circles, clapping, and pacing, was fairly severe. He was also extremely sensitive to noise, particularly the loud noises emitted by the vacuum cleaner, stereo, TV and blender. Matthew also had a difficult time expressing himself, only able to repeat a few words and pick up intonations. Additionally, his eye contact was minimal and non-existent with strangers.

Aside from these developmental problems, Matthew also suffered from various physical ailments. From the age of six months on, Matthew had been constantly constipated. Patches of dry skin covered his back and there lingered a smooth red ring on his behind. His physical discomfort coupled with his autistic symptoms prompted Matthew's parents to look to The instant intervention program of Applicant for help.

Before beginning the program, Matthew would only eat squash, chickpea flour and chicken. These are the only foods that Matthew had eaten in three months. These foods slightly reduced the self stimulating behavior. Matthew occasionally ate other foods, but only if they were coated in chickpea flour, fried or salted. Because Matthew was used to those foods exclusively, he initially went through a typical withdrawal response and refused to eat the food on the Diet. Once his mother added uniodized sea salt, Matthew began eating more of the food. Almost immediately, she began to see an increase in eye contact, verbalization and less self stimulating.

However, Matthew's allergic sensitivity to the non-diet foods became obvious when he put a piece of his sibling's pizza crust in his mouth during the second week. His autistic and digestive problems regressed to their previous severe state for several days. Matthew also managed to take a drink of grape juice lying in the baby's crib. Again, self stimulating and fussiness increased after this incident. But once Matthew's diet was back under control, his symptoms resumed their steady decline. During the third week, though, Matthew again grabbed a piece of pizza and triggered a relapse of his symptoms that lasted four days. The research investigator and counselor is working with the family to make sure that harmful foods are kept away from Matthew's reach.

Matthew's chemical sensitivities began to become apparent in the beginning weeks of the program. His mother observed he was bothered by bathing, due to the chlorine in tap water, causing his mother to bathe him standing up. It was recommended that Jenny only use distilled water to bathe Matthew, brush his teeth and to diaper him. She also began to use Neolife Green to wash clothes and hand rinse clothing in distilled water. Jenny became concerned about fumes from the printing press her husband operated at work. It was recommended that he shower thoroughly, put his work clothes directly in the washer and use the same fragrance-free soaps as Matthew. Matthew was encouraged to spend the majority of his free time playing outdoors, which he seems to enjoy. By removing Matthew from these environmental irritants, and subjecting him to clean air Matthew's symptoms have shown significant improvement.

After three weeks in the instant intervention program of Applicant, Matthew experienced a dramatic decline in his constipation problems. His bowel movements are now normal: once per day with clear anal irrigation. He also has improved eye contact and the frequency of his physical stimulating attacks have declined. His patches of dry skin have also begun to recede.

Now into his fourth week of the program, Matthew has continued to show dissipating symptoms. Steps have been taken to keep him from smelling the non-diet foods that cause a return of the autism. Matthew is also beginning to eat more of the prescribed foods, as they are presented to him, and we look forward to satisfying this newfound hunger with a well balanced to continue his steady improvement.

Approach: Matthew began the program with a severe constipation and self stimulation problem that included spinning, clapping and pacing. He also had difficulty sustaining eye contact and had patches of dry, irritated skin on his back and bottom. The research investigator and counselors prepared a diet for Matthew to alleviate his symptoms. His mother then identified environmental sensitivities, such as the chlorine in tap water and the fumes from her husband's job as a printing press operator.

1. Dietary Consideration

A. Withdrawal: Matthew was accustomed to eating only squash, chickpea flour and chicken when he began the diet. During the first few days on the Instant plan, Matthew would not eat the food. To help Matthew cooperate, his mother used uniodized sea salt and he began to eat more of the food.

B. Non-Diet Foods: Although Matthew's symptoms improved when he adhered to the specific Diet, he managed to stray from the diet and eat a crust of pizza on two occasions. These deviations produced severe flare-ups in his symptoms, especially his self stimulating behavior. A similar pattern was observed when Matthew took a gulp of grape juice. These incidents convinced Jenny that Matthew's symptoms were related to his diet.

2. Environmental Considerations

A. Chemical Sensitivities: While Matthew was on the Diet, his mother became aware of an increased sensitivity to chlorine in tap water when Matthew became sensitive to bathing. To alleviate this chemical sensitivity, she used only distilled water to bathe Matthew, brush his teeth and diaper him. She also began washing his clothes with Neolife Green detergent and doing a final hand rinse in distilled water.

B. Fumes: Matthew's father works as a printing press operator and Jenny was concerned about the fumes affecting Matthew and exacerbating his symptoms. It was recommended that her husband go straight to the shower after work, immediately put his work clothes in the washer and use fragrance-free soap.

I hereby claim:

1. A method for dietary intervention, said method comprising:
   (a) withholding all food from an animal for at least 5 days, except for tropical root crops; and
   (b) feeding a concentrated form of tropical root crops to the animal for at least the five day period.

2. The method of claim 1, further comprising isolating the animal from environmental allergens subsequent to said withholding steps.

3. The method of claim 1, wherein said withholding and feeding steps extend for at least seven days.

4. The method of claim 1, comprising feeding foods from the same taxonomic family as the tropical root crops once every seven days following said initial feeding step.

5. The method of claim 4, comprising introducing unusual foods that the animal has eaten only once or twice in a preceding year period.

6. The method of claim 5, wherein said unusual food is selected from meat, oil, fats, and combinations thereof.

7. The method of claim 1, wherein said withholding also eliminates all supplements except mineral calcium.

8. The method of claim 1, wherein said tropical root crops are at least one selected from the group consisting of Convolvulaceae, Aroid, Euphorbiaceae, Nymphaceae, Cyperaceae, Dioscoreaceae and Marantaceae.

9. The method of claim 8, wherein the tropical root crop is selected so as to be fed in rotation only once in seven days.

10. The method of claim 1, wherein said tropical root crops are at least one selected from the group consisting of Convolvulaceae, Aroid, Euphorbiaceae, Nymphaceae, Cyperaceae, Dioscoreaceae, Marantaceae, Alismataceae, Cannaceae, Cycadaceae, Asclepiadaceae, Zingiberaceae, Iridaceae, Leguminosae, Muscaceae, Liliaceae, Typhaceae, Urticaceae, Lamiaceae and Cucurbitaceae.

11. The method of claim 1, wherein the animal is a human.

12. The method of claim 1, wherein the animal exhibits at least one symptom or condition selected from the group consisting of anxiety, arthritis, asthma, colic, congestion, diabetes, digestive upsets, irritable bowel syndrome, eczema, fatigue, migraine headaches, multiple sclerosis, seizures and rashes.

13. The method of claim 1, wherein the animal exhibits symptoms of multiple sclerosis.

14. The method of claim 1, wherein the animal exhibits at least one symptom or condition of Alzheimer's Disease.

15. The method of claim 1, wherein the steps of withholding and feeding are repeated at least once.

16. The method of claim 1, further comprising isolating the patient from environmental allergens during said withholding and feeding steps.

17. The method of claim 1, wherein the animal exhibits at least one condition or symptom selected from the group consisting of acid reflux, aggression, agitation, allergies, Alzheimer's disease, anxiety, arthritis, Asperger's syndrome, asthma, autism, bed wetting, biochemical imbalance, bizarre behaviors such as sucking on carpet and poking objects down his throat, bloating, Candidiasis, colic, congestion, constipation, cramps, Crohn's disease, dark circles under eyes, deep stuporous sleep, delayed motor skills, delayed social skills, diarrhea, diabetes, digestive upsets, eating disorders, eczema, emotional outbursts, enzyme deficiencies, fatigue, fatty acid imbalance, flushed face, food allergies, sensitivities, and intolerances, food-related problems, frequent ear infections, gas, headaches, head banging, hyperactivity, hypersensitivity to sensory stimuli such as noise, motion, light, touch, smell, commotion, and the like, hypotonic muscle tone, infantile spasms, insomnia, irritability, irritable bowel syndrome, irritated and injured mucous membranes of the GI tract, irritation and inflammation of mucosal linings, itching, leaking gut, lethargy, licking moldy areas, loose and bloody stools, loss of muscle tone, malabsorption, migraine headaches, multiple chemical sensitivities, multiple sclerosis, muscle aches, muscle stiffness, muscle weakness, muscle spasms, muscle tension, nausea, noise sensitivity, non-verbal autistic child, nutritional deficiencies, obsessive compulsive behaviors, obsessive compulsive disorders, other digestive conditions, outbursts of bawling, pain, panic attacks, paleness, post nasal drip, PDD, puffiness under eyes, rages, redhot feet, repeated infections of various kinds, screaming fits, seizures, self abuse, self-stimulating behaviors, sensory sensitivities, severe neurological effects and disorders, severely underweight, sleeping difficulties, shortness of breath, socially unresponsive, stomach aches, swelling, swollen and irritated mucous membranes, tantrums, temporary blindness, trancelike, dazed state, ulcerative colitis, uncontrollable anger, variety of malabsorption problems, various rashes, violence, violent behaviors, violent rages, vomiting, wide variety of emotions, withdrawn, and zoned out.

18. A method for dietary intervention in a human patient comprising:
   a. withholding all food from the patient for at least five days, except for specified crops; and
   b. feeding a concentrated form of said specified crops to the patient for at least the five day period;
   c. wherein the specified crops are selected from the group consisting of white sweet potatos, cassava, edible aroids, amaranth, true yams, malanga, lotus, quinoa, buckwheat, arrowroot and water chestnut.

* * * * *